United States Patent
Sugane et al.

(10) Patent No.: US 10,301,286 B2
(45) Date of Patent: May 28, 2019

(54) PIPERAZINE DERIVATIVE

(71) Applicant: Astellas Pharma Inc., Chuo-ku (JP)

(72) Inventors: Takashi Sugane, Tokyo (JP); Takuya Makino, Tokyo (JP); Daisuke Yamashita, Tokyo (JP); Yasuhiro Yonetoku, Tokyo (JP); Daisuke Tanabe, Tokyo (JP); Hisashi Mihara, Tokyo (JP); Norio Asai, Tokyo (JP); Kazuhiko Osoda, Tokyo (JP); Takafumi Shimizu, Tokyo (JP); Hiroyuki Moritomo, Tokyo (JP); Keizo Sugasawa, Tokyo (JP); Kyoichi Maeno, Tokyo (JP); Naomi Hosogai, Tokyo (JP)

(73) Assignee: Astellas Pharma Inc., Chuo-ku (JP)

( * ) Notice: Subject to any disclaimer, the term of this patent is extended or adjusted under 35 U.S.C. 154(b) by 0 days.

(21) Appl. No.: 15/749,375

(22) PCT Filed: Aug. 2, 2016

(86) PCT No.: PCT/JP2016/072569
§ 371 (c)(1),
(2) Date: Jan. 31, 2018

(87) PCT Pub. No.: WO2017/022733
PCT Pub. Date: Feb. 9, 2017

(65) Prior Publication Data
US 2018/0230131 A1 Aug. 16, 2018

(30) Foreign Application Priority Data

Aug. 4, 2015 (JP) .................. 2015-154601

(51) Int. Cl.
*C07D 403/06* (2006.01)
*C07D 401/14* (2006.01)
*C07D 405/14* (2006.01)
*A61K 31/496* (2006.01)
*A61K 31/501* (2006.01)
*C07D 403/14* (2006.01)
*C07D 409/14* (2006.01)
*C07D 417/14* (2006.01)
*A61P 13/02* (2006.01)
*A61P 13/10* (2006.01)

(52) U.S. Cl.
CPC .......... *C07D 403/06* (2013.01); *A61K 31/496* (2013.01); *A61K 31/501* (2013.01); *A61P 13/02* (2018.01); *A61P 13/10* (2018.01); *C07D 401/14* (2013.01); *C07D 403/14* (2013.01); *C07D 405/14* (2013.01); *C07D 409/14* (2013.01); *C07D 417/14* (2013.01)

(58) Field of Classification Search
CPC .................................................... C07D 403/06
USPC ....................................................... 514/252.2
See application file for complete search history.

(56) References Cited

U.S. PATENT DOCUMENTS

2004/0204398 A1   10/2004   Bakshi et al.
2017/0190697 A1   7/2017   Yamamoto et al.

FOREIGN PATENT DOCUMENTS

| WO | WO 2004/078716 A1 | 9/2004 |
| WO | WO 2005/040109 A1 | 5/2005 |
| WO | WO 2005/077935 A1 | 8/2005 |
| WO | WO 2006/020277 A2 | 2/2006 |
| WO | WO 2007/015157 A2 | 2/2007 |
| WO | WO 2007/096763 A2 | 8/2007 |
| WO | WO 2008/039418 A2 | 4/2008 |
| WO | WO 2010/015972 A1 | 2/2010 |

OTHER PUBLICATIONS

International Search Report dated Oct. 25, 2016 in PCT/JP2016/072569 (with English translation), 6 pages.
Written Opinion of the International Searching Authority dated Oct. 25, 2016 in PCT/JP2016/072569 filed Aug. 2, 2016 (with English translation), 9 pages.
Extended European Search Report dated Dec. 6, 2018 in European Patent Application No. 16833012.4, 5 pages.

*Primary Examiner* — Kahsay Habte
(74) *Attorney, Agent, or Firm* — Oblon, McClelland, Maier & Neustadt, L.L.P.

(57) ABSTRACT

To provide a compound which can be used as an MC$_4$ receptor agonist.

The present inventors have investigated MC$_4$ receptor agonists, and have found that a piperazine derivative has an action related to the agonists, thereby completing the present invention. That is, the piperazine derivative of the present invention has an MC$_4$ receptor agonistic action, and can be used as an agent for preventing or treating bladder and/or urinary tract diseases, in particular, underactive bladder, hypotonic bladder, acontractile bladder, detrusor underactivity, neurogenic bladder, urethral relaxation failure, detrusor-external urethral sphincter dyssynergia, and voiding dysfunctions in benign prostatic hyperplasia.

15 Claims, No Drawings

PIPERAZINE DERIVATIVE

TECHNICAL FIELD

The present invention relates to a piperazine derivative or a salt thereof, which has a melanocortin 4 receptor (hereinafter referred to as an $MC_4$ receptor) agonistic action, and can be used an active ingredient of a pharmaceutical composition, in particular, a pharmaceutical composition for preventing or treating bladder and/or urinary tract diseases.

BACKGROUND ART

Important roles of the lower urinary tract are urine storage and voiding, which are regulated by a coordinated action of the bladder and the urethra. That is, during urine storage, the bladder smooth muscle is relaxed and the urethral smooth muscle and the urethral sphincter are contracted, whereby a state of high urethral resistance is maintained and urinary continence is thus maintained. On the other hand, during voiding, while the bladder smooth muscle is contracted, the urethral smooth muscle is relaxed, and contraction of the external urethral sphincter is also suppressed. Examples of dysfunctions in the lower urinary tract include urine storage dysfunctions such as overactive bladder in which urine cannot be retained during urine storage, and voiding dysfunctions in which urine cannot be drained sufficiently during voiding due to increase in the urethral resistance or decrease in the bladder contractile force. These two dysfunctions may develop simultaneously in some cases.

Voiding dysfunctions are caused by an increase in urethral resistance or a decrease in the bladder contractile force during voiding, and lead to voiding difficulty, straining during voiding, attenuation of the urinary stream, extension of voiding time, an increase in residual urine, a decrease in voiding efficiency, or the like. As a cause of an increase in urethral resistance, a voiding dysfunction associated with benign prostatic hyperplasia is well-known, which is characterized by partial obstruction of the urethra due to nodular hypertrophy of the prostate tissues. Adrenergic $\alpha_1$ receptor antagonists have now been used as therapeutic agents for the voiding dysfunction associated with benign prostatic hyperplasia (Pharmacology, 65, 119-128 (2002)). An increase in the urethral resistance is also caused by functional obstruction in detrusor-external urethral sphincter dyssynergia due to neurological diseases or neurological disorders, or the like. With patients with these diseases, the effectiveness of adrenergic $\alpha_1$ receptor antagonists is unclear (Journal of Pharmacological Sciences, 112, 121-127 (2010)).

On the other hand, as a factor for decreasing the bladder contractile force during voiding, increasing age, diabetes, benign prostatic hyperplasia, neurological diseases such as Parkinson's disease and multiple sclerosis, spinal cord injury, nerve damage caused by pelvic surgery, and the like are known (Reviews in Urology, 15, 11-22 (2013)). As a therapeutic drug for a decrease in the bladder contractile force during voiding, bethanechol chloride which is a non-selective muscarinic receptor agonist, distigmine bromide which is a choline esterase inhibitor, and the like are known. However, it is known that these drugs have cholinergic side effects, such as diarrhea, abdominal pain, sweating, and the like. In addition, cholinergic crisis is sometimes expressed as a serious side effect, and caution is therefore required for the use (UBRETID (registered trademark) tablet 5 mg package insert, Torii Pharmaceutical Co., Ltd., Besacolin (registered trademark) powder 5% package insert, Eisai Co., Ltd.).

In voiding dysfunctions caused by an increase in the urethral resistance or a decrease in the bladder contractile force as described above, residual urine after voiding may be observed in some cases. Increased residual urine may cause a decrease in effective bladder capacity, and thus cause overactive bladder symptoms such as urinary frequency, or severe symptoms such as hydronephrosis in some cases. Therefore, there is a demand for a therapeutic agent which is more effective on bladder and/or urinary tract diseases or symptoms thereof caused by an increase in the urethral resistance during voiding or a decrease in the bladder contractile force (Reviews in Urology, 15, 11-22 (2013)).

Melanocortins are peptides that are generated by the processing from proopiomelanocortin, and examples thereof include an adrenocorticotropic hormone, and α-, β-, and γ-melanocyte stimulating hormones (α-, β-, and γ-MSH). Five subtypes ($MC_1$ to $MC_5$) have hitherto been reported as a melanocortin receptor. Any of the subtypes belong to a G protein-conjugated receptor of a class A, and activates an adenylate cyclase via the Gs protein to increase the amount of cAMPs. The $MC_4$ receptors are widely distributed in the central nervous system, and are known to play an important role in feeding behavior, energy metabolism regulation, sexual function, and the like (Journal of Pharmacological Sciences, 128, 53-55 (2006)).

As a representative $MC_4$ receptor agonist, the following ones have been reported.

In Patent Document 1, it is disclosed that an MC receptor ligand represented by the following general formula is useful for eating disorder, sexual dysfunction, skin disorder, chronic pain, anxiety, depression, obesity, and the like.

[Chem. 1]

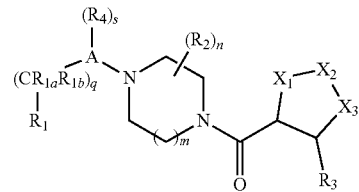

(In the formula, A represents $C_{5-7}$ cycloalkyl, aryl, or heteroaryl. For the other symbols, refer to Patent Document 1.)

In Patent Document 2, it is disclosed that an $MC_4$ receptor agonist represented by the following general formula is useful for obesity, diabetes, female sexual dysfunction, erectile dysfunction, and the like.

[Chem. 2]

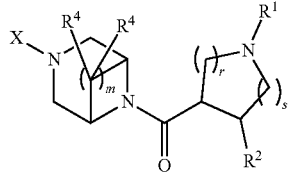

(In the formula, $R_1$ represents a $C_{1-6}$ alkyl group, X represents $—(CH_2)_n$-phenyl or $—(CH_2)_nC(R^5)(R^6)(R^7)$, in which $(CH_2)$ may have a substituent such as $C_{1-4}$ alkyl, $R^5$ represents $—(CH_2)_n$-phenyl or the like, $R^6$ represents H, $R^7$ represents —$(CH_2)_nN(R^8)_2$, and m represents 0. For the other symbols, refer to Patent Document 2.)

In Patent Document 3, it is disclosed that an $MC_4$ receptor modulator represented by the following general formula is useful for obesity, diabetes, male erectile dysfunction, or the like.

[Chem. 3]

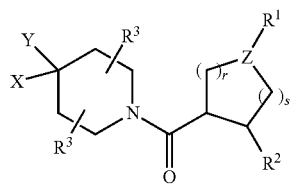

(For the symbols in the formula, refer to Patent Document 3.)

In Patent Document 4, it is disclosed that an $MC_4$ receptor agonist represented by the following general formula is useful for obesity, diabetes, female sexual dysfunction, erectile dysfunction, or the like.

[Chem. 4]

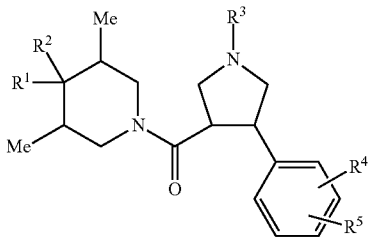

(For the symbols in the formula, refer to Patent Document 4.)

In Patent Document 5, it is disclosed that the $MC_4$ receptor agonist is useful for lower urinary tract disorder, particularly urinary incontinence, and an $MC_4$ receptor agonist represented by the following general formula is disclosed.

[Chem. 5]

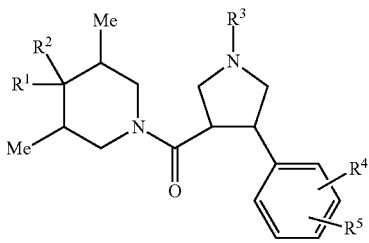

(For the symbols in the formula, refer to Patent Document 5.)

In Patent Document 5, it is described that the compound of Example 8 has an action of increasing the urethral pressure in the pharmacological data.

In Patent Document 6, it is disclosed that an $MC_4$ receptor agonist represented by the following general formula is useful for sexual dysfunction, obesity, diabetes, lower urinary tract disorder, or the like.

[Chem. 6]

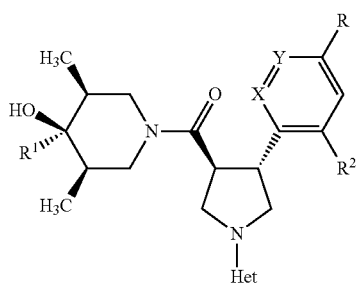

(For the other symbols, refer to Patent Document 6.)

In Patent Document 7, it is disclosed that an $MC_4$ receptor agonist represented by the following general formula is useful for sexual dysfunction, obesity, diabetes, lower urinary tract disorder, or the like.

[Chem. 7]

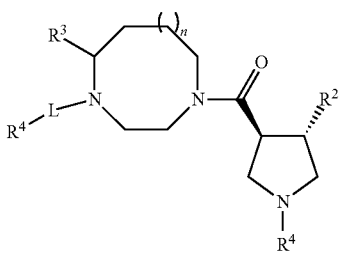

(In the formula, $R^3$ represents phenyl or pyridyl, and n represents 0 or 1. For the other symbols, refer to Patent Document 7.)

RELATED ART

Patent Document

[Patent Document 1] WO 2005/040109
[Patent Document 2] WO 2004/078716
[Patent Document 3] WO 2008/039418
[Patent Document 4] WO 2005/077935
[Patent Document 5] WO 2007/015157
[Patent Document 6] WO 2007/096763
[Patent Document 7] WO 2010/015972

DISCLOSURE OF INVENTION

Problems to be Solved by the Invention

The present invention has an object to provide a piperazine derivative which has an $MC_4$ receptor agonistic action and can be used as an active ingredient of a pharmaceutical composition for preventing or treating bladder and/or urinary tract diseases.

Means for Solving the Problems

The present inventors have made extensive studies for the creation of a novel therapeutic agent for bladder and/or urinary tract diseases, and as a result, they have found that an $MC_4$ receptor agonist relaxes the urethra to decrease the urethral pressure. Further, the present inventors have found that in model rats with drug-induced voiding dysfunctions, there is an action of inhibiting a decrease in voiding efficiency and an action of inhibiting an increase in the amount of the residual urine.

On the other hand, known $MC_4$ receptor agonists all have an action against central nervous system diseases such as eating disorders, obesity, sexual disorder, and the like In the case where they are used for preventing or treating bladder and/or urinary tract diseases, it is not preferable that the $MC_4$ receptor agonists express an action on central nervous system diseases (including, for example, an erection-inducing action) when administered at an effective amount. From this viewpoint, the present inventors have considered it preferable to separate an action on bladder and/or urinary tract diseases from an action on central nervous system diseases. Therefore, the present inventors have conducted further extensive studies for the purpose of creating a compound having a potent action on bladder and/or urinary tract diseases.

As a result, the present inventors have found that the piperazine derivative of the formula (I) has an excellent $MC_4$ receptor agonistic activity, and have also discovered that the piperazine derivative is useful as a drug for preventing or treating bladder and/or urinary tract diseases, thereby completing the present invention.

That is, the present invention relates to a compound of the formula (I) or a salt thereof, as well as a pharmaceutical composition comprising a compound of the formula (I) or a salt thereof and a pharmaceutically acceptable excipient.

[Chem. 8]

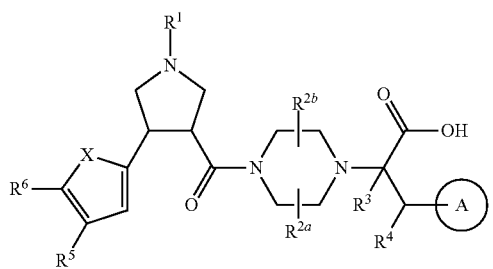

(I)

(In the formula, $R^1$ is H, $C_{1-6}$ alkyl which may be substituted with OH, $C_{3-8}$ cycloalkyl which may be substituted with $R^{00}$, heterocycloalkyl which may be substituted with $R^{00}$, phenyl which may be substituted with $R^{00}$, heteroaryl which may be substituted with $R^{00}$, —CO—$C_{1-6}$ alkyl, or —CO—$C_{3-8}$ cycloalkyl, in which $R^{00}$ represents substituents selected from the group consisting of $C_{1-6}$ alkyl, halogeno-$C_{1-6}$ alkyl, and halogen, $R^{2a}$ is $C_{1-6}$ alkyl which may be substituted with $R^{01}$, in which $R^{01}$ represents substituents selected from the group consisting of $C_{3-8}$ cycloalkyl, —O—($C_{1-6}$ alkyl), —N($C_{1-6}$ alkyl)$_2$, —NH($C_{1-6}$ alkyl), and —NH$_2$, $R^{2b}$ is H or $C_{1-6}$ alkyl, $R^{2a}$ and $R^{2b}$ may be combined with the same carbon atom in the piperazine ring to form $C_{3-8}$ cycloalkyl, $R^3$ is H or $C_{1-6}$ alkyl, $R^4$ is H or $C_{1-6}$ alkyl, X is *—$CR^7$=$CR^8$—, *—$CR^7$=N—, *—N=$CR^8$—, or S, in which * represents a bond with a carbon atom substituted with $R^6$, $R^5$, $R^6$, and $R^7$ are the same as or different from each other, and are H, $C_{1-6}$ alkyl, —O—($C_{1-6}$ alkyl), halogen, or CN, $R^5$ and $R^6$ may be combined with each other to form $C_{5-7}$ cycloalkenyl, $R^8$ is H or F, and the ring A is aryl which may be substituted with $R^{02}$, $C_{5-7}$ cycloalkenyl-fused phenyl which may be substituted with $R^{02}$, heteroaryl which may be substituted with $R^{02}$, or $C_{6-8}$ cycloalkyl which may be substituted with $R^{02}$, in which $R^{02}$ represents substituents selected from the group consisting of $C_{1-6}$ alkyl, halogeno-$C_{1-6}$ alkyl, $C_{3-8}$ cycloalkyl, —O—($C_{1-6}$ alkyl), —O-(halogeno-$C_{1-6}$ alkyl), halogen, and —CN.)

In addition, unless otherwise specified, when symbols in a certain chemical formula in the present specification are also used in another chemical formula, the same symbol represents the same meaning.

The present invention relates to a pharmaceutical composition, in particular, a pharmaceutical composition for preventing or treating bladder and/or urinary tract diseases, comprising the compound of the formula (I) or a salt thereof. Further, the pharmaceutical composition in the present invention includes a pharmaceutical composition, in particular, a pharmaceutical composition for preventing or treating bladder and/or urinary tract diseases, comprising the compound of the formula (I) or a salt thereof and a pharmaceutically acceptable excipient, and an agent for preventing or treating bladder and/or urinary tract diseases, comprising the compound of the formula (I) or a salt thereof and a pharmaceutically acceptable excipient.

The present invention relates to use of the compound of the formula (I) or a salt thereof for the manufacture of a pharmaceutical composition for preventing or treating bladder and/or urinary tract diseases; use of the compound of the formula (I) or a salt thereof for preventing or treating bladder and/or urinary tract diseases; the compound of the formula (I) or a salt thereof for preventing or treating bladder and/or urinary tract diseases; and a method for preventing or treating bladder and/or urinary tract diseases, including administering an effective amount of the compound of the formula (I) or a salt thereof to a subject. In addition, the "subject" is a human or another animal in need of such prevention or treatment, and in a certain aspect, a human in need of such prevention or treatment.

In addition, the present invention further includes a pharmaceutical composition for preventing or treating bladder and/or urinary tract diseases, comprising an $MC_4$ receptor agonist as an active ingredient.

Effects of the Invention

The compound of the formula (I) or a salt thereof is a compound having an $MC_4$ receptor agonistic activity, and can be used as an active ingredient of a pharmaceutical composition for preventing or treating bladder and/or urinary tract diseases.

EMBODIMENTS FOR CARRYING OUT THE INVENTION

Hereinafter, the present invention will be described in detail.

In the present specification, the "bladder and/or urinary tract diseases" particularly refers to voiding dysfunctions in the bladder and/or urinary tract diseases, and they are, for example, voiding dysfunctions in underactive bladder, hypotonic bladder, acontractile bladder, detrusor underactivity, neurogenic bladder, urethral relaxation failure, detrusor-external urethral sphincter dyssynergia, overactive bladder, urinary frequency, nocturia, urinary incontinence, benign prostatic hyperplasia, interstitial cystitis, chronic prostatitis, and urethral calculus, or the like, and preferably voiding dysfunctions in underactive bladder, hypotonic bladder, acontractile bladder, detrusor underactivity, neurogenic bladder, urethral relaxation failure, detrusor-external urethral sphincter dyssynergia, and benign prostatic hyperplasia.

The "$C_{1-6}$ alkyl" refers to linear or branched alkyl having 1 to 6 carbon atoms (hereinafter abbreviated $C_{1-6}$). Examples thereof include methyl, ethyl, n-propyl, isopropyl, n-butyl, isobutyl, sec-butyl, tert-butyl, n-pentyl, n-hexyl, and the like. In a certain aspect, the $C_{1-6}$ alkyl is $C_{1-4}$ alkyl; in a certain aspect, methyl, ethyl, n-propyl, or tert-butyl; in a certain aspect, methyl or tert-butyl; in a certain aspect, methyl; and in a certain aspect, tert-butyl.

The "halogeno-$C_{1-6}$ alkyl" refers to $C_{1-6}$ alkyl substituted with one or more halogen atoms. In a certain aspect, the halogeno-$C_{1-6}$ alkyl is $C_{1-6}$ alkyl substituted with 1 to 5 halogen atoms; in a certain aspect, difluoromethyl or trifluoromethyl; and in a certain aspect, trifluoromethyl.

The "$C_{3-8}$ cycloalkyl" refers to a $C_{3-8}$ saturated hydrocarbon ring group, which may have a bridge and may form a Spiro ring. Examples thereof include cyclopropyl, cyclobutyl, cyclopentyl, cyclohexyl, cycloheptyl, cyclooctyl, bicyclo[2,2,1]heptyl, bicyclo[3,1,0]hexyl, bicyclo[3,1,1]heptyl, spiro[2,5]octyl, and the like. In a certain aspect, the $C_{3-8}$ cycloalkyl is $C_{3-5}$ cycloalkyl; and in a certain aspect, $C_{6-8}$ cycloalkyl. In a certain aspect, the $C_{3-5}$ cycloalkyl is cyclopropyl. In a certain aspect, the $C_{6-8}$ cycloalkyl is cyclohexyl or cycloheptyl; in a certain aspect, cyclohexyl; and in a certain aspect, cycloheptyl. Further, the "$C_{6-8}$ cycloalkyl" refers to a $C_{6-8}$ saturated hydrocarbon ring group included in the "$C_{3-8}$ cycloalkyl".

The "$C_{5-7}$ cycloalkenyl" refers to a $C_{5-7}$ hydrocarbon ring group having one or more unsaturated bonds, which may have a bridge and form a spiro ring. Examples thereof include cyclopentenyl, cyclopentadienyl, cyclohexenyl, cyclohexadienyl, and the like. Further, the "$C_{5-7}$ cycloalkenyl-fused phenyl" refers to phenyl fused at the site of an unsaturated bond of $C_{5-7}$ cycloalkenyl, and examples thereof include 1-tetrahydronaphthyl, 2-tetrahydronaphthyl, dihydroinden-4-yl, 2,3-dihydro-1H-inden-5-yl, 1-indenyl, 2-indenyl, and the like. In a certain aspect, the $C_{5-7}$ cycloalkenyl-fused phenyl is 2-tetrahydronaphthyl; and in a certain aspect, 2,3-dihydro-1H-inden-5-yl.

The "aryl" is a monocyclic to tricyclic aromatic hydrocarbon ring group having 6 to 14 carbon atoms, and examples thereof include phenyl, naphthyl, anthracenyl, and the like. In a certain aspect, the aryl is phenyl; and in a certain aspect, naphthyl.

The "heteroaryl" refers to a 5- or 6-membered monocyclic heteroaryl including one or more hetero atoms selected from O, N, and S as a ring-constituting atom, or a bicyclic heteroaryl in which the monocyclic heteroaryl is fused with a benzene ring. Further, some of the bonds may be unsaturated. Incidentally, the carbon atom which is a ring-constituting atom may be substituted with oxo. Examples of the 5-membered heteroaryl include imidazolyl, triazolyl, tetrazolyl, thiazolyl, pyrazolyl, isothiazolyl, oxazolyl, isoxazolyl, thiadiazolyl, oxadiazolyl, thienyl, furyl, pyrrolyl and the like; examples of the 6-membered heteroaryl include pyridyl, pyrazinyl, pyrimidinyl, pyridazinyl, 1,6-dihydro-6-oxopyridazinyl, and the like; and examples of the bicyclic heteroaryl in which the monocyclic heteroaryl is fused with a benzene ring include indolyl, isoindolyl, benzofuryl, benzothienyl, indazolyl, benzoimidazolyl, benzoxazolyl, benzothiazolyl, quinolyl, isoquinolyl, cinnolinyl, phthalazinyl, quinazolinyl, quinoxalinyl, and the like. In a certain aspect, the heteroaryl is thiazolyl, thienyl, pyridyl, pyridazinyl, 1,6-dihydro-6-oxopyridazinyl, or indolyl; in a certain aspect, pyridyl; in a certain aspect, pyridazinyl; and in a certain aspect, 1,6-dihydro-6-oxopyridazinyl.

The "heterocycloalkyl" refers to a 3- to 7-membered monocyclic heterocycloalkyl including one or more hetero atoms selected from O, N, and S as a ring-constituting atom. Examples thereof include aziridinyl, azetidinyl, oxetanyl, pyrrolidinyl, imidazolidinyl, pyrazolidinyl, tetrahydrofuranyl, oxazolidinyl, piperidyl, piperazinyl, 4-tetrahydropyranyl, morpholinyl, thiomorpholinyl, thiazolidinyl, isothiazolidinyl, oxazolidinyl, azepanyl, diazepanyl, and the like. In a certain aspect, the heterocycloalkyl is tetrahydrofuranyl or 4-tetrahydropyranyl; and in a certain aspect, 4-tetrahydropyranyl.

In the present specification, the expression "which may be substituted" means "which is not substituted" or "which is substituted with 1 to 5 substituent(s)". Further, if it has a plurality of substituents, the substituents may be the same as or different from each other.

$R^{00}$ represents substituents selected from the group consisting of $C_{1-6}$ alkyl, halogeno-$C_{1-6}$ alkyl, and halogen. Examples thereof include, in a certain aspect, substituents selected from the group consisting of methyl, difluoromethyl, trifluoromethyl, and —F; and in a certain aspect, substituents selected from the group consisting of methyl and difluoromethyl.

$R^{01}$ represents substituents selected from the group consisting of $C_{3-8}$ cycloalkyl, —O—($C_{1-6}$ alkyl), —N($C_{1-6}$ alkyl)$_2$, —NH($C_{1-6}$ alkyl), and —NH$_2$; and examples thereof include, in a certain aspect, substituents selected from the group consisting of $R^{03}$.

$R^{02}$ represents substituents selected from the group consisting of $C_{1-6}$ alkyl, halogeno-$C_{1-6}$ alkyl, $C_{3-8}$ cycloalkyl, —O—($C_{1-6}$ alkyl), —O-(halogeno-$C_{1-6}$ alkyl), halogen, and —CN. Examples thereof include, in a certain aspect, substituents selected from the group consisting of methyl, tert-butyl, trifluoromethyl, cyclopropyl, methoxy, difluoromethoxy, trifluoromethoxy, halogen, and —CN; in a certain aspect, substituents selected from the group consisting of methyl, tert-butyl, cyclopropyl, and halogen; and in a certain aspect, substituents selected from the group consisting of methyl and halogen.

$R^{03}$ represents substituents selected from the group consisting of $C_{3-5}$ cycloalkyl, —O—($C_{1-6}$ alkyl), and —N($C_{1-6}$ alkyl)$_2$; and examples thereof include, in a certain aspect, substituents selected from the group consisting of cyclopropyl, methoxy, and —N-dimethyl.

The "halogen" refers to F, Cl, Br, or I; and in a certain aspect, F or Cl.

In a certain aspect of the formula (I), the compound is a compound defined by the following formula (Ia) or a salt thereof.

[Chem. 9]

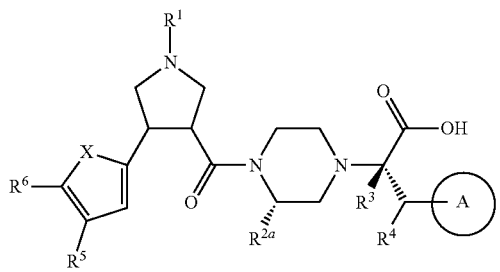

(Ia)

In a certain aspect of the formulae (I) and (Ia), the compound is a compound defined by the following formula (Ib) or a salt thereof.

[Chem. 10]

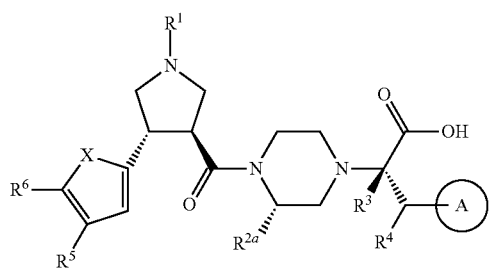

(Ib)

Some aspects of the compounds of the formulae (I), (Ia), and (Ib) of the present invention are shown below.

(1-1) The compound or a salt thereof, in which
$R^1$ is
i. tert-butyl which may be substituted with OH,
ii. $C_{3-5}$ cycloalkyl which may be substituted with $C_{1-6}$ alkyl,
iii. 4-tetrahydropyranyl which may be substituted with $C_{1-6}$ alkyl,
iv. phenyl which may be substituted with halogen,
v. heteroaryl which may be substituted with substituents selected from the group consisting of $C_{1-6}$ alkyl and halogeno-$C_{1-6}$ alkyl,
vi. —CO—$C_{1-6}$ alkyl, or
vii. —CO—$C_{3-5}$ cycloalkyl.

(1-2) The compound or a salt thereof, in which
$R^1$ is
i. tert-butyl,
ii. 4-tetrahydropyranyl,
iii. pyridyl which may be substituted with halogeno-$C_{1-6}$ alkyl, or
iv. 1,6-dihydro-6-oxopyridazinyl which may be substituted with $C_{1-6}$ alkyl.

(1-3) The compound or a salt thereof, in which
$R^1$ is
i. tert-butyl,
ii. 4-tetrahydropyranyl,
iii. pyridyl which may be substituted with difluoromethyl, or
iv. 1,6-dihydro-6-oxopyridazinyl which may be substituted with methyl.

(1-4) The compound or a salt thereof, in which
$R^1$ is
i. tert-butyl or
ii. 4-tetrahydropyranyl.

(2-1) The compound or a salt thereof, in which
$R^{2a}$ is $C_{1-6}$ alkyl which may be substituted with $R^{03}$, and $R^{03}$ represents substituents selected from the group consisting of $C_{3-5}$ cycloalkyl, —O—($C_{1-6}$ alkyl), and —N($C_{1-6}$ alkyl)$_2$.

(2-2) The compound or a salt thereof, in which $R^{2a}$ is $C_{1-6}$ alkyl.

(2-3) The compound or a salt thereof, in which $R^{2a}$ is methyl, ethyl, or n-propyl.

(2-4) The compound or a salt thereof, in which $R^{2a}$ is methyl.

(3-1) The compound or a salt thereof, in which $R^{2b}$ is H or $C_{1-6}$ alkyl.

(3-2) The compound or a salt thereof, in which $R^{2b}$ is H.

(4-1) The compound or a salt thereof, in which $R^3$ is H or $C_{1-6}$ alkyl.

(4-2) The compound or a salt thereof, in which $R^3$ is H or methyl.

(4-3) The compound or a salt thereof, in which $R^3$ is H.

(5-1) The compound or a salt thereof, in which $R^4$ is H or $C_{1-6}$ alkyl.

(5-2) The compound or a salt thereof, in which $R^4$ is H or methyl.

(5-3) The compound or a salt thereof, in which $R^4$ is H.

(6-1) The compound or a salt thereof, in which
X is *—$CR^7$=$CR^8$—, *—$CR^7$=N—, *—N=$CR^8$—, or S, and
* represents a bond with a carbon atom substituted with $R^6$.

(6-2) The compound or a salt thereof, in which
X is *—$CR^7$=$CR^8$— or *—N=$CR^8$—, and
* represents a bond with a carbon atom substituted with $R^6$.

(6-3) The compound or a salt thereof, in which
X is *—$CR^7$=$CR^8$—, and
* represents a bond with a carbon atom substituted with $R^6$.

(7-1) The compound or a salt thereof, in which $R^5$, $R^6$, and $R^7$ are the same as or different from each other and represent H, $C_{1-6}$ alkyl, or halogen.

(8-1) The compound or a salt thereof, in which $R^5$ is H or halogen.

(8-2) The compound or a salt thereof, in which $R^5$ is H.

(9-1) The compound or a salt thereof, in which $R^6$ is halogen.

(9-2) The compound or a salt thereof, in which $R^6$ is F or Cl.

(9-3) The compound or a salt thereof, in which $R^6$ is F.

(9-4) The compound or a salt thereof, in which $R^6$ is Cl.

(10-1) The compound or a salt thereof, in which $R^7$ is H or halogen.

(10-2) The compound or a salt thereof, in which $R^7$ is H.

(11-1) The compound or a salt thereof, in which $R^8$ is H or F.

(11-2) The compound or a salt thereof, in which $R^8$ is F.

(12-1) The compound or a salt thereof, in which
the ring A is
i. aryl which may be substituted with substituents selected from the group consisting of $C_{1-6}$ alkyl, halogeno-$C_{1-6}$ alkyl, $C_{3-5}$ cycloalkyl, —O—($C_{1-6}$ alkyl), —O-(halogeno-$C_{1-6}$ alkyl), halogen, and —CN, ii. $C_{5-7}$ cycloalkenyl-fused phenyl which may be substituted with substituents selected from the group consisting of $C_{1-6}$ alkyl and halogen,
   iii. heteroaryl which may be substituted with halogen, or
   iv. $C_{6-8}$ cycloalkyl which may be substituted with $C_{1-6}$ alkyl.

(12-2) The compound or a salt thereof, in which the ring A is
   i. phenyl which may be substituted with substituents selected from the group consisting of $C_{1-6}$ alkyl, $C_{3-5}$ cycloalkyl, and halogen,
   ii. naphthyl,
   iii. 2,3-dihydro-1H-inden-5-yl which may be substituted with substituents selected from the group consisting of $C_{1-6}$ alkyl and halogen,
   iv. cyclohexyl which may be substituted with $C_{1-6}$ alkyl, or
   v. cycloheptyl which may be substituted with $C_{1-6}$ alkyl.

(12-3) The compound or a salt thereof, in which
the ring A is
   i. phenyl which may be substituted with substituents selected from the group consisting of $C_{1-6}$ alkyl, $C_{3-5}$ cycloalkyl, and halogen,
   ii. naphthyl,
   iii. 2,3-dihydro-1H-inden-5-yl which may be substituted with substituents selected from the group consisting of $C_{1-6}$ alkyl and halogen, or
   iv. cyclohexyl which may be substituted with $C_{1-6}$ alkyl.

(12-4) The compound or a salt thereof, in which
the ring A is
   i. phenyl which may be substituted with substituents selected from the group consisting of $C_{1-6}$ alkyl and halogen,
   ii. naphthyl, or
   iii. 2,3-dihydro-1H-inden-5-yl.

(12-5) The compound or a salt thereof, in which
the ring A is
   i. phenyl which may be substituted with substituents selected from the group consisting of methyl and F,
   ii. naphthyl, or
   iii. 2,3-dihydro-1H-inden-5-yl.

(12-6) The compound or a salt thereof, in which the ring A is phenyl which may be substituted with substituents selected from the group consisting of $C_{1-6}$ alkyl and halogen.

(13) The compound or a salt thereof, which is a combination of any two or more of the aspects described in (1-1) to (12-6) in the formulae (I), (Ia), and (Ib) in which the two or more of the aspects are not inconsistent to each other.

Examples of the aspect (13) of the present invention include the compounds or a salt thereof shown below.

(14-1)
The compound of the formula (I) or a salt thereof, in which
$R^1$ is
   i. tert-butyl which may be substituted with OH,
   ii. $C_{3-5}$ cycloalkyl which may be substituted with $C_{1-6}$ alkyl,
   iii. 4-tetrahydropyranyl which may be substituted with $C_{1-6}$ alkyl,
   iv. phenyl which may be substituted with halogen,
   v. heteroaryl which may be substituted with substituents selected from the group consisting of $C_{1-6}$ alkyl and halogeno-$C_{1-6}$ alkyl,
   vi. —CO—$C_{1-6}$ alkyl, or
   vii. —CO—$C_{3-5}$ cycloalkyl,
$R^{2a}$ is $C_{1-6}$ alkyl which may be substituted with $R^{03}$,
   in which $R^{03}$ represents substituents selected from the group consisting of $C_{3-5}$ cycloalkyl, —O—($C_{1-6}$ alkyl), and —N($C_{1-6}$ alkyl)$_2$,
$R^{2b}$ is H or $C_{1-6}$ alkyl,
$R^3$ is H or $C_{1-6}$ alkyl,
$R^4$ is H or $C_{1-6}$ alkyl,
X is *—CR$^7$=CR$^8$—, *—CR$^7$=N—, *—N=CR$^8$—, or S,
   in which * represents a bond with a carbon atom substituted with $R^6$,
$R^5$, $R^6$, and $R^7$ are the same as or different from each other, and are H, $C_{1-6}$ alkyl, or halogen,
$R^8$ is H or F, and
the ring A is
   i. aryl which may be substituted with substituents selected from the group consisting of $C_{1-6}$ alkyl, halogeno-$C_{1-6}$ alkyl, $C_{3-5}$ cycloalkyl, —O—($C_{1-6}$ alkyl), —O-(halogeno-$C_{1-6}$ alkyl), halogen, and —CN,
   ii. $C_{5-7}$ cycloalkenyl-fused phenyl which may be substituted with substituents selected from the group consisting of $C_{1-6}$ alkyl and halogen,
   iii. heteroaryl which may be substituted with halogen, or
   iv. $C_{6-8}$ cycloalkyl which may be substituted with $C_{1-6}$ alkyl.

(14-2) The compound of the formula (I) or a salt thereof, in which
$R^1$ is
   i. tert-butyl,
   ii. 4-tetrahydropyranyl,
   iii. pyridyl which may be substituted with halogeno-$C_{1-6}$ alkyl, or
   iv. 1,6-dihydro-6-oxopyridazinyl which may be substituted with $C_{1-6}$ alkyl,
$R^{2a}$ is $C_{1-6}$ alkyl,
$R^{2b}$ is H,
$R^3$ is H or methyl,
$R^4$ is H or methyl,
X is *—CR$^7$=CR$^8$— or *—N=CR$^8$—,
   in which * represents a bond with a carbon atom substituted with $R^6$,
$R^5$ is H or halogen,
$R^6$ is halogen,
$R^7$ is H or halogen,
$R^8$ is F, and
the ring A is
   i. phenyl which may be substituted with substituents selected from the group consisting of $C_{1-6}$ alkyl, $C_{3-5}$ cycloalkyl and halogen,
   ii. naphthyl,
   iii. 2,3-dihydro-1H-inden-5-yl which may be substituted with substituents selected from the group consisting of $C_{1-6}$ alkyl and halogen,
   iv. cyclohexyl which may be substituted with $C_{1-6}$ alkyl, or
   v. cycloheptyl which may be substituted with $C_{1-6}$ alkyl.

(14-3)
The compound of the formula (I) or a salt thereof as described in (14-2), in which the formula (I) is the following the formula (Ia):

[Chem. 11]

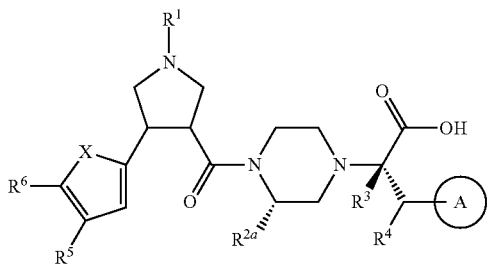

(Ia)

R¹ is
i. tert-butyl,
ii. 4-tetrahydropyranyl,
iii. pyridyl which may be substituted with difluoromethyl, or
iv. 1,6-dihydro-6-oxopyridazinyl which may be substituted with methyl,
$R^{2a}$ is methyl, ethyl, or n-propyl,
$R^3$ is H or methyl,
$R^4$ is H or methyl,
X is *—$CR^7$=$CR^8$—,
in which * represents a bond with a carbon atom substituted with $R^6$,
$R^5$ is H,
$R^6$ is F or Cl,
$R^7$ is H,
$R^8$ is F, and
the ring A is
i. phenyl which may be substituted with substituents selected from the group consisting of $C_{1-6}$ alkyl, $C_{3-5}$ cycloalkyl and halogen,
ii. naphthyl,
iii. 2,3-dihydro-1H-inden-5-yl which may be substituted with substituents selected from the group consisting of $C_{1-6}$ alkyl and halogen, or
iv. cyclohexyl which may be substituted with $C_{1-6}$ alkyl.
(14-4)
The compound or a salt thereof as described in (14-3), in which the formula (Ia) is the following formula (Ib):

[Chem. 12]

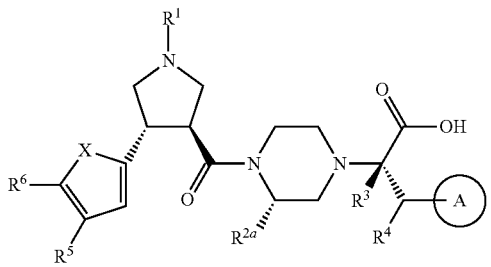

(Ib)

R¹ is
i. tert-butyl, or
ii. 4-tetrahydropyranyl,
$R^{2a}$ is methyl, ethyl, or n-propyl,
$R^3$ is H,
$R^4$ is H,
X is *—$CR^7$=$CR^8$—,
in which * represents a bond with a carbon atom substituted with $R^6$,
$R^5$ is H,
$R^6$ is F or Cl,
$R^7$ is H,
$R^8$ is F, and
the ring A is
i. phenyl which may be substituted with substituents selected from the group consisting of $C_{1-6}$ alkyl and halogen,
ii. naphthyl, or
iii. 2,3-dihydro-1H-inden-5-yl.

Examples of the specific compounds included in the present invention include the following compounds or salts thereof.

Compounds selected from the group consisting of the following compounds or salts thereof:
(2S)-2-[(3S)-4-{[(3S,4R)-4-(4-chloro-2-fluorophenyl)-1-(tetrahydro-2H-pyran-4-yl)pyrrolidin-3-yl]carbonyl}-3-methylpiperazin-1-yl]-3-(2-fluoro-4-methylphenyl)propanoic acid,
(2S)-2-[(3S)-4-{[(3S,4R)-4-(4-chloro-2-fluorophenyl)-1-(tetrahydro-2H-pyran-4-yl)pyrrolidin-3-yl]carbonyl}-3-methylpiperazin-1-yl]-3-(2-fluoro-4,6-dimethylphenyl)propanoic acid,
(2S)-2-[(3S)-4-{[(3S,4R)-1-tert-butyl-4-(4-chloro-2-fluorophenyl)pyrrolidin-3-yl]carbonyl}-3-methylpiperazin-1-yl]-3-mesitylpropanoic acid,
(2S)-2-[(3S)-4-{[(3S,4R)-1-tert-butyl-4-(4-chloro-2-fluorophenyl)pyrrolidin-3-yl]carbonyl}-3-methylpiperazin-1-yl]-3-(2-fluoro-4-methylphenyl)propanoic acid,
(2S)-2-[(3S)-4-{[(3S,4R)-1-tert-butyl-4-(2,4-difluorophenyl)pyrrolidin-3-yl]carbonyl}-3-methylpiperazin-1-yl]-3-(2,3-dihydro-1H-inden-5-yl)propanoic acid,
(2S)-2-[(3S)-4-{[(3S,4R)-1-tert-butyl-4-(2,4-difluorophenyl)pyrrolidin-3-yl]carbonyl}-3-propylpiperazin-1-yl]-3-(2-naphthyl)propanoic acid, and
(2S)-2-[(3S)-4-{[(3S,4R)-1-tert-butyl-4-(4-chloro-2-fluorophenyl)pyrrolidin-3-yl]carbonyl}-3-methylpiperazin-1-yl]-3-(4-methylphenyl)propanoic acid.

The following descriptions about the compound of the formula (I) also apply to the compounds of the formula (Ia) and the formula (Ib) unless otherwise specified.

The compound of the formula (I) may exist in the form of tautomers or geometrical isomers depending on the kind of substituents. In the present specification, the compound of the formula (I) shall be described in only one isomer form, yet the present invention includes any other isomers, in their isolated form, or as mixtures thereof.

In addition, the compound of the formula (I) may have asymmetric carbon atoms or axis chirality with no indication of stereochemistry in some cases, and therefore, optical isomers may exist based thereon. The present invention includes isolated forms of optical isomers of the compound of the formula (I) or any mixture thereof.

Moreover, the present invention also includes a pharmaceutically acceptable prodrug of the compound of the formula (I). The pharmaceutically acceptable prodrug is a compound having a group that can be converted into an amino group, a hydroxyl group, a carboxyl group, or the like through solvolysis or under physiological conditions. Examples of the group forming the prodrug include the groups described in Prog. Med., 5, 2157-2161 (1985) and "Pharmaceutical Research and Development" (Hirokawa Publishing Company, 1990), Vol. 7, Molecular Design, 163-198.

Moreover, the salt of the compound of the formula (I) is a pharmaceutically acceptable salt of the compound of the formula (I) and may form an acid addition salt or a salt with a base depending on the kind of substituents. Specific examples thereof include acid addition salts with inorganic acids such as hydrochloric acid, hydrobromic acid, hydroiodic acid, sulfuric acid, nitric acid, and phosphoric acid, and with organic acids such as formic acid, acetic acid, propionic acid, oxalic acid, malonic acid, succinic acid, fumaric acid, maleic acid, lactic acid, malic acid, mandelic acid, tartaric acid, dibenzoyltartaric acid, ditoluoyltartaric acid, citric acid, methanesulfonic acid, ethanesulfonic acid, benzenesulfonic acid, p-toluenesulfonic acid, aspartic acid, and glutamic acid, and salts with inorganic bases such as sodium, potassium, magnesium, calcium, and aluminum, or organic bases such as methylamine, ethylamine, ethanolamine, lysine, and ornithine, salts with various amino acids or amino acid derivatives such as acetylleucine, ammonium salts, and the like.

A salt of the compound of the formula (I) can also be prepared by an ordinary method.

Isolation and purification are carried out by employing ordinary chemical operations such as extraction, fractional crystallization, and various types of fractional chromatography.

Various isomers can be prepared by selecting appropriate starting compounds or by separation using differences in physicochemical properties between the isomers. For example, optical isomers can be obtained by means of a general optical resolution method for racemic products (for example, fractional crystallization for inducing diastereomer salts with optically active bases or acids, and chromatography using a chiral column or the like), and further, the isomers can also be prepared from an appropriate optically active starting compound.

Furthermore, the present invention also includes various hydrates or solvates, and polymorphic crystalline substances of the compound of the formula (I) or a salt thereof. In addition, the present invention also includes compounds labeled with various radioactive or non-radioactive isotopes.

In the powder X-ray diffraction pattern described in the present specification, the numeral values obtained from various patterns have some errors caused by the direction of the crystal growth, the size of particles, measurement conditions, or the like in some cases. The error range of a diffraction angle (2θ (°)) in the powder X-ray diffraction is ±0.2° in a certain aspect. Further, for example, in the case of performing measurement in the state of a mixture with additives of a pharmaceutical product, a peak may be apparently shifted by approximately ±0.3° in a peak which exists in the vicinity of a peak derived from the additives of a pharmaceutical product and is on the slope of the peak derived from the additives of the pharmaceutical product in some cases. In addition, in the powder X-ray diffraction pattern, crystal lattice intervals or overall patterns are important for identification of crystals in terms of the properties of the data, and since the diffraction angle and the diffraction intensity may vary slightly depending on the direction of crystal growth, the particle size, and the measurement conditions, they should not be strictly construed.

(Preparation Methods)

The compound of the formula (I) or a salt thereof can be prepared using the characteristics based on the basic structure or the type of substituents thereof and by applying various known synthesis methods. During the preparation, replacing the relevant functional group with a suitable protective group (a group that can be easily converted into the relevant functional group) at the stage from starting material to an intermediate may be effective depending on the type of the functional group in the production technology in some cases. The protective group for such a functional group may include, for example, the protective groups described in "Greene's Protective Groups in Organic Synthesis (4$^{th}$ edition, 2006)", P. G M. Wuts and T. W. Greene, and one of these may be selected and used as necessary depending on the reaction conditions. In this kind of method, a desired compound can be obtained by introducing the protective group, by carrying out the reaction and by eliminating the protective group as necessary.

In addition, prodrugs of the compound of the formula (I) can be prepared by introducing a specific group or by carrying out the reaction using the obtained compound of the formula (I) at the stage from a starting material to an intermediate, just as in the case of the above-mentioned protective group. The reaction can be carried out using methods known to a person skilled in the art, such as ordinary esterification, amidation, dehydration, and the like.

Hereinbelow, representative preparation methods for the compound of the formula (I) will be described. Each production process may also be carried out with reference to the References appended in the present description. Further, the preparation methods of the present invention are not limited to the examples shown below.

(Production Process 1)

[Chem. 13]

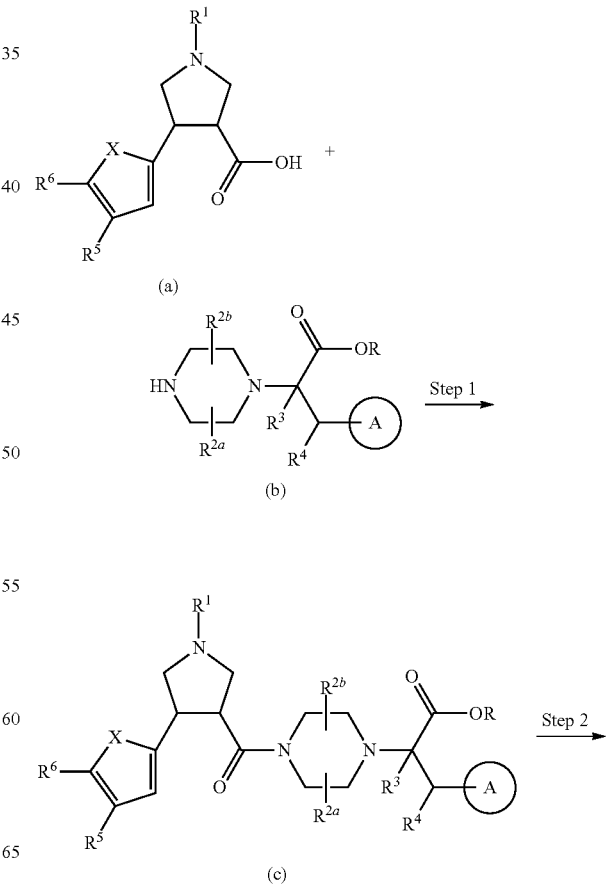

-continued

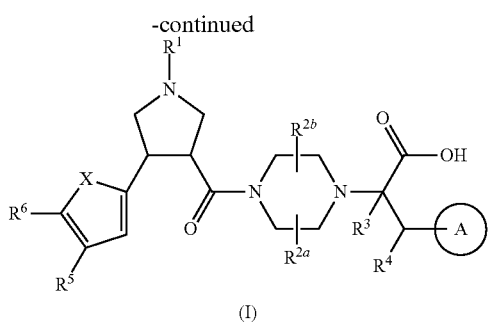

(In the formulae, R represents a protective group. The same shall apply hereinafter.)

The present production process is a method for preparing the compound of the formula (I) which is the compound of the present invention.

Here, examples of the protective group R include a methyl group, an ethyl group, a tert-butyl group, and the like.

(Step 1)

The present step is a step of obtaining a compound of the formula (c) by subjecting a compound of the formula (a) and a compound of the formula (b) to an amidation reaction.

In this reaction, the compound of the formula (a) and the compound of the formula (b) are used in equivalent amounts, or either thereof in an excess amount, and their mixture is stirred in a range from cooling to heating, preferably at −20° C. to 60° C., usually for 0.1 hours to 5 days, in a solvent which is inert to the reaction, in the presence of a condensing agent. Examples of the solvent used herein are not particularly limited, but include aromatic hydrocarbons such as benzene, toluene, xylene, and the like, halogenated hydrocarbons such as dichloromethane, 1,2-dichloroethane, chloroform, and the like, ethers such as diethyl ether, tetrahydrofuran, dioxane, 1,2-dimethoxyethane, and the like, N,N-dimethylformamide, dimethylsulfoxide, ethyl acetate, acetonitrile, or water, and any mixture thereof. Examples of the condensing agent include, but are not limited to, 1-(3-dimethylaminopropyl)-3-ethylcarbodiimide or a hydrochloride thereof, dicyclohexylcarbodiimide, 1,1'-carbonyldiimidazole, diphenylphosphoryl azide, phosphorous oxychloride, O-(7-aza-1H-benzotriazol-1-yl)-N,N,N',N'-tetramethyluronium hexafluorophosphate (HATU), and the like. It may be preferable in some cases for the reaction to use an additive (for example, 1-hydroxybenzotriazole). It may be advantageous in some cases for smooth progress of the reaction to carry out the reaction in the presence of organic bases such as triethylamine, N,N-diisopropyl ethylamine, N-methylmorpholine, and the like, or inorganic bases such as potassium carbonate, sodium carbonate, potassium hydroxide, and the like.

Furthermore, it is also possible to use a method in which a carboxylic acid (a) is converted to a reactive derivative and afterward reacted with an amine (b). Examples of the reactive derivative of the carboxylic acid include acid halides that can be obtained by the reaction with a halogenating agent such as phosphorus oxychloride, thionyl chloride, and the like, mixed acid anhydrides obtained by the reaction with isobutyl chloroformate, or the like, and active esters obtained by condensation with 1-hydroxybenzotriazole or the like. The reaction of these reactive derivatives with the compound (b) can be carried out in a range from cooling to heating, and preferably from −20° C. to 60° C., in a solvent which is inert to the reaction, such as halogenated hydrocarbons, aromatic hydrocarbons, ethers, and the like.

For a reference for the present reaction, reference can be made to, for example, the following one.

"Courses in Experimental Chemistry (5th edition)" edited by The Chemical Society of Japan, Vol. 16 (2005) (Maruzen)

(Step 2)

The present step is a method for preparing the compound of the formula (I) which is the compound of the present invention by deprotecting the compound of the formula (c).

The present reaction is carried out by stirring in a range from cooling to heating and refluxing, usually for 0.1 hours to 5 days. Examples of the solvent used herein are not particularly limited, but include alcohols such as methanol, ethanol, and the like, aromatic hydrocarbons such as benzene, toluene, xylene, and the like, halogenated hydrocarbons such as dichloromethane, 1,2-dichloroethane, chloroform, and the like, ethers such as diethyl ether, tetrahydrofuran, dioxane, dimethoxyethane, and the like, N,N-dimethylformamide, dimethylsulfoxide, ethyl acetate, acetonitrile, or water, and a mixture thereof. Examples of the deprotecting reagent are not particularly limited, but include bases such as an aqueous sodium hydroxide solution, an aqueous potassium hydroxide solution, an aqueous lithium hydroxide solution, and the like, and acids such as hydrochloric acid, trifluoroacetic acid, and the like.

For a reference for the present reaction, reference can be made to, for example, the following one.

"Courses in Experimental Chemistry (5th edition)" edited by The Chemical Society of Japan, Vol. 16 (2005) (Maruzen)

(Preparation of Starting Compounds)

The starting compounds in the preparation methods above can be prepared by, for example, the following method, the methods described in Preparation Examples which will be described later, well-known methods, or modified methods thereof.

(Starting Material Synthesis 1)

[Chem. 14]

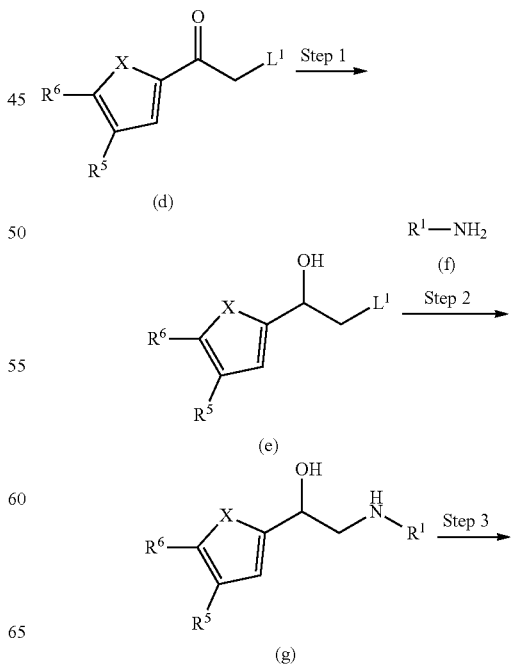

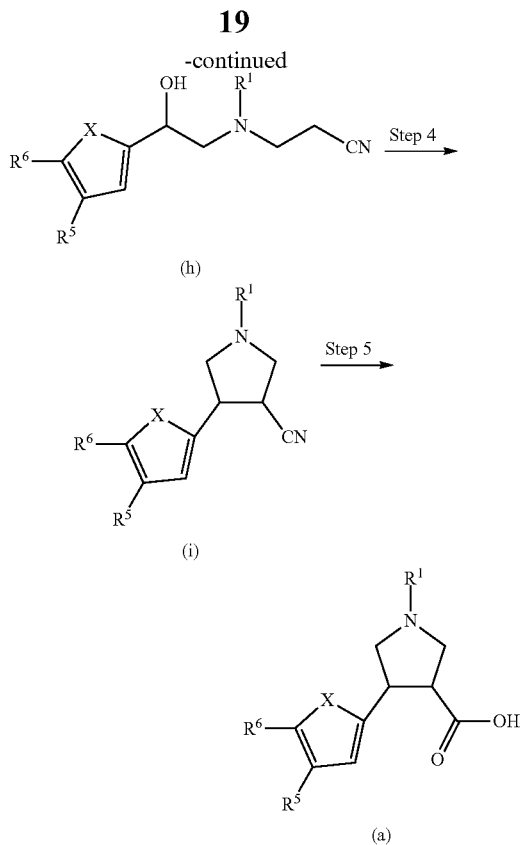

(In the formulae, $L^1$ represents a leaving group. This shall apply hereinafter.)

The present production process is a method for preparing the compound of the formula (a) which is a starting material for the compound of the formula (c).

Here, examples of the leaving group $L^1$ include a chloro group and the like.

(Step 1)

The present step is a method for preparing a compound of the formula (e) by subjecting the compound of the formula (d) to a reduction reaction.

The present reaction is carried out by reacting the compound of the formula (d) and a reducing agent in equivalent amounts, or either thereof in an excess amount in a range from cooling to heating and refluxing, preferably at −20° C. to 40° C., usually for 0.1 hours to 5 days, in a solvent which is inert to the reaction. Examples of the solvent used herein are not particularly limited, but include aromatic hydrocarbons such as benzene, toluene, xylene, and the like, ethers such as diethyl ether, methyl tert-butyl ether, tetrahydrofuran, dioxane, 1,2-dimethoxyethane, and the like, alcohols such as methanol, ethanol, and the like, or water, and a mixture thereof. Examples of the reducing agent include, but at not limited to, sodium borohydride, a borane-N,N-diethylaniline complex, and the like. Further, it may be advantageous in some cases for smooth progress of the reaction to use various additives. In addition, it may be preferable for obtaining the compound of the formula (e) in an optically active form in some cases to use an asymmetric agent catalyst together with the reducing agent (for example, a borane-N,N-diethylaniline complex and (S)-5,5-diphenyl-2-methyl-3,4-propano-1,3,2-oxazaborolidine ((S)-MeCBS)).

For a reference for the present reaction, reference can be made to, for example, the following ones.

"Courses in Experimental Chemistry (5$^{th}$ edition)" edited by The Chemical Society of Japan, Vol. 14 (2005) (Maruzen)

"Courses in Experimental Chemistry (5$^{th}$ edition)" edited by The Chemical Society of Japan, Vol. 19 (2005) (Maruzen)

J. Org. Chem. 70, 3592-3601 (2005)

(Step 2)

The present step is a step of preparing the compound of the formula (g) by reacting the compound of the formula (e) with a compound of the formula (0.

The present reaction is carried out by using the compound of the formula (e) and the compound of the formula (f) in equivalent amounts, or the compound of the formula (f) in an excess amount, and reacting the mixture in a range from cooling to heating and refluxing, preferably at 0° C. to 80° C., usually for 0.1 hours to 5 days, in a solvent which is inert to the reaction, in the presence of a base. Examples of the solvent used herein are not particularly limited, but include aromatic hydrocarbons such as benzene, toluene, xylene, and the like, alcohols such as methanol, ethanol, and the like, ethers such as diethyl ether, tetrahydrofuran, dioxane, 1,2-dimethoxyethane, and the like, halogenated hydrocarbons such as dichloromethane, 1,2-dichloroethane, chloroform, and the like, N,N-dimethylformamide, dimethylsulfoxide, ethyl acetate, acetonitrile, and a mixture thereof. Examples of the base are not particularly limited, but include organic bases such as triethylamine, N,N-diisopropylethylamine, 1,8-diazabicyclo[5.4.0]-7-undecene, n-butyllithium, and the like, and inorganic bases such as sodium hydroxide, sodium carbonate, potassium carbonate, cesium carbonate, sodium hydride, potassium tert-butoxide, and the like. It may be advantageous in some cases to carry out the reaction in the presence of a phase transfer catalyst such as tetra-n-butylammonium chloride and the like.

For a reference for the present reaction, reference can be made to, for example, the following one.

"Courses in Experimental Chemistry (5$^{th}$ edition)" edited by The Chemical Society of Japan, Vol. 14 (2005) (Maruzen)

(Step 3)

The present step is a step of preparing a compound of the formula (h) by subjecting the compound of the formula (g) and acrylonitrile to a conjugate addition reaction.

The present reaction is carried out by reacting the compound of the formula (g) and acrylonitrile in an excess amount in a range from cooling to heating, preferably at 40° C. to 80° C., usually for 12 hours to 5 days, in a solvent which is inert to the reaction. Further, it may be preferable in some cases to carry out the reaction in the absence of a solvent. In addition, it may be advantageous in some cases for smooth progress of the reaction to carry out the reaction to use ethanol, formamide, or the like as the additive.

For a reference for the present reaction, reference can be made to J. Org. Chem. 70, 3592-3601 (2005) as mentioned above.

(Step 4)

The present step is a step of preparing a compound of the formula (i) by subjecting the compound of the formula (h) to a cyclization reaction.

The present reaction is carried out by reacting the compound of the formula (h) with p-toluenesulfonic anhydride, methanesulfonic anhydride, diethyl chlorophosphate, or the like under cooling, preferably in a range from −78° C. to under ice-cooling, usually for 0.1 hours to 5 days, in a solvent which is inert to the reaction, in the presence of a base. Examples of the base are not particularly limited, but include lithium bis(trimethylsilyl)amide, sodium bis(trimethylsilylamide), potassium bis(trimethylsilyl)amide, and the like.

For a reference for the present reaction, reference can be made to, for example, J. Org. Chem. 70, 3592-3601 (2005) as described above.

(Step 5)

The present step is a step of preparing the compound of the formula (a) by subjecting the compound of the formula (i) to alkali hydrolysis.

The present reaction is carried out by stirring in a range of cooling to heating and refluxing, usually 0.1 hours to 5 days. Examples of the solvent used herein are not particularly limited, but include alcohols, acetone, N,N-dimethylformamide, tetrahydrofuran, and the like. Further, it may be suitable for the reaction in some cases to use a mixed solvent of the above solvent with water. Examples of the hydrolysis reagent are not particularly limited, but include bases such as an aqueous sodium hydroxide solution, an aqueous potassium hydroxide solution, and the like.

For a reference for the present reaction, reference can be made to, for example, the following one.

"Courses in Experimental Chemistry (5$^{th}$ edition)" edited by The Chemical Society of Japan, Vol. 16 (2005) (Maruzen)

(Starting Material Synthesis 2)

[Chem. 15]

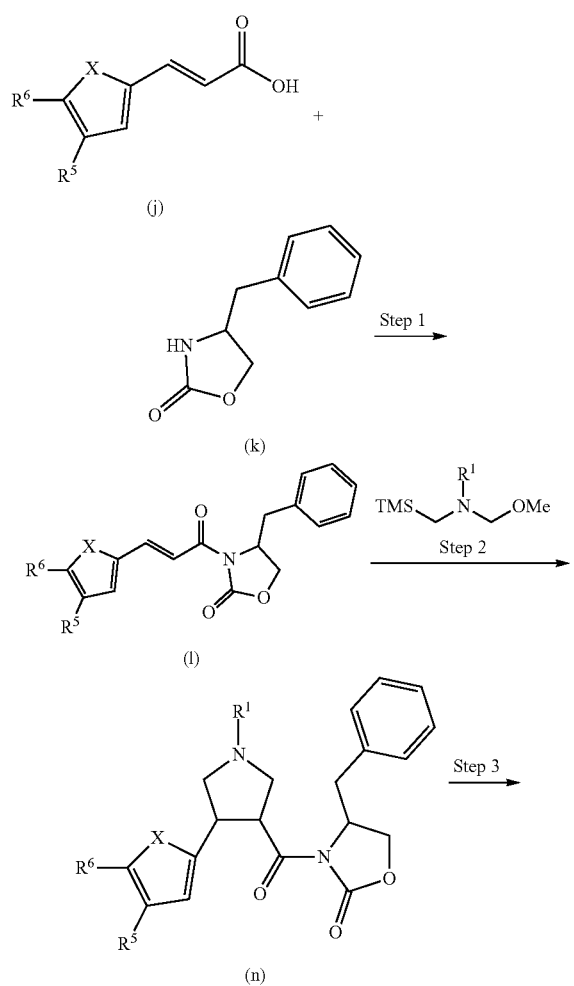

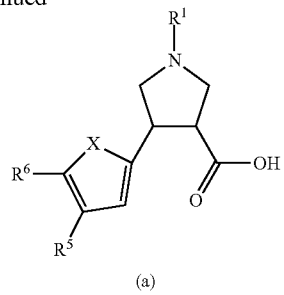

(a)

The present production process is a method for preparing the compound of the formula (a) which is a starting material for the compound of the formula (c).

(Step 1)

The present step is a step of preparing a compound of the formula (l) by subjecting the compound of the formula (j) and the compound of the formula (k) to an amidation reaction.

The present reaction can be carried out by the same method as Step 1 of Production Process 1 as described above. In addition, the reaction products after the next step can be obtained as an optically active form such as the compound of the formula (Ib) by using an optically active form as the compound of the formula (k) in some cases.

(Step 2)

The present step is a step of obtaining a compound of the formula (n) by subjecting the compound of the formula (l) and the compound of the formula (m) to a 1,3-dipolar cycloaddition reaction.

In the present reaction, the compound of the formula (l) and the compound of the formula (m) in equivalent amounts, or either thereof in an excess amount are used, and a mixture thereof is stirred in a range from cooling to heating, preferably at −20° C. to 60° C., usually for 0.1 hours to 5 days, in a solvent which is inert to the reaction, in the presence of an acid. Examples of the solvent used herein are not particularly limited, but include aromatic hydrocarbons such as benzene, toluene, xylene, and the like, and halogenated hydrocarbons such as dichloromethane, 1,2-dichloroethane, chloroform, and the like. Examples of the acid include trifluoroacetic acid and the like.

For a reference for the present reaction, reference can be made to, for example, the following one.

Tetrahedron: Asymmetry, 8, 883-887 (1997)

(Step 3)

The present step is a step of preparing the compound of the formula (a) by subjecting the compound of the formula (n) to alkali hydrolysis.

The present reaction can be carried out by the same method as for Step 5 of Starting Material Synthesis 1 as described above.

(Starting Material Synthesis 3)

[Chem. 16]

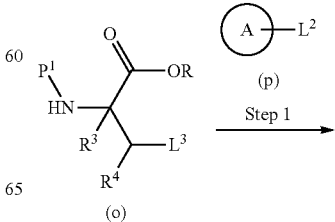

-continued

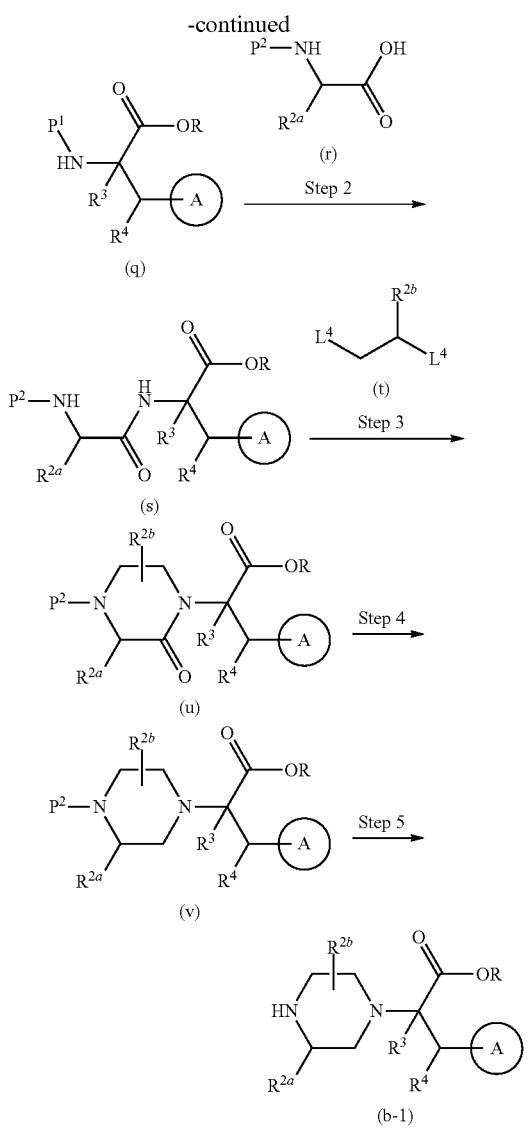

(In the formula, $L^2$ and $L^3$ represent halogen, $P^1$ or $P^2$ represents a protective group, and $L^4$ represents a leaving group. This shall apply hereinafter.)

The present production process is a method for preparing the compound of the formula (b-1) which is a starting material for the compound of the formula (c).

Here, examples of halogen, $L^2$ or $L^3$, include a bromo group and an iodine group. Examples of the protective group $P^1$ include a tert-butoxycarbonyl group and the like. Examples of the protective group $P^2$ include a 2-nitrobenzenesulfonyl group and the like. Examples of the leaving group $L^4$ include a bromo group and the like.

(Step 1)

The present step is a step of preparing the compound of the formula (q) from the compound of the formula (o) and the compound of the formula (p).

In the present reaction, zinc powder or the like is used as a metal reagent, and a so-called Negishi reaction of cross-coupling of an organic zinc compound and an organic halogen compound, can be used, which is a well-known reaction to a person skilled in the art.

The present reaction is carried out by performing a reaction in a range of cooling to heating and refluxing, preferably at −20° C. to 80° C., usually for 0.1 hours to 5 days, in a solvent which is inert to the reaction. Examples of the solvent used herein include tetrahydrofuran, N,N-dimethylformamide, and the like. Further, examples of the catalyst used include a nickel catalyst and a palladium catalyst. In addition, it may be advantageous to carry out the reaction in the presence of a phosphine ligand or the like in some cases.

For a reference for the present reaction, reference can be made to, for example, the following ones.

"Courses in Experimental Chemistry (5$^{th}$ edition)" edited by The Chemical Society of Japan, Vol. 13 (2005) (Maruzen)

J. Org. Chem. 75, 245-248 (2010)

(Step 2)

The present step is a step of preparing the compound of the formula (s) by deprotecting the protective group $P^1$ of the compound of the formula (q), and then subjecting it to an amidation reaction with the compound of the formula (r).

The present reaction can be carried out by deprotecting the protective group $P^1$ with reference to "Protective Groups in Organic Synthesis", Greene and Wuts, 4$^{th}$ edition, John Wiley & Sons Inc, 2006, and then performing the same method as Step 1 of Production Process 1 as described above.

(Step 3)

The present step is a step of preparing the compound of the formula (u) from the compound of the formula (s) and the compound of the formula (t).

The present reaction is carried out by performing a reaction in a range of cooling to heating and refluxing, preferably at 0° C. to 80° C., usually for 0.1 hours to 5 days, in a solvent which is inert to the reaction. Examples of the solvent used herein include acetonitrile, N,N-dimethylformamide, and the like. Examples of the base include, but are not limited to, inorganic bases such as potassium carbonate and the like.

(Step 4)

The present step is a step of preparing a compound of the formula (v) by subjecting the compound of the formula (u) to a reduction reaction.

The present reaction is carried out by reacting the compound of the formula (u) and a reducing agent in equivalent amounts or in an excess amount in a range from cooling to heating and refluxing, preferably at −20° C. to 40° C., usually for 0.1 hours to 5 days, in a solvent which is inert to the reaction. Examples of the solvent used herein are not particularly limited, but include aromatic hydrocarbons such as benzene, toluene, xylene, and the like, and ethers such as diethyl ether, tetrahydrofuran, dioxane, 1,2-dimethoxyethane, and the like. Examples of the reducing agent include, but at not limited to, lithium aluminum hydride, a borane-tetrahydrofuran complex, diborane, and the like.

For a reference for the present reaction, reference can be made to, for example, the following one.

"Courses in Experimental Chemistry" (5$^{th}$ edition) edited by The Chemical Society of Japan, Vol. 14 (2005) (Maruzen)

(Step 5)

The present step is a step of preparing the compound of the formula (b-1) by deprotecting the protective group $P^2$ of the compound of the formula (v).

The present reaction can be carried out with reference to "Protective Groups in Organic Synthesis", Greene and Wuts, 4$^{th}$ edition, John Wiley & Sons Inc, 2006 as described above.

(Starting Material Synthesis 4)

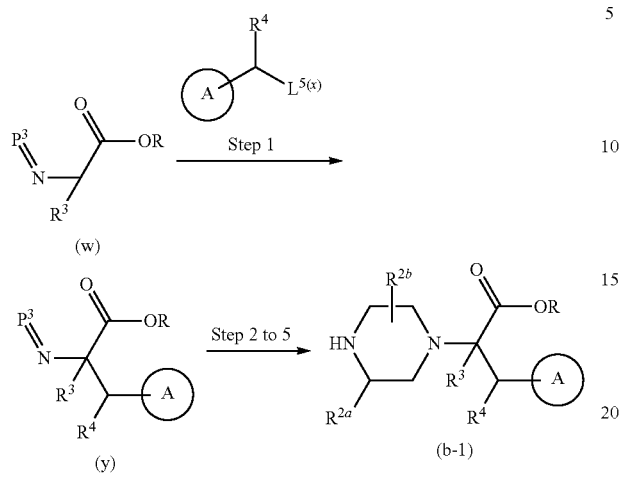

(In the formula, $L^5$ represents halogen and $P^3$ represents a protective group. This shall apply hereinafter.)

The present production process is a method for preparing the compound of the formula (b-1) which is a starting material for the compound of the formula (c).

Here, examples of the protective group $P^3$ include diphenylmethylidene group.

(Step 1)

The present step is a step of preparing a compound of the formula (y) from the compound of the formula (w) and the compound of the formula (x).

In the present reaction, the compound of the formula (w) and the compound of the formula (x) in equivalent amounts, or either thereof in an excess amount are used, and the mixture is stirred in a range from cooling to heating, and preferably under cooling, usually for 1 day to 10 days, in a solvent which is inert to the reaction, in the presence of a base. Examples of the solvent used herein are not particularly limited, but include aromatic hydrocarbons such as benzene, toluene, xylene, and the like, ethers such as diethyl ether, tetrahydrofuran, dioxane, 1,2-dimethoxyethane, and the like, or water, and a mixture thereof. Examples of the base include organic bases such as lithium diisopropylamide, triethylamine, N,N-diisopropyl ethylamine, potassium hexamethylenedisilazide, 1,8-diazabicyclo[5.4.0]-7-undecene, n-butyllithium, and the like, and inorganic bases such as sodium carbonate, potassium carbonate, cesium carbonate, sodium hydride, potassium hydroxide, potassium tert-butoxide, and the like.

In addition, the compound of the formula (y) can be obtained in the form of an optically active form by using a phase transfer catalyst that is optically active in some cases.

For a reference for the present reaction, reference can be made to, for example, the following ones.

"Courses in Experimental Chemistry ($5^{th}$ edition)" edited by The Chemical Society of Japan, Vol. 14 (2005) (Maruzen)

Angew. Chem. Int. Ed. 44, 1549-1551 (2005)

(Steps 2 to 5)

The present reaction can be carried out by deprotecting the protective group $P^3$ of the compound of the formula (y), and then performing the same methods as Steps 2 to 5 of Starting Material Synthesis 3 as described above.

TEST EXAMPLES

The pharmacological activities of the compound of the formula (I) were confirmed in the following tests. Further, in the present specification, the doses of the test compounds are expressed in conversion to the weight of free forms.

Unless otherwise specified, the present Test Examples can be accomplished according to known methods, and in the case of using commercially available reagents, kits, or the like, can be accomplished according to the instructions attached to the commercially available products.

Test Example 1

Test for Evaluating Human MC Receptor Activation, Using Cells Expressing Human $MC_4$, $MC_1$, or $MC_3$ Receptor Experiment Method (1) Construction of Human MC Receptor-Expressing Vector A human $MC_4$ receptor gene (GenBank Accession No.: NM_005912.2), a human $MC_1$ receptor gene (GenBank Accession No.: NM_002386.3), or a human $MC_3$ receptor gene (GenBank Accession No.: NM_019888.3) was introduced into an expression vector pcDNA™ 3.1/V5-His TOPO (registered trademark) (Thermo Fisher Scientific Inc.).

(2) Construction of Cells Transiently Expressing Human MC Receptor

An expression vector for a human $MC_4$, $MC_1$, or $MC_3$ receptor was introduced into FreeStyle™ 293-F cell (Thermo Fisher Scientific Inc., product number: R790-07). For the introduction, electroporation was employed. That is, $1\times10^7$ FreeStyle™ 293-F cell were suspended in 80 μL of an electroporation buffer (Thermo Fisher Scientific Inc., product number: B201-100), and 20 μg of the expression vector was added thereto. The resultant was put into a cuvette (OC-100 Processing Assembly, MaxCyte, Inc.) and electroporated with MaxCyte SIX (registered trademark) (MaxCyte, Inc.). The cells were cultured over one day, suspended in a Cell Banker (registered trademark) 1 (JUJI FIELD Inc.), product number: BLC-1), and stored frozen until their use.

(3) Measurement of Amount of cAMP Produced

Measurement was carried out by using a LANCE (registered trademark) Ultra cAMP Kit (PerkinElmer, Inc.) in accordance with the attached instructions. That is, after dissolution in DMSO, the test compound (a final concentration of 1 pM to 30 μM) diluted with an assay buffer (Hank's balanced salt solution, 5 mM 4-(2-hydroxyethyl)-1-piperazineethanesulfonic acid (HEPES), 0.5 mM 3-isobutyl-1-methylxanthine (IBMX), 0.1% bovine serum albumin, pH 7.4), or α-MSH (Bachem Inc., a final concentration of 1 pM to 30 μM) was added to OptiPlate-384 (PerkinElmer, Inc.). Furthermore, a suspension of cells transiently expressing the human $MC_4$, $MC_1$, or $MC_3$ receptor prepared by using the assay buffer was added thereto at 1,000 cells/well, followed by being left to stand at room temperature for about 1 hour. Thereafter, an Eu-cAMP tracer solution and an ULight™-anti-cAMP solution were added thereto, followed by being left to stand at room temperature for about 1 hour. The amount of cAMP was calculated using EnVision (registered trademark) (PerkinElmer Inc.).

For the agonistic activity, an efficacy ($EC_{50}$ (μM)) was calculated by a non-linear regression method with a Sigmoid-Emax model, by defining the maximum reaction with α-MSH as 100% and the reaction with the vehicle alone as 0%, respectively.

The $EC_{50}$ values of some Example compounds of the present invention are shown in Tables 1 and 2. Ex represents the Example No. of the test compound. In addition, NA represents Not Applicable and NT represents Not Tested.

TABLE 1

| | $EC_{50}$ (μM) | | |
|---|---|---|---|
| Ex | Human $MC_4$ | Human $MC_1$ | Human $MC_3$ |
| 4 | 0.0015 | 0.070 | 0.18 |
| 5 | 0.025 | 1.3 | 4.2 |
| 9 | 0.0032 | 0.39 | 0.91 |
| 11 | 0.017 | 0.86 | 3.7 |
| 76 | 0.00096 | 0.10 | 0.33 |
| 87 | 0.011 | 1.1 | 0.92 |
| 88 | 0.012 | 2.7 | 0.88 |
| 89 | 0.0030 | 1.3 | 0.78 |

TABLE 2

| | $EC_{50}$ (μM) | | |
|---|---|---|---|
| Ex | Human $MC_4$ | Human $MC_1$ | Human $MC_3$ |
| 6 | 0.48 | 6.4 | >30 |
| 13 | 0.048 | NA | 5.0 |
| 15 | 0.49 | NT | NT |
| 16 | 4.9 | NT | NT |
| 17 | 2.4 | NT | NT |
| 21 | 1.7 | NT | NT |
| 24 | 0.0032 | 15 | 0.58 |
| 27 | 1.0 | NT | NT |
| 28 | 0.15 | 3.9 | 10 |
| 33 | 0.61 | NT | NT |
| 35 | 0.14 | NT | NT |
| 36 | 0.0019 | NT | NT |
| 45 | 1.1 | NT | NT |
| 47 | 0.062 | >30 | 11 |
| 50 | 0.064 | NT | NT |
| 53 | 0.19 | NT | NT |
| 55 | 0.27 | NT | NT |
| 57 | 0.12 | 1.9 | 2.4 |
| 68 | 0.53 | NT | NT |
| 69 | 0.0051 | 0.72 | 2.9 |
| 72 | 0.040 | 2.1 | 5.3 |
| 74 | 0.030 | 1.4 | 1.0 |
| 78 | 0.016 | 1.0 | 0.68 |
| 83 | 0.19 | NT | NT |
| 84 | 0.018 | NT | NT |
| 92 | 0.012 | 1.7 | 1.8 |

From the above results, it was confirmed that the Example compounds of the present invention described above have an agonistic activity for the human $MC_4$ receptor. It was also confirmed that in the Example compounds which had been evaluated on the human $MC_1$ and $MC_3$ receptors among the Example compounds of the present invention described above, the $EC_{50}$ values for the human $MC_1$ and $MC_3$ receptors were at higher concentrations than those for the human $MC_4$ receptor, and the compounds act selectively on the $MC_4$ receptor.

Test Example 2

Test for Evaluating Rat $MC_4$ Receptor Activation, Using Cells Expressing Rat $MC_4$ Receptor Experiment Method (1) Construction of Rat $MC_4$ Receptor-Expressing Vector A rat $MC_4$ receptor gene (GenBank Accession No.: NM_013099.2) was introduced into an expression vector pcDNA™ 3.1/V5-His TOPO (registered trademark) (Thermo Fisher Scientific Inc.).

(2) Construction of Cells Transiently Expressing Rat $MC_4$ Receptor

An expression vector for a rat $MC_4$ receptor was introduced into FreeStyle™ 293-F cell (Thermo Fisher Scientific Inc.). For the introduction, electroporation was employed. That is, $1 \times 10^7$ FreeStyle™ 293-F cell were suspended in 80 μL of an electroporation buffer (Thermo Fisher Scientific Inc.), and 20 μg of the expression vector was added thereto. The resultant was put into a cuvette (OC-100 Processing Assembly, MaxCyte, Inc.) and electroporated with MaxCyte STX (registered trademark) (MaxCyte, Inc.). The cells were cultured over one day, suspended in a Cell Banker (registered trademark) 1 (JUJI FIELD Inc.), and stored frozen until use.

(3) Measurement of Amount of cAMP Produced

Measurement was carried out in accordance with the attached instructions, using a LANCE (registered trademark) Ultra cAMP Kit (PerkinElmer, Inc.). That is, after dissolution in DMSO, the test compound (a final concentration of 1 pM to 30 μM) diluted with an assay buffer (Hank's balanced salt solution, 5 mM HEPES, 0.5 mM IBMX, 0.1% bovine serum albumin, pH 7.4), or α-MSH (Bachem Inc., a final concentration of 1 pM to 30 μM) was added to OptiPlate-384 (PerkinElmer, Inc.). Furthermore, a suspension of cells transiently expressing the rat $MC_4$ receptor, that had been prepared using the assay buffer, was added thereto at 1,000 cells/well, followed by being left to stand at room temperature for about 1 hour. Thereafter, an Eu-cAMP tracer solution and an ULight™-anti-cAMP solution were added thereto, followed by being left to stand at room temperature for about 1 hour. The amount of cAMP was calculated using EnVision (registered trademark) (PerkinElmer Inc.).

For the agonistic activity, an efficacy ($EC_{50}$ (μM)) was calculated by a non-linear regression method with a Sigmoid-Emax model, by defining the maximum reaction with α-MSH as 100% and the reaction with the vehicle alone as 0%, respectively.

The $EC_{50}$ values of some Example compounds of the present invention are shown in Table 3. Ex represents the Example No. of the test compound.

TABLE 3

| Ex | $EC_{50}$ (μM) Rat $MC_4$ |
|---|---|
| 4 | 0.0013 |
| 5 | 0.026 |
| 9 | 0.0026 |
| 11 | 0.021 |
| 76 | 0.0017 |
| 87 | 0.021 |
| 88 | 0.011 |
| 89 | 0.0031 |

From the above results, it was confirmed that the Example compounds of the present invention described above have an agonistic activity for the rat $MC_4$ receptor.

Test Example 3

Action on Rat Urethral Pressure

Experiment Method

The present Test Example was carried out by partially modifying the technique reported as a testing system for evaluating an urethral resistance-reducing action (European Journal of Pharmacology, 679, 127-131 (2012)). Male Wistar rats (Charles River Laboratories Japan, Inc.) were anesthetized with urethane (1.2 g/kg ip), and placed in a supine position. The lower abdominal portion was midline-incised, and thus, the bladder was exposed. The bladder apex was incised, a microchip pressure transducer catheter (3.5 Fr, Millar) was inserted into the inside of the urethra, and then placed therein. In addition, a cannula for administration of a drug was placed into the femoral vein. After stabilization of the urethral pressure, phenylephrine hydrochloride (Sigma-Aldrich, 30 μg/kg) was administered intravenously to induce an increase in the urethral pressure. At an interval of about 30 minutes, this operation was repeated twice or more to confirm the stability of the reaction of a phenylephrine hydrochloride-induced increase in the urethral pressure. Thereafter, a test compound (dissolved in 20% dimethyl acetamide, 10% Cremophor (registered trademark) and 70% physiological saline) was intravenously administered, and then 5 minutes later, phenylephrine hydrochloride was administered. The procedure of administration of the test compound and administration of phenylephrine hydrochloride was repeated at an interval of about 30 minutes, and 3 to 5 doses of the test compound was evaluated (the test compound was administered at increasing doses). The data of reaction was introduced into a personal computer through PowerLab (registered trademark) (ADInstruments, Inc.), and analyzed with LabChart (registered trademark) (ADInstruments, Inc.). For the evaluation, the value of the area under the urethral pressure (mmHg·s) for one minute before and after administration of phenylephrine hydrochloride was determined to calculate the difference between before and after administration of phenylephrine hydrochloride (ΔAUC value). By taking the ΔAUC value obtained before administering the test compound as 100%, the ratio (reaction rate) of the ΔAUC value of the test compound at each dose was calculated. The rate at which the obtained reaction rate becomes 60% (40% as an inhibition rate) was defined as $ID_{40}$, and the $ID_{40}$ values of the test compounds were calculated by non-linear regression.

The $ID_{40}$ values of some Example compounds of the present invention are shown in Table 4. Ex represents the Example No. of the test compound.

TABLE 4

| Ex | $ID_{40}$ (mg/kg) |
| --- | --- |
| 4 | 0.0094 |
| 5 | 0.13 |
| 9 | 0.047 |
| 11 | 0.088 |
| 76 | 0.0047 |
| 87 | 0.040 |
| 88 | 0.040 |
| 89 | 0.024 |

From the above results, it was found that the Example compounds of the present invention described above have inhibitory effect on phenylephrine-induced increase in urethral pressure.

Test Example 4

Action on Drug-Induced Voiding Dysfunction Model Rat

Experiment Method

Male Sprague Dawley (SD) rats (Japan SLC, Inc.) were anesthetized with isoflurane and a cannula was placed in bladder, the stomach, and the jugular vein. Then, the rats were awakened in a Ballman cage (Natsume Seisakusho Co., Ltd.). After a post-operative stabilization period, physiological saline was continuously infused into the bladder by an infusion pump (Terumo Corporation, product number: TE-331S) to induce voiding. Infusion of the physiological saline was stopped at the time of voiding, and the amount of the voided urine was measured using an electronic top-loading balance placed under the Ballman cage. After completion of voiding, the residual urine was collected by gravity through the cannula placed in the bladder, and weighed, and the weight was defined as the amount of the residual urine. Further, the intravesical pressure was measured by a pressure transducer (Nihon Kohden Corporation, product numbers: TP-400, TDX-100) through the bladder cannula. The test compound or the vehicle was administered into the stomach, and atropine sulfate (Sigma-Aldrich, Inc., 0.01 mg/kg), which is an anticholinergic drug, and midodrine hydrochloride (Sigma-Aldrich, Inc., 0.3 mg/kg), which is an $\alpha_1$ adrenergic receptor stimulant, were administered intravenously to induce voiding dysfunctions. The voiding efficiency (=[voided amount/(voided amount+amount of residual urine)]×100) and the amount of the residual urine before and after administration of the test compound or the vehicle were measured, and the amount changed was evaluated. The value with vehicle administration and the value with the test compound administration were compared in a Dunnett's multiple comparison test with a statistically significant difference (P<0.05), and the minimum dose at which the inhibitory effect on a decrease in voiding efficiency or an increase of the amount of residual urine had been observed was defined as a minimal effective dose (3 to 12 animals per group).

The minimum effective doses of some Example compounds of the present invention are shown in Table 5. Ex represents the Example No. of the test compound.

TABLE 5

| Ex | Minimum effective dose (mg/kg) |
| --- | --- |
| 4 | 0.03 |
| 5 | 0.3 |
| 9 | 3 |
| 11 | 0.3 |
| 76 | 0.03 |
| 87 | 0.1 |
| 88 | 0.1 |
| 89 | 0.1 |

From the above results, it was confirmed that the Example compounds of the present invention described above have inhibitory effect on a decrease in voiding efficiency or an increase of the amount of residual urine.

Test Example 5

Rat Erection-Inducing Action

Experiment Method

Male SD rats (Charles River Laboratories Japan, Inc.) were used. A test compound (10 mg/kg) or the vehicle (20% dimethyl acetamide, 10% Cremophor (registered trademark), 70% physiological saline) was administered intravenously through the tail vein. After administration, the rats were transferred to transparent observation cages made of plastic to measure the erection times of up to one hour after administration. The measurements were carried out for five groups (3 to 7 animals per group): vehicle groups, Example compound groups (Ex 87, 88, and 89), and THIQ group, which had been known as an $MC_4$ receptor agonist (J. Med. Chem., 45, 4589-4593 (2002)), as a positive control. For a statistical significance test, Dunnett's multiple comparison test was used for the comparison with vehicle control group, and it was determined whether there was an erection-inducing effect with a statistically significant difference ($P<0.05$). As a result, THIQ as the positive control exhibited a significant erection-inducing effect, whereas all of the Example compounds (Ex 87, 88, and 89) did not exhibit an erection-inducing effect.

As seen from the results of each of the above tests, it was confirmed that the compound of the formula (I) has a human $MC_4$ receptor-selective agonistic activity, and it was also confirmed that the compound has inhibitory effect on phenylephrine-induced increase in urethral pressure in vivo. Further, it was confirmed that in a rat model with a voiding dysfunction, the compound has inhibitory effect on a decrease in voiding efficiency and an increase of the amount of residual urine. In addition, it was confirmed that some of the compounds of the formula (I) do not exhibit an erection-inducing effect which is an action on the central nervous system. Therefore, the compound of the formula (I) can be used for preventing or treating bladder and/or urinary tract diseases, in particular, voiding dysfunctions in bladder and/or urinary tract diseases. For example, the compound of the formula (I) can be used for preventing or treating voiding dysfunctions in underactive bladder, hypotonic bladder, acontractile bladder, detrusor underactivity, neurogenic bladder, urethral relaxation failure, detrusor-external urethral sphincter dyssynergia, overactive bladder, urinary frequency, nocturia, urinary incontinence, benign prostatic hyperplasia, interstitial cystitis, chronic prostatitis, urethral calculus, or the like. In particular, the compound of the formula (I) can be used for preventing or treating voiding dysfunctions in underactive bladder, hypotonic bladder, acontractile bladder, detrusor underactivity, neurogenic bladder, urethral relaxation failure, detrusor-external urethral sphincter dyssynergia, and benign prostatic hyperplasia.

A pharmaceutical composition containing one or more kinds of the compound of the formula (I) or a salt thereof as an active ingredient can be prepared using excipients that are usually used in the art, that is, excipients for pharmaceutical preparation, carriers for pharmaceutical preparation, and the like according to the methods usually used.

Administration can be accomplished either by oral administration via tablets, pills, capsules, granules, powders, solutions, and the like, or parenteral administration, such as injections such as intraarticular, intravenous, and intramuscular injections, suppositories, transdermal solutions, ointments, transdermal patches, transmucosal solutions, transmucosal patches, inhalers, and the like.

Solid compositions for oral administration are used in the form of tablets, powders, granules, or the like. In such solid compositions, one or more active ingredient(s) are mixed with at least one inactive excipient. In a conventional method, the composition may contain inactive additives, such as lubricants, disintegrating agents, stabilizers, or solubilization assisting agents. If necessary, tablets or pills may be coated with sugar or s gastric- or enteric-soluble substance films.

Liquid compositions for oral administration include pharmaceutically acceptable emulsions, solutions, suspensions, syrups, elixirs, or the like, and also include generally used inert diluents, for example, purified water or ethanol. In addition to the inert diluent, liquid compositions may also contain auxiliary agents, such as solubilization assisting agents, moistening agents, and suspending agents, sweeteners, flavors, aromatics, or antiseptics.

Injections for parenteral administration include sterile aqueous or non-aqueous solutions, suspensions, or emulsions. Aqueous solvents include, for example, distilled water for injection or physiological saline. Examples of non-aqueous solvents include alcohols such as ethanol. Such compositions may further contain tonicity agents, antiseptics, moistening agents, emulsifying agents, dispersing agents, stabilizers, or solubilization assisting agents. These are sterilized, for example, by filtration through bacteria retaining filter, blendings of bactericide, or irradiation. In addition, these can also be used by preparing sterile solid compositions, and dissolving or suspending in sterile water or sterile solvents for injection prior to use.

Agents for external use includes ointments, plasters, creams, jellies, poultices, sprays, lotions, and the like. The agents contain generally used ointment bases, lotion bases, aqueous or non-aqueous solutions, suspensions, emulsions, and the like.

As transmucosal agents such as inhalers, transnasal agents, and the like, those in the form of a solid, liquid, or semi-solid state are used, and can be prepared in accordance with conventionally known methods. For example, known excipients, and furthermore pH adjusting agents, antiseptics, surfactants, lubricants, stabilizers, thickening agents, or the like may be appropriately added thereto. For their administration, appropriate devices for inhalation or blowing can be used. For example, a compound may be administered alone or as a powder of formulated mixture, or as a solution or suspension in combination with pharmaceutically acceptable carriers, using a known device or sprayer, such as a measured administration inhalation device, and the like. Dry powder inhalers or the like may be for single or multiple administration use, and dry powder or powder-containing capsules may be used. Alternatively, these may be a pressurized aerosol spray which uses appropriate ejection agents, for example, a suitable gas such as chlorofluoroalkane, carbon dioxide, and the like.

For oral administration, a daily dose is generally about 0.001 mg/kg to 100 mg/kg, preferably 0.1 mg/kg to 30 mg/kg, and more preferably 0.1 mg/kg to 10 mg/kg, per body weight, administered in one portion or in 2 to 4 separate portions. In the case of intravenous administration, a daily dose to be administered is suitably about 0.0001 mg/kg to 10 mg/kg per body weight, once a day or two or more times a day. In addition, a transmucosal agent is administered at a dose from about 0.001 mg/kg to 100 mg/kg per body weight, once a day or two or more times a day. Doses are appropriately determined according to the individual according to the symptoms, age, gender, and the like.

Although varying depending on administration routes, formulations, administration sites, or the types of excipients or additives, the pharmaceutical composition of the present invention contains 0.01% by weight to 100% by weight, and in a certain embodiment, 0.01% by weight to 50% by weight of one or more kinds of the compound of the formula (I) or a salt thereof, which is an active ingredient.

The compound of the formula (I) can be used in combination with various agents for treating or preventing the diseases for which the compound of the formula (I) is considered to be effective, as described above. The combined preparation may be administered simultaneously, or separately and continuously, or at a desired time interval. The preparations to be administered simultaneously may be a mixture, or may be prepared individually.

EXAMPLES

Hereinbelow, the preparation methods for the compound of the formula (I) will be described in more detail with reference to Examples. Further, the present invention is not limited to the compounds described in Examples below. Incidentally, the production processes for the starting compounds will be described in Preparation Examples. Further, the preparation methods for the compound of the formula (I) are not limited to the preparation methods in specific Examples shown below, and the compound of the formula (I) can be prepared according to a combination of these preparation methods or methods apparent to those skilled in the art.

Moreover, the following abbreviations are used in tables below in some cases.

PEx: Preparation Example No., Ex: Example No., PSyn: Preparation method for Preparation Example compound (The number in the PSyn section indicates that the compound is prepared using the corresponding starting material by the same method as that for the compound with the number as the Preparation Example compound No. For example, a compound with 3 in the PSyn section means that the compound is prepared by the same method as that for the compound of Preparation Example 3), Syn: Preparation method for Example compound (The number in the Syn section indicates that the compound is prepared using the corresponding starting material by the same method as that for the compound with the number as the Example compound No. For example, a compound with 1 in the Syn section means that the compound is prepared by the same method as that for the compound of Example 1), Str: Chemical structural formula, DAT: Physicochemical data.

ESI+: m/z values in mass spectroscopy (Ionization ESI, representing [M+H]$^+$ unless specified), ESI−: m/z values in mass spectroscopy (Ionization ESI, representing [M−H]$^-$ unless specified), APCI/ESI+: APCI/ESI-MS (Atmospheric pressure chemical ionization APCI, APCI/ESI represents simultaneous measurement of APCI and ESI, representing [M+H]$^+$ unless specified), APCI/ESI−: APCI/ESI-MS (Atmospheric pressure chemical ionization APCI, APCI/ESI represents simultaneous measurement of APCI and ESI, representing [M−H]$^-$ unless specified), EI: m/z values in mass spectroscopy (Ionization EI, representing [M]$^+$ unless specified), CI: m/z values in mass spectroscopy (Ionization CI, representing [M+H]$^+$ unless specified).

$^1$H-NMR (400 MHz, DMSO-d6): δ (ppm) of signals in $^1$H-NMR in DMSO-d$_6$, $^1$H-NMR (400 MHz, CDCl$_3$): δ (ppm) of signals in $^1$H-NMR in CDCl$_3$, $^1$H-NMR (500 MHz, pyridine-d5, 90° C.): δ (ppm) of signals in $^1$H-NMR at a measurement temperature of 90° C. in pyridine-d5, s: singlet, d: doublet, t: triplet, q: quartet, br: broad line, m: multiplet.

Unless otherwise specified, the compound represents an optical isomer having the absolute steric configuration described in the chemical structural formula. The compound attached with "**" represents an optical isomer having the absolute steric configuration described in the chemical formula, in which the steric configuration in the asymmetric carbon moiety with no description of the steric configuration is single but undetermined. The compound attached with "$" has the denoted steric configuration, in which the steric form in the asymmetric carbon moiety with no description of the steric configuration is single but undetermined, and the steric configurations in the asymmetric carbon moiety between one compound and another compound described the same structural formula are in inverse relationship. The compound attached with "#" has the denoted steric configuration, in which the steric form in the asymmetric carbon moiety with no description of the steric configuration is a mixture of R and S forms. In the structural formula, HCl indicates that the compound is monohydrochloride, 2HCl indicates that the compound is dihydrochloride, and 3HCl indicates that the compound is trihydrochloride. In addition, the compound indicated by both HCl and HBr represents monohydrobromide-monohydrochloride.

Incidentally, in the present specification, nomenclature software such as ACD/Name (registered trademark, Advanced Chemistry Development, Inc.) may be used in some cases for the nomenclature of the compounds.

The powder X-ray diffraction was measured using RINT-TTRII under the conditions of a tube of Cu, a tube current of 300 mA, a tube voltage of 50 kV, a sampling width of 0.020°, a scanning speed of 4°/min, a wavelength of 1.54056 angstroms, and a range of diffraction angles to be measured (2θ) of 2.5° to 40°. Further, devices including data processing was handled according to the methods and procedures, respectively instructed in each of the devices.

Furthermore, for convenience, the concentration mol/L is represented by M. For example, a 1 M aqueous sodium hydroxide solution means a 1 mol/L aqueous sodium hydroxide solution.

Preparation Example 1

Under a nitrogen atmosphere, a mixture of borane-N,N-diethylaniline complex (46.2 g), (S)-5,5-diphenyl-2-methyl-3,4-propano-1,3,2-oxaoxazaborolidine (1 M toluene solution, 5 mL), and tert-butylmethyl ether (250 mL) was heated at 35° C. Then, a solution of 2-chloro-1-(4-chloro-2-fluorophenyl)ethanone (51 g) in tert-butylmethyl ether (300 mL) was added dropwise thereto at 40° C. for 2 hours. After completion of dropwise addition, the mixture was stirred overnight while being left to be cooled to room temperature. The reaction mixture was ice-cooled and methanol (150 mL) was added dropwise thereto. Thereafter, a mixture of concentrated hydrochloric acid (80 mL) and water (220 mL) was added dropwise thereto, followed by stirring for 1 hour still under ice-cooling. The aqueous layer and the organic layer were separated, and then the aqueous layer was extracted with tert-butylmethyl ether. The organic layer was combined, washed with brine, and dried over anhydrous magnesium sulfate. The insoluble materials were separated by filtration and the filtrate was concentrated under reduced pressure. To the obtained residue was added hexane (100 mL), followed by stirring at room temperature for 1 hour and then stirring for 1 hour under ice-cooling. The resulting solid was collected by filtration and washed with ice-cooled hexane. The obtained solid was dried under reduced pressure at room temperature to obtain (1S)-2-chloro-1-(4-chloro-2-fluorophenyl)ethanol (42.4 g) as a solid.

Preparation Example 2

A mixture of (1S)-2-chloro-1-(4-chloro-2-fluorophenyl)ethanol (8 g) and methanol (4 mL) was ice-cooled, and tetrahydro-2H-pyran-4-amine (20 mL) and sodium hydroxide (1.7 g) were added thereto. The reaction mixture was stirred at 60° C. overnight.

The reaction mixture was cooled to room temperature and then poured into water (320 mL), followed by stirring at room temperature for 1 hour. The resulting solid was collected by filtration, and the obtained solid was dried at 50° C. under reduced pressure. The obtained solid was added to a mixed solution of hexane (160 mL) and diisopropyl ether (16 mL), followed by stirring at 70° C. for 4 hours, then ice-cooling to room temperature, and stirring overnight. The solid was collected by filtration and dried at 50° C. under reduced pressure to obtain (1S)-1-(4-chloro-2-fluorophenyl)-2-(tetrahydro-2H-pyran-4-ylamino)ethanol (7.90 g) as a solid.

Preparation Example 3

Under a nitrogen atmosphere, a mixture of (1S)-1-(4-chloro-2-fluorophenyl)-2-(tetrahydro-2H-pyran-4-ylamino)ethanol (7.9 g) and acrylonitrile (34 mL) was stirred at 70° C. for 47 hours. The reaction mixture was cooled to room temperature and then concentrated under reduced pressure. The obtained residue was purified by silica gel column chromatography (hexane:ethyl acetate=6:4 to 0:10) to obtain 3-{[(2S)-2-(4-chloro-2-fluorophenyl)-2-hydroxyethyl](tetrahydro-2H-pyran-4-yl)amino}propanenitrile (9.38 g) as an oil.

Preparation Example 4

Under an argon atmosphere, to a mixture of 3-{[(2S)-2-(4-chloro-2-fluorophenyl)-2-hydroxyethyl](tetrahydro-2H-pyran-4-yl)amino}propanenitrile (9.38 g) and tetrahydrofuran (47 mL) was added diethyl chlorophosphate (4.33 mL) at −15° C. Then, to the reaction mixture was added dropwise lithium bis(trimethylsilyl)amide (1.1 M tetrahydrofuran solution, 60 mL) while keeping the temperature at −5° C. or lower. The reaction mixture was stirred at a temperature in the range from −7° C. to −15° C. for 1.5 hours, and then water (110 mL) was added thereto, followed by extracting with diisopropyl ether. The organic layer was washed with brine, then ice-cooled, and extracted with 3 M hydrochloric acid. The obtained aqueous layer was basified by the addition of a 50% aqueous sodium hydroxide solution, and extracted with diisopropyl ether. The organic layer was washed with brine, and then dried over anhydrous sodium sulfate. The insoluble materials were separated by filtration and the filtrate was concentrated under reduced pressure, 3-ambo-(3R, 4R)-4-(4-chloro-2-fluorophenyl)-1-(tetrahydro-2H-pyran-4-yl)pyrrolidine-3-carbonitrile (8.96 g) as an oil.

Preparation Example 5

Under a nitrogen atmosphere, to a solution of 3-ambo-(3R,4R)-4-(4-chloro-2-fluorophenyl)-1-(tetrahydro-2H-pyran-4-yl)pyrrolidine-3-carbonitrile (8.96 g) in ethanol (40 mL) was added a 50% aqueous sodium hydroxide solution (4.30 mL), followed by stirring at 100° C. for 5 hours. The reaction mixture was cooled to room temperature, and then ethanol (45 mL) and methanol (80 mL) were added thereto. The mixture was ice-cooled and concentrated sulfuric acid (2.20 mL) was added thereto. To the mixture were added anhydrous sodium sulfate and Celite, and then the insoluble materials were removed by filtration through Celite. The solid was washed with a mixed solution of ethanol:methanol (1:1) and the obtained filtrate was concentrated under reduced pressure. To the obtained residue was added 2-propanol (25 mL), followed by stirring at room temperature for 10 minutes, and tert-butylmethyl ether (80 mL) was added thereto. The mixture was stirred at 70° C. for 4 hours and then stirred at room temperature overnight. The resulting solid was collected by filtration, washed with a mixed solution of 2-propanol:tert-butylmethyl ether (1:3), and then dried at 50° C. under reduced pressure to obtain (3S,4R)-4-(4-chloro-2-fluorophenyl)-1-(tetrahydro-2H-pyran-4-yl)pyrrolidine-3-carboxylic acid (5.55 g) as a solid.

Preparation Example 6

Zinc powder (9 g) was dried with a heating gun for 15 minutes under reduced pressure and left to be cooled to room temperature. Then, N,N-dimethylformamide (50 mL) was added thereto under an argon atmosphere. Iodine (250 mg) was added thereto at room temperature, followed by stirring, and then to the reaction mixture were added iodine (250 mg) and methyl N-(tert-butoxycarbonyl)-3-iodo-L-alaninate (15.5 g) at room temperature, followed by stirring for 35 minutes. To the reaction mixture were added tris(dibenzylideneacetone)dipalladium (0) (2.2 g), 2-dicyclohexylphosphino-2',6'-dimethoxybiphenyl (2.0 g), and 1-bromo-2-fluoro-4-methylbenzene (9 mL) at room temperature, followed by stirring at 60° C. for 18 hours. To the reaction mixture was added a saturated aqueous ammonium chloride solution, followed by filtering through Celite. The filtrate was extracted with ethyl acetate and the organic layer was washed with brine. The organic layer was dried over anhydrous magnesium sulfate, the insoluble materials were then separated by filtration, and the filtrate was concentrated under reduced pressure. The obtained residue was purified by silica gel column chromatography (hexane:ethyl acetate=97:3 to 83:17), and then purified by basic silica gel column chromatography (hexane:ethyl acetate=97:3 to 83:17) to obtain methyl N-(tert-butoxycarbonyl)-2-fluoro-4-methyl-L-phenylalaninate (10 g) as a solid.

Preparation Example 7

To a solution of methyl N-(tert-butoxycarbonyl)-2-fluoro-4-methyl-L-phenylalaninate (10 g) in dioxane (10 mL) was added hydrogen chloride (4 M solution in dioxane, 100 mL) at room temperature, followed by stirring for 1.5 hours. The solvent was evaporated under reduced pressure and the resulting solid was suspended in N,N-dimethylformamide (100 mL). To the suspension were added N-[(2-nitrophenyl)sulfonyl]-L-alanine (9.69 g) and O-(7-aza-1H-benzotriazol-1-yl)-N,N,N',N'-tetramethyluronium hexafluorophosphate (13.4 g) at room temperature, and then N,N-diisopropyl ethylamine (18 mL) was added thereto at room temperature, followed by stirring for 3 hours. To the reaction mixture was added a saturated aqueous sodium hydrogen carbonate solution, followed by extracting with ethyl acetate. The organic layer was washed with brine. The organic layer was dried over anhydrous magnesium sulfate, the insoluble materials

Preparation Example 8

To a solution of methyl N-[(2-nitrophenyl)sulfonyl]-L-alanyl-2-fluoro-4-methyl-L-phenylalaninate (13.6 g) in N,N-dimethylformamide (100 mL) were added 1,2-dibromoethane (20 mL) and potassium carbonate (32.1 g) at room temperature, followed by stirring at 60° C. overnight. The reaction mixture was filtered and the filtrate was concentrated under reduced pressure. To the residue were added ethyl acetate and water, and the organic layer was washed with brine. The organic layer was dried over anhydrous magnesium sulfate, the insoluble materials were then separated by filtration, and the filtrate was concentrated under reduced pressure. The obtained residue was purified by silica gel column chromatography (chloroform:methanol=100:0 to 95:5) to obtain a solid. The obtained solid was triturated with toluene to obtain methyl (2S)-3-(2-fluoro-4-methylphenyl)-2-{(3S)-3-methyl-4-[(2-nitrophenyl)sulfonyl]-2-oxopiperazin-1-yl}propanoate (13.6 g) as a solid.

Preparation Example 9

To a solution of methyl (2S)-3-(2-fluoro-4-methylphenyl)-2-{(3S)-3-methyl-4-[(2-nitrophenyl)sulfonyl]-2-oxopiperazin-1-yl}propanoate (13.6 g) in tetrahydrofuran (200 mL) was added a borane-tetrahydrofuran complex (0.85 M tetrahydrofuran solution, 26 mL) at −14° C. or lower for 20 minutes under a nitrogen atmosphere, followed by stirring 0° C. for 1 hour. The reaction mixture was warmed to room temperature and stirred at room temperature overnight. The reaction mixture was poured into a saturated aqueous sodium hydrogen carbonate solution, followed by extracting with ethyl acetate. The organic layer was washed with brine. The organic layer was dried over anhydrous magnesium sulfate, the insoluble materials were then separated by filtration, and the filtrate was concentrated under reduced pressure. The obtained residue was purified by silica gel column chromatography (hexane:ethyl acetate=90:10 to 50:50) to obtain methyl (2S)-3-(2-fluoro-4-methylphenyl)-2-{(3S)-3-methyl-4-[(2-nitrophenyl)sulfonyl]piperazin-1-yl}propanoate (8.45 g) as a solid.

Preparation Example 10

To a solution of methyl (2S)-3-(2-fluoro-4-methylphenyl)-2-{(3S)-3-methyl-4-[(2-nitrophenyl)sulfonyl]piperazin-1-yl}propanoate (8.45 g) in N,N-dimethylformamide (100 mL) were added potassium carbonate (4.87 g) and 4-tert-butylbenzenethiol (4.74 mL), followed by stirring overnight. The reaction mixture was concentrated under reduced pressure, and to the obtained residue were added ethyl acetate and 1 M hydrochloric acid, followed by stirring. The aqueous layer was washed with ethyl acetate and adjusted to pH=8 by the addition of sodium hydroxide. The mixture was extracted with chloroform, the organic layer was then dried over anhydrous sodium sulfate, the insoluble materials were then separated by filtration, and the filtrate was concentrated under reduced pressure. The obtained residue was diluted with ethyl acetate, and hydrogen chloride (4 M solution in ethyl acetate, 9.25 mL) was added thereto, followed by stirring. The precipitated solid was filtered to obtain methyl (2S)-3-(2-fluoro-4-methylphenyl)-2-[(3S)-3-methylpiperazin-1-yl]propanoate dihydrochloride (6.02 g) as a solid.

Preparation Example 11

To a solution of (3S,4R)-4-(4-chloro-2-fluorophenyl)-1-(tetrahydro-2H-pyran-4-yl)pyrrolidine-3-carboxylic acid (1.35 g) in N,N-dimethylformamide (20 mL) were added methyl (2S)-3-(2-fluoro-4-methylphenyl)-2-[(3S)-3-methylpiperazin-1-yl]propanoate dihydrochloride (1.47 g) and O-(7-aza-1H-benzotriazol-1-yl)-N,N,N',N'-tetramethyluronium hexafluorophosphate (1.72 g) under ice-cooling, followed by stirring, and then N,N-diisopropyl ethylamine (3.0 mL) was added thereto, followed by stirring for 1.5 hours under ice-cooling. The reaction mixture was poured into a saturated aqueous sodium hydrogen carbonate solution, followed by extracting with ethyl acetate. The organic layer was washed with brine. The organic layer was dried over anhydrous magnesium sulfate, the insoluble materials were then separated by filtration, and the filtrate was concentrated under reduced pressure. The obtained residue was purified by silica gel column chromatography (chloroform:methanol=100:0 to 95:5) to obtain methyl (2S)-2-[(3S)-4-{[(3S,4R)-4-(4-chloro-2-fluorophenyl)-1-(tetrahydro-2H-pyran-4-yl)pyrrolidin-3-yl]carbonyl}-3-methylpiperazin-1-yl]-3-(2-fluoro-4-methylphenyl)propanoate (2.28 g) as a solid.

Preparation Example 12

To a solution of (2-fluoro-4,6-dimethylphenyl) methanol (2 g) in dichloromethane (20 mL) was added phosphorus tribromide (1.28 mL) under ice-cooling. The reaction mixture was stirred at room temperature for 1 hour. To the reaction mixture were added a saturated aqueous sodium hydrogen carbonate solution. The mixture was extracted with dichloromethane and the organic layer was washed with a saturated aqueous sodium hydrogen carbonate solution. The organic layer was washed with brine and dried over anhydrous magnesium sulfate. The insoluble materials were separated by filtration and the filtrate was concentrated under reduced pressure to obtain 2-(bromomethyl)-1-fluoro-3,5-dimethylbenzene (2.52 g) as an oil.

Preparation Example 13

To a suspension of tert-butyl N-(diphenylmethylidene)glycinate (3.43 g) in toluene (25 mL) was added a solution of 2-(bromomethyl)-1-fluoro-3,5-dimethylbenzene (2.52 g), (R)-4,4-dibutyl-2,6-bis(3,4,5-trifluorophenyl)-4,5-dihydro-3H-dinaphtho[2,1-c:1',2'-e]azepinium bromide (44 mg), and potassium hydroxide (12.5 g) in water (25 mL) under ice-cooling. The reaction mixture was stirred at 0° C. for 4 days. To the reaction mixture was added water. The mixture was extracted with diethyl ether and the organic layer was washed with brine. The organic layer was dried over anhydrous magnesium sulfate. The insoluble materials were separated by filtration and the filtrate was concentrated under reduced pressure to obtain tert-butyl N-(diphenylmethylidene)-2-fluoro-4,6-dimethyl-L-phenylalaninate (5.91 g) as an oil.

Preparation Example 14

To a mixture of tert-butyl N-(diphenylmethylidene)-2-fluoro-4,6-dimethyl-L-phenylalaninate (5.91 g), tetrahydrofuran (60 mL), and water (30 mL) was added citric acid (10.9 g) at room temperature. The reaction mixture was stirred at room temperature for 1 hour. To the reaction mixture was added diisopropyl ether, water was added thereto, and the aqueous layer was separated. The aqueous layer was washed with diisopropyl ether, and potassium carbonate was added thereto. The aqueous layer was extracted with ethyl acetate and the organic layer was washed with brine. The organic layer was dried over anhydrous magnesium sulfate. The insoluble materials were separated by filtration and the filtrate was concentrated under reduced pressure to obtain tert-butyl 2-fluoro-4,6-dimethyl-L-phenylalaninate (3.1 g) as an oil.

Preparation Example 15

To a solution of tert-butyl 2-fluoro-4,6-dimethyl-L-phenylalaninate (3.1 g) in N,N-dimethylformamide (47 mL) were added for N-[(2-nitrophenyl)sulfonyl]-L-alanine (3.3 g), O-(7-aza-1H-benzotriazol-1-yl)-N,N,N',N'-tetramethyluronium hexafluorophosphate (5.7 g), and N,N-diisopropyl ethylamine (6 mL) at room temperature. The reaction mixture was stirred at room temperature for 1 day. To the reaction mixture was added water. The aqueous layer was extracted with ethyl acetate and the organic layer was washed with a saturated aqueous sodium hydrogen carbonate solution. The organic layer was washed with brine and dried over anhydrous magnesium sulfate. The insoluble materials were separated by filtration and the filtrate was concentrated under reduced pressure to obtain tert-butyl N-[(2-nitrophenyl) sulfonyl]-L-alanyl-2-fluoro-4, 6-dimethyl-L-phenylalaninate (7.78 g) as an oil.

Preparation Example 16

To a solution of methyl (2S)-3-mesityl-2-{(3S)-3-methyl-4-[(2-nitrophenyl)sulfonyl]piperazin-1-yl}propanoate (28.9 g) in N,N-dimethylformamide (185 mL) were added potassium carbonate (16.3 g) and 4-tert-butylbenzenethiol (16 mL) under ice-cooling. The reaction mixture was stirred at room temperature for 1 day. To the reaction mixture was added water, ethyl acetate was added thereto, and the organic layer was separated. The organic layer was extracted with 1 M hydrochloric acid, and to the aqueous layer was added potassium carbonate. The aqueous layer was extracted with ethyl acetate. The organic layer was sequentially washed with water and brine, and then dried over anhydrous magnesium sulfate. The insoluble materials were separated by filtration and the filtrate was concentrated under reduced pressure to obtain methyl (2S)-3-mesityl-2-[(3S)-3-methylpiperazin-1-yl]propanoate (16.9 g) as an oil.

Preparation Example 17

To a solution of methyl 2,4,6-trimethyl-L-phenylalaninate hydrochloride (47.8 g) in N,N-dimethylformamide (717 mL) were added for N-[(2-nitrophenyl)sulfonyl]-L-alanine (51.4 g), 1-(3-dimethylaminopropyl)-3-ethylcarbodiimide hydrochloride (42.7 g), 1-hydroxybenzotriazole (30.1 g), and triethylamine (77.5 mL) at 10° C. The reaction mixture was stirred at room temperature for 2 hours. To the reaction mixture was added water. The aqueous layer was extracted with ethyl acetate and the organic layer was washed with water. The organic layer was washed with brine and the organic layer was dried over anhydrous magnesium sulfate. The insoluble materials were separated by filtration and the filtrate was concentrated under reduced pressure to obtain methyl N-[(2-nitrophenyl)sulfonyl]-L-alanyl-2,4,6-trimethyl-L-phenylalaninate (74.8 g) as an oil.

Preparation Example 18

To a solution of tert-butyl (2S)-3-(2,3-dihydro-1H-inden-5-yl)-2-[(diphenylmethylidene)amino]propanoate (971 mg) in tetrahydrofuran (11.7 mL) was added a solution of citric acid (2.19 g) in water (5.8 mL) at room temperature. The reaction mixture was stirred at room temperature for 6 hours. To the reaction mixture was added diethyl ether, and the aqueous layer was separated. To the aqueous layer was added potassium carbonate under ice-cooling and the aqueous layer was extracted with chloroform. The organic layer was dried over anhydrous magnesium sulfate. The insoluble materials were separated by filtration and the filtrate was concentrated under reduced pressure. To the obtained residue were added dioxane (10 mL) and hydrogen chloride (4 M solution in dioxane, 0.7 mL), followed by stirring at room temperature. The precipitated solid was collected by filtration, then washed with dioxane, and dried under reduced pressure. The solid was washed with acetonitrile and dried under reduced pressure to obtain tert-butyl (2S)-2-amino-3-(2,3-dihydro-1H-inden-5-yl)propanoate monohydrochloride (251 mg) as a solid.

Preparation Example 19

To a mixture of methyl (2S)-3-(4-bromophenyl)-2-{(3S)-3-methyl-4-[(2-nitrophenyl)sulfonyl]-2-oxopiperazin-1-yl}propanoate (500 mg), toluene (10 mL), and water (0.25 mL) were added cyclopropylboronic acid (397 mg), tripotassium phosphate (982 mg), palladium (II) acetate (41.5 mg), and 2-dicyclohexylphosphino-2',6'-dimethoxybiphenyl (152 mg) at room temperature. The reaction mixture was warmed to 90° C. under an argon atmosphere and stirred for 15 hours. The reaction mixture was filtered through Celite and the filtrate was concentrated under reduced pressure. The obtained residue was purified by silica gel column chromatography (hexane:ethyl acetate=5:1 to 3:2) to obtain methyl (2S)-3-(4-cyclopropylphenyl)-2-{(3S)-3-methyl-4-[(2-nitrophenyl)sulfonyl]-2-oxopiperazin-1-yl}propanoate (196 mg) as an oil.

Preparation Example 20

A mixture of methyl (2R)-2-bromo-3-(2-naphthyl)propanoate (500 mg), cis-2,6-dimethylpiperazine (1.90 g), and N,N-dimethylformamide (10 mL) was stirred at room temperature overnight. To the reaction mixture was added water, followed by extracting with ethyl acetate. The organic layer was washed with brine and then concentrated under reduced pressure. The obtained residue was purified by silica gel column chromatography (chloroform:methanol=98:2 to 90:10) to obtain methyl (2S)-2-[(3R,5S)-3,5-dimethylpiperazin-1-yl]-3-(2-naphthyl)propanoate (107 mg) as an oil.

Preparation Example 21

A mixture of tert-butyl (3R)-4-(2-methoxy-2-oxoethyl)-3-methylpiperazine-1-carboxylate (818 mg) and tetrahydrofuran (8.00 mL) was cooled to −78° C. To the reaction mixture was added potassium bis(trimethylsilyl)amide (1 M tetrahydrofuran solution, 6.00 mL) at −78° C., followed by stirring at the same temperature for 40 minutes. To the reaction mixture was added 4-(bromomethyl)-1,2-dichlorobenzene (2.15 g) at −78° C., followed by stirring at the same temperature for 30 minutes. Thereafter, the mixture was warmed to room temperature for 30 minutes, and subsequently stirred at room temperature for 2 hours. To the reaction mixture was added an aqueous ammonium chloride solution, followed by extracting with ethyl acetate. The organic layer was dried over anhydrous magnesium sulfate, the insoluble materials were then separated by filtration, and the filtrate was concentrated under reduced pressure. The obtained residue was purified by silica gel column chromatography (hexane:ethyl acetate=85:15) to obtain tert-butyl (3R)-4-[3-(3,4-dichlorophenyl)-1-methoxy-1-oxopropan-2-yl]-3-methylpiperazine-1-carboxylate (267 mg, Preparation Example 21, the earlier eluted fraction) as an oil. Further, a single isomer having a different steric configuration at the α-position of the ester group (70.0 mg, Preparation Example 335, the later eluted fraction) was obtained as an oil.

Preparation Example 22

To a solution of tert-butyl (3R)-4-[3-(3,4-dichlorophenyl)-1-methoxy-1-oxopropan-2-yl]-3-methylpiperazine-1-carboxylate (246 mg, Preparation Example 21, the earlier eluted fraction) in dioxane (984 μL) was added hydrogen chloride (4 M solution in dioxane, 712 μL) under ice-cooling, followed by stirring at room temperature overnight. To the reaction mixture was added a saturated aqueous sodium hydrogen carbonate solution, followed by extracting with ethyl acetate. The organic layer was dried over anhydrous magnesium sulfate, the insoluble materials were then separated by filtration, and the filtrate was concentrated under reduced pressure. The obtained residue was purified by silica gel column chromatography (chloroform:methanol=95:5) to obtain methyl 3-(3,4-dichlorophenyl)-2-[(2R)-2-methylpiperazin-1-yl]propanoate (153 mg) as a solid.

Preparation Example 23

A mixture of methyl (2S)-3-(4-bromophenyl)-2-{(3S)-3-methyl-4-[(2-nitrophenyl)sulfonyl]piperazin-1-yl}propanoate (484 mg), zinc cyanide (550 mg), bis(tri-tert-butylphosphine)palladium (0) (180 mg), zinc powder (15 mg), and N,N-dimethylacetamide (10 mL) was stirred at 90° C. for 2 hours under an argon atmosphere. The reaction mixture was warmed to 130° C., and heated and stirred for 5.5 hours. The reaction mixture was left to be cooled to room temperature and then water was added thereto, followed by extracting with ethyl acetate. The organic layer was washed with brine and then concentrated under reduced pressure. The obtained residue was purified by silica gel column chromatography (hexane:ethyl acetate=80:20 to 40:60) to obtain methyl (2S)-3-(4-cyanophenyl)-2-{(3S)-3-methyl-4-[(2-nitrophenyl)sulfonyl]piperazin-1-yl}propanoate (88 mg) as an oil.

Preparation Example 24

To a mixture of methyl (2S)-2-[(3S)-3-(2-aminoethyl)-4-{[(3S,4R)-4-(2,4-difluorophenyl)-1-(1-methyl-6-oxo-1,6-dihydropyridazin-3-yl)pyrrolidin-3-yl]carbonyl}piperazin-1-yl]-3-(2-naphthyl)propanoate dihydrochloride (210 mg), formaldehyde (a 37% aqueous solution, 140 mg), and dichloromethane (6.00 mL) was added sodium triacetoxyborohydride (184 mg) at room temperature, followed by stirring at room temperature for 12 hours. To the reaction mixture was added a saturated aqueous sodium hydrogen carbonate solution, followed by extracting with chloroform. The organic layer was washed with brine and dried over anhydrous magnesium sulfate, the insoluble materials were then separated by filtration, and the filtrate was concentrated under reduced pressure. The obtained residue was purified by silica gel column chromatography (chloroform:methanol=99:1) to obtain methyl (2S)-2-{(3S)-4-{[(3S,4R)-4-(2,4-difluorophenyl)-1-(1-methyl-6-oxo-1,6-dihydropyridazin-3-yl)pyrrolidin-3-yl]carbonyl}-3-[2-(dimethylamino)ethyl]piperazin-1-yl}-3-(2-naphthyl)propanoate (82.0 mg) as an oil.

Preparation Example 25

To a solution of methyl (3S,4R)-4-(2,4-difluorophenyl)pyrrolidine-3-carboxylic acid (275 mg) in dioxane (3.0 mL) were added 2-chloro-5-(difluoromethyl)pyridine (225 mg), tris(dibenzylideneacetone)dipalladium (0) (21 mg), 2-dicyclohexylphosphino-2',6'-diisopropoxy-1,1'-biphenyl (22 mg), and sodium tert-butoxide (275 mg) under an argon atmosphere. The reaction mixture was stirred at 100° C. overnight and left to be cooled to room temperature, and then water was added thereto, followed by extracting with ethyl acetate. The organic layer was washed with brine and dried over anhydrous magnesium sulfate, the insoluble materials were then separated by filtration, and the filtrate was concentrated under reduced pressure. The obtained residue was purified by silica gel column chromatography (chloroform:methanol=10:0 to 9:1) to obtain (3S,4R)-1-[5-(difluoromethyl)pyridin-2-yl]-4-(2,4-difluorophenyl)pyrrolidine-3-carboxylic acid (118 mg) as a solid.

Preparation Example 26

To a solution of methyl (3S,4R)-4-(2,4-difluorophenyl)-1-[(2-nitrophenyl)sulfonyl]pyrrolidine-3-carboxylate (2.80 g) in tetrahydrofuran (25 mL)-water (6 mL) was added lithium hydroxide monohydrate (554 mg), followed by stirring at room temperature overnight. To the reaction mixture was added 1 M hydrochloric acid (14.0 mL) under ice-cooling, followed by extracting with ethyl acetate. The organic layer was washed with brine and dried over anhydrous magnesium sulfate. The insoluble materials were separated by filtration and the filtrate was concentrated under reduced pressure to obtain (3S,4R)-4-(2,4-difluorophenyl)-1-[(2-nitrophenyl)sulfonyl]pyrrolidine-3-carboxylic acid (2.69 g) as a solid.

Preparation Example 27

A mixture of tert-butyl (2S)-2-[(3R)-4-{[(3S,4R)-4-(2,4-difluorophenyl)pyrrolidin-3-yl]carbonyl}-3-(methoxymethyl)piperazin-1-yl]-3-(2,3-dihydro-1H-inden-5-yl)propanoate (90 mg), 1-bromo-4-fluorobenzene (33 μL), tris(dibenzylideneacetone)dipalladium (0) (5 mg), 2-dicyclohexylphosphino-2',6'-diisopropoxy-1,1'-biphenyl (5 mg), sodium tert-butoxide (37 mg), and dioxane (2 mL) was stirred at 100° C. overnight under an argon atmosphere. The reaction mixture was left to be cooled to room temperature, and then water was added thereto, followed by extracting with ethyl acetate. The organic layer was washed with brine and dried over anhydrous magnesium sulfate, the insoluble materials were then separated by filtration, and the filtrate was concentrated under reduced pressure. The obtained residue was purified by silica gel column chromatography (hexane:ethyl acetate=9:1 to 1:1) to obtain tert-butyl (2S)-2-[(3R)-4-{[(3S,4R)-4-(2,4-difluorophenyl)-1-(4-fluorophenyl)pyrrolidin-3-yl]carbonyl}-3-

(methoxymethyl)piperazin-1-yl]-3-(2,3-dihydro-1H-inden-5-yl)propanoate (68 mg) as a solid.

Preparation Example 28

A mixture of methyl 2-bromo-1,3-thiazole (555 mg), (3S,4R)-4-(2,4-difluorophenyl)pyrrolidine-3-carboxylate (400 mg), potassium carbonate (459 mg), and N,N-dimethylformamide (5 mL) was stirred at 100° C. for 2 days. To the reaction mixture was added water at room temperature, followed by extracting with ethyl acetate. The organic layer was washed with brine and then dried over anhydrous magnesium sulfate, the insoluble materials were then separated by filtration, and the filtrate was concentrated under reduced pressure. The obtained residue was purified by silica gel column chromatography (hexane:ethyl acetate=90:10 to 50:50) to obtain methyl (3S,4R)-4-(2,4-difluorophenyl)-1-(1,3-thiazol-2-yl)pyrrolidine-3-carboxylate (171 mg) as an oil.

Preparation Example 29

To a solution of tert-butyl 3-(4,4-dimethylcyclohex-1-en-1-yl)-L-alaninate (2.68 g) in ethanol (53.0 mL) was added 10% palladium hydroxide on carbon (540 mg) at room temperature under a nitrogen atmosphere. The reaction mixture was stirred at room temperature for 5 hours under a hydrogen atmosphere, and to the reaction mixture was added Celite, followed by stirring at room temperature for 15 minutes. The reaction mixture was filtered through Celite and the filtrate was concentrated under reduced pressure. To the residue were added ethanol (53.0 mL) and 10% palladium hydroxide on carbon (540 mg) at room temperature under a nitrogen atmosphere. The reaction mixture was stirred at room temperature for 15 hours under a hydrogen atmosphere of 3 atm. The reaction mixture was filtered through Celite and the filtrate was concentrated under reduced pressure to obtain tert-butyl 3-(4,4-dimethylcyclohexyl)-L-alaninate monohydrochloride (2.67 g) as a solid.

Preparation Example 30

To a solution of tert-butyl (2S)-2-[(3S)-4-{[(3S,4R)-4-(2,4-difluorophenyl)pyrrolidin-3-yl]carbonyl}-3-methylpiperazin-1-yl]-3-(2,3-dihydro-1H-inden-5-yl)propanoate (70.0 mg) in tetrahydrofuran (1.40 mL) were added triethylamine (53 μL) and cyclopropanecarbonyl chloride (18 μL) under ice-cooling. The reaction mixture was warmed to room temperature and stirred for 1 hour. To the reaction mixture was added a saturated aqueous sodium hydrogen carbonate solution under ice-cooling, followed by extracting with ethyl acetate. The organic layer was washed with brine and dried over anhydrous magnesium sulfate, the insoluble materials were then separated by filtration, and the filtrate was concentrated under reduced pressure. The obtained residue was purified by silica gel column chromatography (chloroform:methanol=10:0 to 9:1) to obtain tert-butyl (2S)-2-[(3S)-4-{[(3S,4R)-1-(cyclopropylcarbonyl)-4-(2,4-difluorophenyl)pyrrolidin-3-yl]carbonyl}-3-methylpiperazin-1-yl]-3-(2,3-dihydro-1H-inden-5-yl)propanoate (70.0 mg) as an oil.

Preparation Example 31

To a suspension of 3-cyclopropyl-L-alanine (2 g) in tetrahydrofuran (5 mL)-water (17 mL) were added triethylamine (7 mL) and 2-nitrobenzenesulfonyl chloride (4.4 g) under ice-cooling. The reaction mixture was warmed to room temperature and stirred for 22.5 hours. The reaction mixture was ice-cooled and adjusted to approximately pH 1 by the addition of concentrated hydrochloric acid, and then water was added thereto, followed by extracting with ethyl acetate. The organic layer was then dried over anhydrous sodium sulfate, the insoluble materials were then separated by filtration, and the filtrate was concentrated under reduced pressure. The obtained residue was purified by silica gel column chromatography (chloroform:methanol=10:0 to 9:1) to obtain 3-cyclopropyl-N-[(2-nitrophenyl)sulfonyl]-L-alanine (4.75 g) as a solid.

Preparation Example 32

To a suspension of 4-tert-butyl-L-phenylalanine (1.00 g) in tert-butyl acetate (13 mL) was added hydrochloric acid (0.62 mL) under ice-cooling. The reaction mixture was stirred at room temperature for 15 hours. To the reaction mixture was added a 1 M aqueous sodium hydroxide solution (6.00 mL) under ice-cooling, and a saturated aqueous sodium hydrogen carbonate solution was added thereto. The mixture was extracted with ethyl acetate and the organic layer was washed with brine. The organic layer was dried over anhydrous magnesium sulfate. The insoluble materials were separated by filtration and the filtrate was concentrated under reduced pressure to obtain tert-butyl 4-tert-butyl-L-phenylalaninate (1.17 g) as an oil.

Preparation Example 33

To a mixed solution of tetrahydrofuran (1.70 mL)-water (550 μL) were added methyl 1-tert-butyl-4-(2-fluoro-4-methylphenyl)pyrrolidine-3-carboxylate (138 mg, Preparation Example 350) and lithium hydroxide monohydrate (43 mg) at room temperature, followed by stirring at room temperature overnight. To the reaction mixture was added 1 M hydrochloric acid (1.1 mL) at room temperature, and then the reaction mixture was concentrated under reduced pressure. A mixture of the obtained residue, N,N-dimethylformamide (2 mL), N,N-diisopropyl ethylamine (322 μL), tert-butyl (2S)-3-(2,3-dihydro-1H-inden-5-yl)-2-[(3S)-3-methylpiperazin-1-yl]propanoate dihydrochloride (216 mg), and O-(7-aza-1H-benzotriazol-1-yl)-N,N,N',N'-tetramethyluronium hexafluorophosphate (233 mg) was stirred at room temperature overnight. To the reaction mixture were added O-(7-aza-1H-benzotriazol-1-yl)-N,N,N',N'-tetramethyluronium hexafluorophosphate (44 mg), tert-butyl (2S)-3-(2,3-dihydro-1H-inden-5-yl)-2-[(3S)-3-methylpiperazin-1-yl]propanoate dihydrochloride (50 mg), and N,N-diisopropyl ethylamine (161 μL), followed by stirring at room temperature for 1 hour. To the reaction mixture was added water, followed by extracting with ethyl acetate, and the organic layer was washed with brine. The organic layer was dried over anhydrous magnesium sulfate, the insoluble materials were then separated by filtration, and the filtrate was concentrated under reduced pressure. The obtained residue was purified by silica gel column chromatography (chloroform:methanol=10:0 to 9:1) to obtain tert-butyl (2S)-2-[(3S)-4-{[1-tert-butyl-4-(2-fluoro-4-methylphenyl)pyrrolidin-3-yl]carbonyl}-3-methylpiperazin-1-yl]-3-(2,3-dihydro-1H-inden-5-yl)propanoate (102 mg) as a solid.

Preparation Example 34

To an ice-cooled mixture of diethyl {2-[(4S)-4-benzyl-2-oxo-1,3-oxazolidin-3-yl]-2-oxoethyl}phosphonate (2.10 g), lithium chloride (315 mg), and acetonitrile (42.0 mL) was added N,N-diisopropyl ethylamine (1.20 mL), followed by stirring at the same temperature for 10 minutes. To the reaction mixture was added 5-chloro-2-pyridine carboxyaldehyde (840 mg), followed by warming to room temperature and stirring overnight. The reaction mixture was poured into water, followed by stirring at room temperature for 1 hour. The resulting solid was collected by filtration and washed with water. The obtained solid was dried at 60° C. under reduced pressure to obtain (4S)-4-benzyl-3-[(2E)-3-(5-chloropyridin-2-yl)prop-2-enoyl]-1,3-oxazolidin-2-one (1.65 g) as a solid.

Preparation Example 35

To a solution of (4S)-4-benzyl-3-{[1-tert-butyl-4-(5-chloropyridin-2-yl)pyrrolidin-3-yl]carbonyl}-1,3-oxazolidin-2-one (925 mg, Preparation Example 356) in methanol (15.0 mL) was added samarium trifluoromethanesulfonate (III) (100 mg), followed by stirring at room temperature overnight. The reaction mixture was concentrated under reduced pressure. The obtained residue was purified by basic silica gel column chromatography (chloroform alone) to obtain methyl 1-tert-butyl-4-(5-chloropyridin-2-yl)pyrrolidine-3-carboxylate (504 mg) as an oil.

Preparation Example 36

To a mixture of methyl 1-tert-butyl-4-(5-chloropyridin-2-yl)pyrrolidine-3-carboxylate (500 mg, Preparation Example 35) and dioxane (6.00 mL) was added concentrated hydrochloric acid (6.00 mL) at room temperature. The reaction mixture was stirred at 60° C. for 6 hours. The reaction mixture was left to be cooled to room temperature and then concentrated under reduced pressure. To the obtained residue was added toluene, followed by concentrating under reduced pressure. The obtained residue was dissolved in 2-propanol and diluted in diisopropyl ether. The mixture was stirred at room temperature for 1 hour and the resulting solid was collected by filtration. The obtained solid was dried at 50° C. under reduced pressure to obtain 1-tert-butyl-4-(5-chloropyridin-2-yl)pyrrolidine-3-carboxylic acid monohydrochloride (493 mg) as a solid.

Preparation Example 37

To a suspension of (2E)-3-(4-methoxyphenyl)acrylic acid (2.00 g) in dichloromethane (35 mL) was added N,N-dimethylformamide (40 µL) at room temperature. Under an argon atmosphere, to the ice-cooled reaction mixture was added dropwise a solution of oxalyl chloride (2 mL) in dichloromethane (10 mL) over approximately 10 minutes. The reaction mixture was warmed to room temperature and stirred overnight. The reaction mixture was concentrated under reduced pressure and the obtained residue was dissolved in dichloromethane (10 mL). This solution was added dropwise to an ice-cooled suspension of (4S)-4-benzyl-1,3-oxazolidin-2-one (2 g) and lithium chloride (2.4 g) in triethylamine (8 mL) and dichloromethane (35 mL) for 10 minutes under an argon atmosphere. The reaction mixture was warmed to room temperature and stirred overnight. To the reaction mixture was added a 5% aqueous citric acid solution, and the aqueous layer and the organic layer were separated. The aqueous layer was extracted with chloroform, and the combined organic layer was washed with brine and then dried over anhydrous sodium sulfate. The insoluble materials were then separated by filtration and the filtrate was concentrated under reduced pressure. The obtained residue was purified by silica gel column chromatography (chloroform:methanol=100:0 to 95:5) to obtain (4S)-4-benzyl-3-[(2E)-3-(4-methoxyphenyl)prop-2-enoyl]-1,3-oxazolidin-2-one (2.93 g) as a solid.

Preparation Example 38

To a solution of (4S)-4-benzyl-3-[(2E)-3-(4-methoxyphenyl)prop-2-enoyl]-1,3-oxazolidin-2-one (400 mg) in dichloromethane (4 mL) was added trifluoroacetate (100 µL) at room temperature, and then a solution of N-(methoxymethyl)-2-methyl-N-[(trimethylsilyl)methyl]propane-2-amine (500 mg) in dichloromethane (2 mL) was added thereto, followed by stirring for 3 days. To the reaction mixture was added a solution of N-(methoxymethyl)-2-methyl-N-[(trimethylsilyl)methyl]propane-2-amine (200 mg) in dichloromethane (2 mL), followed by stirring overnight. To the reaction mixture were added chloroform and a saturated aqueous sodium hydrogen carbonate solution, and the aqueous layer and the organic layer was separated. The aqueous layer was extracted with chloroform, the combined organic layer was then dried over anhydrous sodium sulfate, the insoluble materials were then separated by filtration, and the filtrate was concentrated under reduced pressure. The obtained residue was purified by silica gel column chromatography (chloroform:methanol=10:0 to 9:1) to obtain (4S)-4-benzyl-3-{[1-tert-butyl-4-(4-methoxyphenyl)pyrrolidin-3-yl]carbonyl}-1,3-oxazolidin-2-one (225 mg, the earlier eluted fraction) as a solid. Further, a single isomer having a different steric configuration at the 3- and 4-positions of the pyrrolidine group (235 mg, Preparation Example 38, the later eluted fraction) was obtained as a solid.

Preparation Example 39

To a solution of (4S)-4-benzyl-3-{[1-tert-butyl-4-(4-methoxyphenyl)pyrrolidin-3-yl]carbonyl}-1,3-oxazolidin-2-one (231 mg, Preparation Example 38, the later eluted fraction) in tetrahydrofuran (3 mL)-water (1 mL) was added lithium hydroxide monohydrate (46 mg) under ice-cooling. The reaction mixture was warmed to room temperature, followed by stirring for 2 days. The reaction mixture was diluted with water, ethyl acetate was added thereto, and the aqueous layer and the organic layer were separated. To the aqueous layer was added 1 M hydrochloric acid (1.1 mL), the aqueous layer was then concentrated under reduced pressure. To the residue was added ethanol, and the mixture was concentrated in vacuo to obtain 1-tert-butyl-4-(4-methoxyphenyl)pyrrolidine-3-carboxylic acid (252 mg) as a solid.

Preparation Example 40

To a mixture of tert-butyl (2S)-3-(2,3-dihydro-1H-inden-5-yl)-2-[(3S)-3-methylpiperazin-1-yl]propanoate (30.9 g) and ethyl acetate (200 mL) was added hydrogen chloride (4 M solution in dioxane, 46.0 mL) under ice-cooling. The reaction mixture was warmed to room temperature and stirred for 2 hours. The resulting solid was filtered to obtain tert-butyl (2S)-3-(2,3-dihydro-1H-inden-5-yl)-2-[(3S)-3-methylpiperazin-1-yl]propanoate dihydrochloride (37.4 g) as a solid.

Preparation Example 41

To a solution of diethyl {2-[(4S)-4-benzyl-2-oxo-1,3-oxazolidin-3-yl]-2-oxoethyl}phosphonate (548 mg) in tetrahydrofuran (10 mL) was added sodium hydride (55% oil dispersion, 69 mg) under ice-cooling, followed by stirring at the same temperature for 10 minutes. To the reaction mixture was added 3-fluoro-4-formyl benzonitrile (209 mg) at the same temperature, followed by warming to room temperature and stirring for 1 hour. To the reaction mixture were added ethyl acetate and water, and the organic layer was separated and washed with brine. The organic layer was dried over anhydrous magnesium sulfate, the insoluble materials were then separated by filtration, and the filtrate was concentrated under reduced pressure. The obtained residue was purified by silica gel column chromatography (chloroform:methanol=100:0 to 95:5) to obtain 4-{(1E)-3-[(4S)-4-benzyl-2-oxo-1,3-oxazolidin-3-yl]-3-oxoprop-1-en-1-yl}-3-fluorobenzonitrile (387 mg) as a solid.

Preparation Example 42

To a solution of 4-chloro-2-methyl-L-phenylalanine (1.00 g) in methanol (10.0 mL) was added thionyl chloride (500 µL) under ice-cooling. The reaction mixture was stirred at 60° C. for 4 hours. The reaction mixture was left to be cooled to room temperature and then concentrated under reduced pressure. To the obtained residue was added diethyl ether, and the solid was collected by filtration to obtain methyl 4-chloro-2-methyl-L-phenylalaninate monohydrochloride (1.05 g) as a solid.

Preparation Example 43

To a solution of 1-(bromomethyl)-2,3-difluoro-4-methylbenzene (1 g) in toluene (10 mL) were added tert-butyl (E)-N-(4-chlorobenzylidene)-L-alaninate (1.2 g), (R)-4,4-dibutyl-2,6-bis(3,4,5-trifluorophenyl)-4,5-dihydro-3H-dinaphtho[2,1-c:1',2'-e]azepinium bromide (34 mg), and cesium hydroxide monohydrate (3.8 g) at −50° C. The reaction mixture was stirred at −17° C. for 20 hours. To the reaction suspension was added water. The aqueous layer was extracted with diethyl ether and the organic layer was washed with brine. The organic layer was dried over anhydrous magnesium sulfate. The insoluble materials were separated by filtration and the filtrate was concentrated under reduced pressure to obtain tert-butyl (E)-N-(4-chlorobenzylidene)-2,3-difluoro-α,4-dimethyl-L-phenylalaninate (1.90 g) as an oil.

Preparation Example 44

To a solution of (1S)-2-chloro-1-(4-chloro-2-fluorophenyl)ethanol (514 mg) in tetrahydrofuran (5 mL) was added a 10% aqueous sodium hydroxide solution (5 mL) under ice-cooling, followed by warming to room temperature and stirring for 3 hours. Water was added thereto, followed by extracting with ethyl acetate. The organic layer was washed with brine. The organic layer was dried over anhydrous magnesium sulfate, the insoluble materials were then separated by filtration, and the filtrate was concentrated under reduced pressure. The obtained residue was purified by silica gel column chromatography (hexane:ethyl acetate=10:1) to obtain (2S)-2-(4-chloro-2-fluorophenyl)oxirane (316 mg) as an oil.

Preparation Example 45

To 2,2,2-trifluoroethanol (12 mL) was added sodium hydride (a 60% oil dispersion, 340 mg) under ice-cooling, followed by stirring for 20 minutes. To the reaction mixture was added 1-methylcyclopropanamine monohydrochloride (1 g) at the same temperature, and a solution of (2S)-2-(4-chloro-2-fluorophenyl)oxirane (1.39 g) in 2,2,2-trifluoroethanol (5 mL) was added thereto. The reaction mixture was stirred for 7 days and then concentrated. To the obtained residue was added ethyl acetate, water was added thereto, followed by performing liquid separation, and the organic layer was washed with brine. The organic layer was then dried over anhydrous sodium sulfate, the insoluble materials were then separated by filtration, and the filtrate was concentrated under reduced pressure. The obtained residue was purified by silica gel column chromatography (hexane:ethyl acetate=100:0 to 0:100) to obtain (1S)-1-(4-chloro-2-fluorophenyl)-2-[(1-methylcyclopropyl)amino]ethanol (473 mg) as a solid.

Preparation Example 46

To a mixture of 6-bromo-5-fluoroindan-1-one (885 mg) and trifluoroacetic acid (10 mL) was added triethylsilane (1.8 mL) at room temperature, followed by heating and stirring at 80° C. for 3.5 hours. To the reaction mixture was added triethylsilane (0.6 mL), followed by stirring at 80° C. for additional 1 hour, and then stirring at room temperature for 3 days. To the reaction mixture was added water, followed by extracting with hexane. The organic layer was washed with a saturated aqueous sodium hydrogen carbonate solution and brine, and dried over anhydrous magnesium sulfate, the insoluble materials were then separated by filtration, and the filtrate was concentrated under reduced pressure. The obtained residue was purified by silica gel column chromatography (hexane:ethyl acetate=100:0 to 90:10) to obtain 5-bromo-6-fluoroindane (902 mg) as an oil.

Preparation Example 47

A mixture of methyl (2S)-2-[(tert-butoxycarbonyl)amino]-3-(6-fluoro-2,3-dihydro-1H-inden-5-yl)propanoate (873 mg) and hydrogen chloride (4 M solution in dioxane, 10 mL) was stirred at room temperature for 1 hour. The solvent was concentrated under reduced pressure to obtain methyl (2S)-2-amino-3-(6-fluoro-2,3-dihydro-1H-inden-5-yl)propanoate monohydrochloride (708 mg) as a solid.

Preparation Example 48

To a mixture of tert-butyl (3R)-4-[3-(3,4-dichlorophenyl)-1-methoxy-1-oxopropan-2-yl]-3-methylpiperazine-1-carboxylate (266 mg, Preparation Example 21, the earlier eluted fraction) and ethanol (10 mL) was added 10% palladium on carbon (50% water content, 70 mg) under an argon atmosphere. The reaction mixture was stirred at room temperature for 40 hours under a 3-atm hydrogen atmosphere. The insoluble materials were separated by filtration and the filtrate was concentrated under reduced pressure. To a mixture of the obtained residue and ethanol (10 mL) was added 5% rhodium on carbon (50% water content, 170 mg) under an argon atmosphere. The reaction mixture was stirred at room temperature for 15 hours under a 3-atm hydrogen atmosphere. The insoluble materials were separated by filtration and the filtrate was concentrated under reduced pressure. The obtained residue was purified by silica gel column chromatography (hexane:ethyl acetate=10:0 to 7:3) to obtain an oil. To a mixture of the obtained oil and dioxane (500 µL) was added hydrogen chloride (4 M solution in dioxane, 500 µL), followed by stirring at room temperature for 1 day. To the reaction mixture was added a saturated aqueous sodium hydrogen carbonate solution, followed by extracting with ethyl acetate. The organic layer was washed with brine and then dried over anhydrous magnesium sulfate. The insoluble materials were separated by filtration and the filtrate was concentrated under reduced pressure to obtain methyl 3-cyclohexyl-2-[(2R)-2-methylpiperazin-1-yl]propanoate (49 mg) as an oil.

Preparation Example 49

To a mixture of 4-methyltetrahydro-2H-pyran-4-amine monohydrochloride (2.5 g) and acetonitrile (130 mL) were added (chloromethyl)trimethylsilane (8 mL), potassium carbonate (9.1 g), and potassium iodide (5.5 g), followed by stirring at 60° C. for 2 days. The reaction mixture was cooled to room temperature, the solid was then separated by filtration, and the filtrate was concentrated under reduced pressure. The obtained residue was purified by silica gel column chromatography (chloroform:methanol=19:1 to 9:1) to obtain 4-methyl-N-[(trimethylsilyl)methyl]tetrahydro-2H-pyran-4-amine (1.74 g) as an oil.

To the ice-cooled 37% aqueous formaldehyde solution (1.4 mL) was added potassium carbonate (60 mg), and then methanol (700 μL) was added thereto. To the reaction mixture was added dropwise 4-methyl-N-[(trimethylsilyl)methyl]tetrahydro-2H-pyran-4-amine (1.74 g) for 10 minutes to 15 minutes. The reaction mixture was stirred for 1 hour under ice-cooling, and then stirred at 10° C. to 15° C. for 3 hours. The reaction mixture was again ice-cooled, and potassium carbonate (2.4 g) was added thereto, followed by stirring for 1 hour under ice-cooling and then stirring at room temperature overnight. To the reaction mixture was added diethyl ether, followed by washing with brine. The organic layer was then dried over anhydrous sodium sulfate and the insoluble materials were separated by filtration. The filtrate was concentrated under reduced pressure (water bath at 21° C., up to 100 mbar) to obtain an oil (1.48 g) including N-(methoxymethyl)-4-methyl-N-[(trimethylsilyl)methyl]tetrahydro-2H-pyran-4-amine.

To a mixture of the obtained oil (1.47 g), (4S)-4-benzyl-3-[(2E)-3-(2,4-difluorophenyl)prop-2-enoyl]-1,3-oxazolidin-2-one (1 g) and dichloromethane (10 mL) was added dropwise a solution of trifluoroacetic acid (350 μL) in dichloromethane (5 mL) at room temperature under an argon atmosphere, followed by stirring at room temperature overnight. To the reaction mixture was added saturated aqueous sodium bicarbonate, followed by extracting with chloroform, and the organic layer was concentrated under reduced pressure. The obtained residue was purified by silica gel column chromatography (chloroform:methanol=10:0 to 23:2) to obtain (4S)-4-benzyl-3-{[4-(2,4-difluorophenyl)-1-(4-methyltetrahydro-2H-pyran-4-yl)pyrrolidin-3-yl]carbonyl}-1,3-oxazolidin-2-one (542 mg, the earlier eluted fraction) as an oil. Further, a single isomer having a different steric configuration at the 3- and 4-positions of the pyrrolidine group (550 mg, Preparation Example 49, the later eluted fraction) was obtained as a solid. For the reaction for obtaining Preparation Example 372, Preparation Example 49 was used.

Preparation Example 416

To a mixture of (4S)-4-benzyl-3-{[(3S,4R)-1-tert-butyl-4-(4-chloro-2-fluorophenyl)pyrrolidin-3-yl]carbonyl}-1,3-oxazolidin-2-one (135 mg), tetrahydrofuran (3 mL), and water (0.6 mL) was added lithium hydroxide monohydrate (25 mg) under ice-cooling. The mixture was warmed to room temperature and then stirred for 1 hour. To the reaction mixture was added 1 M hydrochloric acid (0.61 mL), followed by concentrating. Into another reaction flask were added (4S)-4-benzyl-3-{[(3S,4R)-1-tert-butyl-4-(4-chloro-2-fluorophenyl)pyrrolidin-3-yl]carbonyl}-1,3-oxazolidin-2-one (3.55 g), tetrahydrofuran (78 mL), and water (15 mL), and then lithium hydroxide monohydrate (660 mg) was added thereto under ice-cooling. The mixture was warmed to room temperature and then stirred for 1.5 hours. To the reaction mixture was added 1 M hydrochloric acid (16 mL), followed by concentrating. The residues obtained by the respective reactions were combined and purified by ODS silica gel column chromatography (water:acetonitrile=9:1 to 0:10). To the obtained residue was added ethanol, followed by concentrating. To the obtained residue was added hydrogen chloride (4 M solution in dioxane, 5.8 mL), then diisopropyl ether was added thereto, and the precipitated solid was filtered. The obtained solid was dried at 40° C. under reduced pressure to obtain (3S,4R)-1-tert-butyl-4-(4-chloro-2-fluorophenyl)pyrrolidine-3-carboxylic acid monohydrochloride (2.67 g) as a solid.

Preparation Example 417

To a mixture of tert-butyl (2S)-3-(4-bromo-2-fluorophenyl)-2-{(3S)-3-methyl-4-[(2-nitrophenyl)sulfonyl]-2-oxopiperazin-1-yl}propanoate (2 g), dioxane (20 mL), and water (2.4 mL) were added methylboronic acid (206 mg), tripotassium phosphate (2.06 g), a [1,1'-bis(diphenylphosphino) ferrocene]palladium (II) dichloride dichloromethane adduct (280 mg), followed by irradiating with microwave under an argon atmosphere and stirring at 100° C. for 1 hour. The reaction mixture was filtered through Celite and the filtrate was concentrated. The obtained residue was purified by silica gel column chromatography (hexane:ethyl acetate=89:11 to 20:80). To the obtained oil were added ethyl acetate (1 mL) and hexane (2 mL), followed by stirring for 1 hour, and then hexane (5 mL) was added thereto. The solid was filtered and then dried under reduced pressure to obtain tert-butyl (2S)-3-(2-fluoro-4-methylphenyl)-2-{(3S)-3-methyl-4-[(2-nitrophenyl)sulfonyl]-2-oxopiperazin-1-yl}propanoate (1.41 g) as a solid.

In the same manner as the methods described in above Preparation Examples, the compounds of Preparation Examples 50 to 415, 418 to 421 shown in the following tables were prepared.

The structures of the Preparation Example compounds are shown in Tables 6 to 48, and the physicochemical data and the preparation methods of Preparation Example compounds are shown in Tables 49 to 61.

Example 1

To a solution of methyl (2S)-2-[(3S)-4-{[(3S,4R)-4-(4-chloro-2-fluorophenyl)-1-(tetrahydro-2H-pyran-4-yl)pyrrolidin-3-yl]carbonyl}-3-methylpiperazin-1-yl]-3-(2-fluoro-4-methylphenyl)propanoate (2.28 g) in tetrahydrofuran (40 mL) was added a solution of lithium hydroxide monohydrate (396 mg) in water (10 mL) at room temperature, followed by stirring at room temperature overnight. To the reaction mixture was added 1 M hydrochloric acid (9.45 mL) at room temperature, followed by concentrating under reduced pressure. To the residue were added water (about 5 mL) and ethanol (about 5 mL), followed by stirring, and to the obtained suspension was added water (150 mL), followed by stirring at room temperature for 2 hours. The resulting solid was collected by filtration and then washed with water to obtain (2S)-2-[(3S)-4-{[(3S,4R)-4-(4-chloro-2-fluorophenyl)-1-(tetrahydro-2H-pyran-4-yl)pyrrolidin-3-yl]carbonyl}-3-methylpiperazin-1-yl]-3-(2-fluoro-4-methylphenyl)propanoic acid (1.95 g) as a crystal.

Example 2

To a solution of tert-butyl (2S)-2-[(3S)-4-{[(3S,4R)-4-(4-chloro-2-fluorophenyl)-1-(tetrahydro-2H-pyran-4-yl)pyrrolidin-3-yl]carbonyl}-3-methylpiperazin-1-yl]-3-(2-fluoro-4,6-dimethylphenyl)propanoate (33.3 g) in dioxane (60 mL) was added concentrated hydrochloric acid (60 mL), followed by stirring at 50° C. for 2 hours. The solvent was evaporated under reduced pressure and the residue was diluted with ethyl acetate and water. The mixture was adjusted to pH=7.3 by the addition of a 5 M aqueous sodium hydroxide solution, and extracted with ethyl acetate. The organic layer was washed with brine which had been adjusted to pH=7.3. The organic layer was then dried over anhydrous sodium sulfate, the insoluble materials were then separated by filtration, and the filtrate was concentrated under reduced pressure. The obtained solid was suspended in a mixed solvent (185 mL) of ethanol:water (3:7) at 90° C., and then ethanol (33 mL) was added thereto to obtain a solution. The solution was left to be cooled to room temperature and the resulting solid was collected by filtration. The obtained solid was washed with a mixed solvent of ethanol:water (1:2) and then dried under reduced pressure to obtain (2S)-2-[(3S)-4-{[(3S,4R)-4-(4-chloro-2-fluorophenyl)-1-(tetrahydro-2H-pyran-4-yl)pyrrolidin-3-yl]carbonyl}-3-methylpiperazin-1-yl]-3-(2-fluoro-4,6-dimethylphenyl)propanoic acid (27.5 g) as a crystal.

Example 3

To a solution of methyl (2S)-2-[(3S)-4-{[(3S,4R)-1-tert-butyl-4-(4-chloro-2-fluorophenyl)pyrrolidin-3-yl]carbonyl}-3-methylpiperazin-1-yl]-3-mesitylpropanoate (29.8 g) in tetrahydrofuran (595 mL) was added a solution of lithium hydroxide monohydrate (5.33 g) in water (149 mL) under ice-cooling. The reaction mixture was stirred at room temperature for 1 day. To the reaction mixture was added lithium hydroxide monohydrate (3.2 g). The reaction mixture was stirred at room temperature for 4 days. The reaction mixture was left to stand and the organic layer was separated. The organic layer was concentrated under reduced pressure, and the residue and the aqueous layer were combined. To the aqueous layer was added water (800 mL), followed by washing with diethyl ether (300 mL). The aqueous layer was adjusted to pH=6 by the addition of 1 M hydrochloric acid (200 mL), and the reaction mixture was stirred at room temperature for 30 minutes. The insoluble materials were separated by filtration, and then to the filtrate were added ethanol (75 mL) and water (75 mL), followed by stirring at room temperature for 1 day. The precipitated solid was separated by filtration, washed with a mixed solvent of ethanol-water (1:1), and then dried under reduced pressure to obtain (2S)-2-[(3S)-4-{[(3S,4R)-1-tert-butyl-4-(4-chloro-2-fluorophenyl)pyrrolidin-3-yl]carbonyl}-3-methylpiperazin-1-yl]-3-mesitylpropanoic acid (26 g) as a crystal.

Example 4

To a mixed solution of methyl (2S)-2-[(3S)-4-{[(3S,4R)-1-tert-butyl-4-(4-chloro-2-fluorophenyl)pyrrolidin-3-yl]carbonyl}-3-methylpiperazin-1-yl]-3-(2-fluoro-4-methylphenyl)propanoate (250 mg) in tetrahydrofuran (3 mL)-water (0.7 mL) was added lithium hydroxide monohydrate (45 mg), followed by stirring at room temperature overnight. To the reaction mixture was added 1 M hydrochloric acid (1.08 mL), and water was added thereto, followed by extracting with chloroform. The organic layer was dried over anhydrous magnesium sulfate, the insoluble materials were then separated by filtration, and the filtrate was concentrated under reduced pressure. The obtained residue was dissolved in ethyl acetate (5 mL), and hydrogen chloride (4 M solution in ethyl acetate, 0.3 mL) was added thereto. To the reaction mixture was added hexane, followed by stirring. The precipitated solid was collected by filtration and then dried under reduced pressure to obtain (2S)-2-[(3S)-4-{[(3S,4R)-1-tert-butyl-4-(4-chloro-2-fluorophenyl)pyrrolidin-3-yl]carbonyl}-3-methylpiperazin-1-yl]-3-(2-fluoro-4-methylphenyl)propanoic acid dihydrochloride (215 mg) as a solid.

Example 5

To a solution of tert-butyl (2S)-2-[(3S)-4-{[(3S,4R)-1-tert-butyl-4-(2,4-difluorophenyl)pyrrolidin-3-yl]carbonyl}-3-methylpiperazin-1-yl]-3-(2,3-dihydro-1H-inden-5-yl)propanoate (0.84 g) in dioxane (7.4 mL) was added concentrated hydrochloric acid (7.4 mL), followed by stirring at room temperature for 6 hours. The reaction mixture was concentrated under reduced pressure, and the obtained residue was triturated using diisopropyl ether. The solid was filtered and then dried under reduced pressure to obtain (2S)-2-[(3S)-4-{[(3S,4R)-1-tert-butyl-4-(2,4-difluorophenyl)pyrrolidin-3-yl]carbonyl}-3-methylpiperazin-1-yl]-3-(2,3-dihydro-1H-inden-5-yl)propanoic acid dihydrochloride (0.77 g) as a solid.

Example 6

A mixture of methyl (2S)-2-[(3R,5S)-3,5-dimethylpiperazin-1-yl]-3-(2-naphthyl)propanoate (102 mg), (3S,4R)-1-tert-butyl-4-(2,4-difluorophenyl)pyrrolidine-3-carboxylic acid (89 mg), O-(7-aza-1H-benzotriazol-1-yl)-N,N,N',N'-tetramethyluronium hexafluorophosphate (160 mg), N,N-diisopropyl ethylamine (160 µL), and N,N-dimethylformamide (2 mL) was stirred at room temperature for 3 days. To the reaction mixture was added O-(7-aza-1H-benzotriazol-1-yl)-N,N,N',N'-tetramethyluronium hexafluorophosphate (80 mg), followed by stirring at room temperature for additional 4 days. To the reaction mixture was added water, followed by extracting with ethyl acetate. The organic layer was washed with brine and then concentrated under reduced pressure. The obtained residue was purified by silica gel column chromatography (chloroform:methanol=99:1 to 90:10). A mixture of the obtained oil (21 mg), tetrahydrofuran (2 mL), and water (400 µL) was ice-cooled, and then lithium hydroxide monohydrate (10 mg) was added thereto under stirring. The reaction mixture was stirred at room temperature overnight. To the reaction mixture was added lithium hydroxide monohydrate (10 mg), followed by further stirring at room temperature overnight. To the reaction mixture was added 1 M hydrochloric acid (0.5 mL), followed by extracting with ethyl acetate. The organic layer was washed with brine and then concentrated under reduced pressure. The residue was purified by silica gel column chromatography (chloroform:methanol=94:6 to 80:20). To the obtained residue (13 mg) were added tetrahydrofuran and hydrogen chloride (4 M solution in dioxane, 100 µL), followed by concentrating under reduced pressure. The residue was triturated by the addition of ethyl acetate and hexane, and the solid was collected by filtration and the dried at 40° C. under reduced pressure to obtain (2S)-2-[(3R,5S)-4-{[(3S,4R)-1-tert-butyl-4-(2,4-difluorophenyl)pyrrolidin-3-yl]carbonyl}-3,5-dimethylpiperazin-1-yl]-3-(2-naphthyl)propanoic acid dihydrochloride (7.2 mg) as a solid.

Example 7

To a mixed solution of (2S)-2-[(3S)-4-{[(3S,4R)-1-tert-butyl-4-(2,4-difluorophenyl)pyrrolidin-3-yl]carbonyl}-3-methylpiperazin-1-yl]-3-(4-chloro-2-methylphenyl)propanoic acid dihydrochloride (100 mg) in ethanol (15 mL) was added 10% palladium on carbon (50% water content, 100 mg) under an argon atmosphere. The reaction mixture was stirred at room temperature for 24 hours under a 4-atm hydrogen atmosphere. After replacing to an argon atmosphere, the insoluble materials were separated by filtration, and the filtrate was concentrated under reduced pressure. To the obtained residue were added tetrahydrofuran (4 mL) and hydrogen chloride (4 M solution in dioxane, 0.5 mL). The solvent was concentrated under reduced pressure, the obtained residue was triturated by the addition of diethyl ether, and then the solid was collected by filtration to obtain (2S)-2-[(3S)-4-{[(3S,4R)-1-tert-butyl-4-(2,4-difluorophenyl)pyrrolidin-3-yl]carbonyl}-3-methylpiperazin-1-yl]-3-(2-methylphenyl)propanoic acid dihydrochloride (93 mg) as a solid.

Example 8

To a solution of tert-butyl 3-ambo-(2S,3R)-2-[(3S)-4-{[(3S,4R)-1-tert-butyl-4-(2,4-difluorophenyl)pyrrolidin-3-yl]carbonyl}-3-methylpiperazin-1-yl]-3-(4-methylphenyl)butanoate (504 mg) in dioxane (4 mL) was added concentrated hydrochloric acid (4 mL), followed by stirring at 50° C. for 1 hour. The reaction mixture was neutralized to pH=7 with a 1 M aqueous sodium hydroxide solution and extracted with ethyl acetate. The organic layer was washed with brine and dried over anhydrous magnesium sulfate. The insoluble materials were separated by filtration and the filtrate was concentrated under reduced pressure. The obtained residue was purified by ODS silica gel column chromatography (water:methanol=90:10 to 20:80). The earlier eluted fraction was concentrated, and dioxane (5 mL) and hydrogen chloride (4 M solution in dioxane, 633 µL) were added thereto, followed by concentrating under reduced pressure. To the obtained residue were added ethyl acetate and hexane, and the precipitated solid was collected by filtration and then dried under reduced pressure to obtain (2S,3S)-2-[(3S)-4-{[(3S,4R)-1-tert-butyl-4-(2,4-difluorophenyl)pyrrolidin-3-yl]carbonyl}-3-methylpiperazin-1-yl]-3-(4-methylphenyl)butanoate dihydrochloride (190 mg, Example 8) as a solid. The later eluted fraction was concentrated, and dioxane (5 mL) and hydrogen chloride (4 M solution in dioxane, 633 µL) were added thereto, followed by concentrating under reduced pressure. To the obtained residue were added ethyl acetate and hexane, and the precipitated solid was collected by filtration and then dried under reduced pressure to obtain (2S,3R)-2-[(3S)-4-{[(3S,4R)-1-tert-butyl-4-(2,4-difluorophenyl)pyrrolidin-3-yl]carbonyl}-3-methylpiperazin-1-yl]-3-(4-methylphenyl)butanoate dihydrochloride (33 mg) as a solid.

Example 87

To a solution of (2S)-2-[(3S)-4-{[(3S,4R)-4-(4-chloro-2-fluorophenyl)-1-(tetrahydro-2H-pyran-4-yl)pyrrolidin-3-yl]carbonyl}-3-methylpiperazin-1-yl]-3-(2-fluoro-4-methylphenyl)propanoic acid (110 mg) in tetrahydrofuran (5 mL) was added hydrogen chloride (4 M solution in dioxane, 107 µL), followed by stirring at room temperature for 2 hours. The precipitated solid was collected by filtration, washed with ethyl acetate, and dried under reduced pressure to obtain (2S)-2-[(3S)-4-{[(3S,4R)-4-(4-chloro-2-fluorophenyl)-1-(tetrahydro-2H-pyran-4-yl)pyrrolidin-3-yl]carbonyl}-3-methylpiperazin-1-yl]-3-(2-fluoro-4-methylphenyl)propanoic acid dihydrochloride (102 mg) as a solid.

Example 101

A solution of methyl (2S)-3-(2-fluoro-4-methylphenyl)-2-{(3S)-3-methyl-4-[(2-nitrophenyl)sulfonyl]piperazin-1-yl}propanoate (23.47 g), cesium carbonate (47.8 g), and 1-dodecanethiol (35.2 mL) in acetonitrile (188 mL) was stirred at 60° C. for 16 hours and 35 minutes. The insoluble materials were filtered and then washed with acetonitrile (281.6 mL). To the filtrate were added n-heptane (187.8 mL) and water (70.4 mL), followed by adjusting to pH 3.99 by the addition of 1 M hydrochloric acid. The aqueous layer was separated and washed four times with n-heptane (187.8 mL), and then isopropyl acetate (187.8 mL) and a 20% aqueous sodium chloride solution (140.8 mL) were added thereto, followed by adjusting to pH 9.03 by the addition of a 20% aqueous potassium carbonate solution. The organic layer was separated and washed with a 20% aqueous sodium chloride solution (140.8 mL) and then concentrated under reduced pressure. Acetonitrile (234.7 mL) was added thereto, followed by concentrating under reduced pressure, and acetonitrile (234.7 mL) was added thereto again, followed by concentrating under reduced pressure. Methyl (2S)-3-(2-fluoro-4-methylphenyl)-2-[(3S)-3-methylpiperazin-1-yl]propanoate was obtained as a concentrated solution in acetonitrile.

To the obtained concentrated solution of methyl (2S)-3-(2-fluoro-4-methylphenyl)-2-[(3S)-3-methylpiperazin-1-yl]propanoate in acetonitrile was added acetonitrile (211 mL), and (3S,4R)-4-(4-chloro-2-fluorophenyl)-1-(tetrahydro-2H-pyran-4-yl)pyrrolidine-3-carboxylic acid (17.65 g), N,N-diisopropyl ethylamine (20.1 mL), and O-(7-aza-1H-benzotriazol-1-yl)-N,N,N',N-tetramethyluronium hexafluorophosphate (21.41 g) were added thereto at 5° C., followed by stirring for 21 hours and 30 minutes. Toluene (234.7 mL) and water (234.7 mL) were added thereto, and then the organic layer was separated. The organic layer was washed twice with water (234.7 mL), twice with a 5% aqueous sodium hydrogen carbon solution (234.7 mL), twice with a 20% aqueous ammonium chloride solution (234.7 mL), and once with a 20% aqueous sodium chloride solution (234.7 mL), and then the organic layer was concentrated under reduced pressure. To the concentrated solution was added methanol (234.7 mL), followed by concentrating under reduced pressure, and then methanol (234.7 mL) was added thereto again, followed by concentrating under reduced pressure. Methyl (2S)-2-[(3S)-4-{[(3S,4R)-4-(4-chloro-2-fluorophenyl)-1-(tetrahydro-2H-pyran-4-yl)pyrrolidin-3-yl]carbonyl}-3-methylpiperazin-1-yl]-3-(2-fluoro-4-methylphenyl)propanoate was obtained as a concentrated solution in methanol.

To the obtained concentrated solution of methyl (2S)-2-[(3S)-4-{[(3S,4R)-4-(4-chloro-2-fluorophenyl)-1-(tetrahydro-2H-pyran-4-yl)pyrrolidin-3-yl]carbonyl}-3-methylpiperazin-1-yl]-3-(2-fluoro-4-methylphenyl)propanoate in methanol were added methanol (117 mL) and a solution of lithium hydroxide monohydrate (5.14 g) in water (47 mL), followed by stirring at 23.8° C. to 24.3° C. for 12 hours and 40 minutes. Toluene (187.8 mL) was added thereto, and then the aqueous layer was separated. The aqueous layer was washed 3 times with toluene (187.8 mL), and then isopropyl acetate (187.8 mL) was added thereto, followed by adjusting to pH 6.51 by the addition of 1 M hydrochloric acid. Then, a 20% aqueous sodium chloride solution (117.4 mL) was added thereto, and then the organic layer was separated. The aqueous layer was extracted twice with isopropyl acetate (187.8 mL), the obtained organic layer was combined with the previous organic layer and then concentrated under reduced pressure. To the concentrated solution was added ethanol (234.7 mL), followed by concentrating again under reduced pressure, and ethanol (234.7 mL) was added thereto again, followed by concentrating under reduced pressure. To the concentrated solution were added ethanol (117.4 mL) and water (46.9 mL), followed by dissolving and heating, and then water (93.9 mL) was added thereto, followed by stirring at 55° C. for 2 hours and 30 minutes. Water (187.8 mL) was added thereto, followed by stirring at 50° C. to 60° C. for 1 hour, cooling to 25° C., and stirring for 18 hours and 55 minutes. Then, the mixture was adjusted to pH 6.48 by the addition of a 1 M aqueous sodium hydroxide solution. The mixture was cooled to 5° C. and stirred for 3 hours and 15 minutes, and then the solid was collected by filtration, washed with a mixed solution of ethanol and water, and dried under reduced pressure to obtain (2S)-2-[(3S)-4-{[(3S,4R)-4-(4-chloro-2-fluorophenyl)-1-(tetrahydro-2H-pyran-4-yl)pyrrolidin-3-yl]carbonyl}-3-methylpiperazin-1-yl]-3-(2-fluoro-4-methylphenyl)propanoic acid (24.68 g) as a solid.

To (2S)-2-[(3S)-4-{[(3S,4R)-4-(4-chloro-2-fluorophenyl)-1-(tetrahydro-2H-pyran-4-yl)pyrrolidin-3-yl]carbonyl}-3-methylpiperazin-1-yl]-3-(2-fluoro-4-methylphenyl)propanoic acid (22.00 g) was added a mixed solution of 1-propanol (211.2 mL) and water (52.8 mL), followed by heating and dissolving. The insoluble materials were removed by filtration, followed by washing with a mixed solution of 1-propanol (8.8 mL) and water (35.2 mL). To the filtrate was added dropwise water (352 mL) at 62° C., and then seed crystals were added thereto, followed by stirring at 61.5° C. to 61.9° C. for 37 hours. The mixture was cooled and stirred at 20° C. for 24 hours, and then water (220 mL) was added dropwise thereto, followed by stirring at 20° C. for 68 hours and then stirring at 10° C. for 26 hours. The solid was collected by filtration, washed with a mixed solution of 1-propanol (8.8 mL) and water (35.2 mL), and dried under reduced pressure to obtain (2S)-2-[(3S)-4-{[(3S,4R)-4-(4-chloro-2-fluorophenyl)-1-(tetrahydro-2H-pyran-4-yl)pyrrolidin-3-yl]carbonyl}-3-methylpiperazin-1-yl]-3-(2-fluoro-4-methylphenyl)propanoic acid (20.23 g) as a crystal.

2θ(°)=13.7, 14.7, 16.0, 17.3, 18.4, 19.6, 20.4, 21.0, 21.6, 24.7, 26.1

Furthermore, the seed crystals used in Example 101 can be obtained by carrying out the same procedure without use of the seed crystals.

In the same manner as the methods described in Examples, the compounds of Examples 9 to 86, 88 to 100 shown in the following tables were prepared.

The structures of the Example compounds are shown in Tables 62 to 71, and the physicochemical data and the preparation methods of Example compounds are shown in Tables 72 to 76.

These can be easily prepared by using the preparation methods as described above, or the method described in Examples, methods apparent to a person skilled in the art, or modified methods thereof.

TABLE 6

| PEx | Str |
|---|---|
| 1 |  |
| 2 |  |
| 3 |  |
| 4 |  # |
| 5 |  |
| 6 |  |

TABLE 6-continued

| PEx | Str |
|---|---|
| 7 | (structure) |
| 8 | (structure) |
| 9 | (structure) |
| 10 | (structure) |

TABLE 7

| PEx | Str |
|---|---|
| 11 | (structure) |
| 12 | (structure) |
| 13 | (structure) |
| 14 | (structure) |
| 15 | (structure) |
| 16 | (structure) |
| 17 | (structure) |
| 18 | (structure) |

TABLE 7-continued
| PEx | Str |
|---|---|
| 19 | 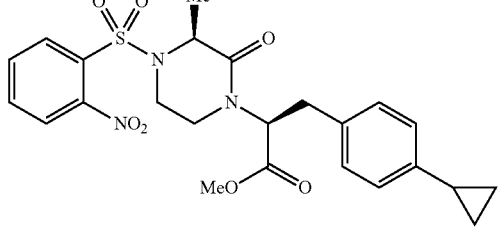 |
| 20 | 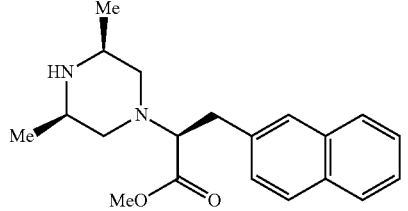 [SMILES: COC(=O)[C@H](Cc1ccc2ccccc2c1)N1C[C@@H](C)N[C@@H](C)C1] |
TABLE 8
| PEx | Str |
|---|---|
| 21 | 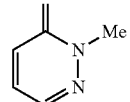 |
| 22 | 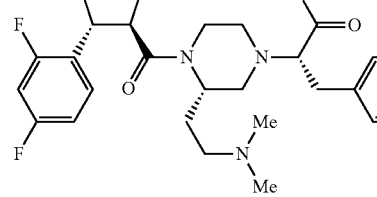 |
| 23 | 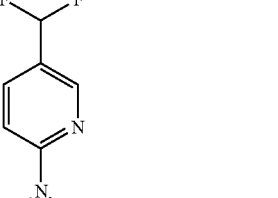 |
TABLE 8-continued
| PEx | Str |
|---|---|
| 24 | 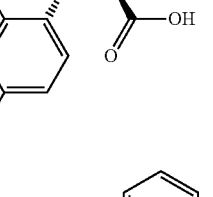 |
| 25 | 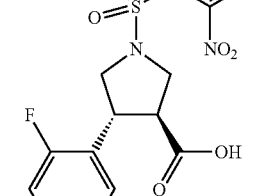 |
| 26 | 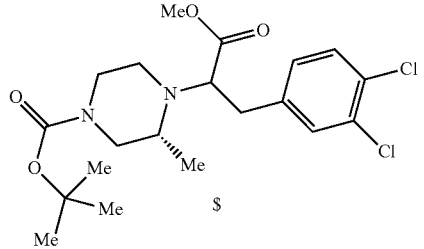 [SMILES: COC(=O)C(Cc1ccc(Cl)c(Cl)c1)N1CCN(C(=O)OC(C)(C)C)C[C@H]1C] |
| 27 | 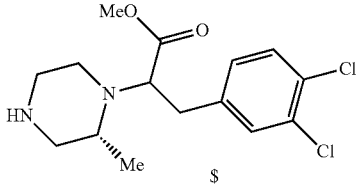 [SMILES: COC(=O)C(Cc1ccc(Cl)c(Cl)c1)N1CCNC[C@H]1C] |

TABLE 8-continued

| PEx | Str |
|---|---|
| 28 | (structure) |
| 29 | (structure) |
| 30 | (structure) |

TABLE 9

| PEx | Str |
|---|---|
| 31 | (structure) |
| 32 | (structure) |
| 33 | (structure) |
| 34 | (structure) |
| 35 | (structure) |
| 36 | (structure) |
| 37 | (structure) |

TABLE 9-continued
| PEx | Str |
|---|---|
| 38 | 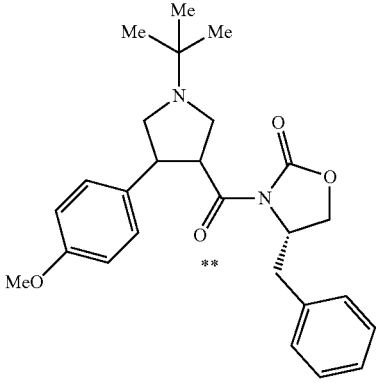 [SMILES: COc1ccc(C2CN(C(C)(C)C)CC2C(=O)N2C(=O)OC[C@@H]2Cc2ccccc2)cc1] |
| 39 | 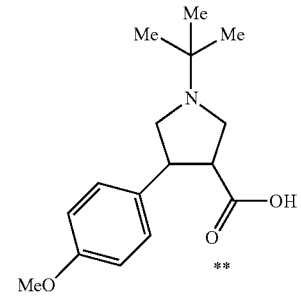 [SMILES: COc1ccc(C2CN(C(C)(C)C)CC2C(=O)O)cc1] |
| 40 | 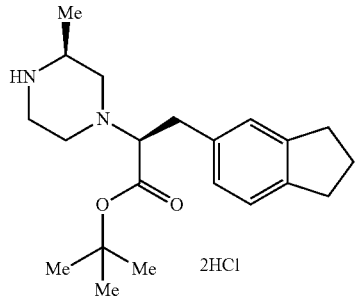 [SMILES: C[C@H]1CN([C@@H](Cc2ccc3c(c2)CCC3)C(=O)OC(C)(C)C)CCN1] |
TABLE 10
| PEx | Str |
|---|---|
| 41 | 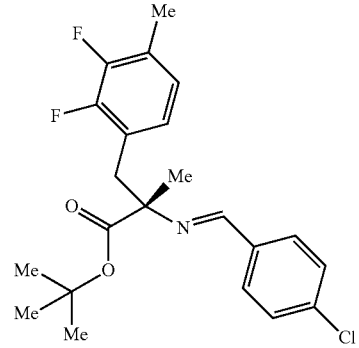 [SMILES: Cc1ccc(C[C@](C)(/N=C/c2ccc(Cl)cc2)C(=O)OC(C)(C)C)c(F)c1F] |
| 42 | 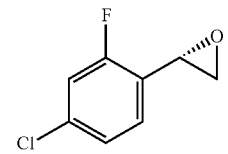 [SMILES: Fc1cc(Cl)ccc1[C@H]1CO1] |
TABLE 10-continued
| PEx | Str |
|---|---|
| 43 | 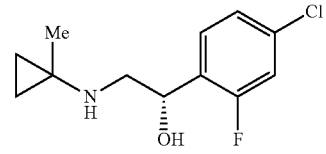 [SMILES: CC1(NC[C@@H](O)c2ccc(Cl)cc2F)CC1] |
| 44 | 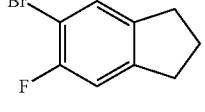 |
| 45 | 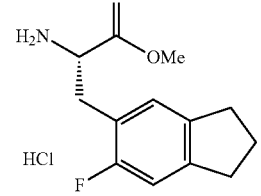 |
| 46 | 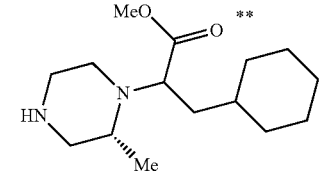 [SMILES: COC(=O)C(CC1CCCCC1)N1CCNC[C@H]1C] |
| 47 | 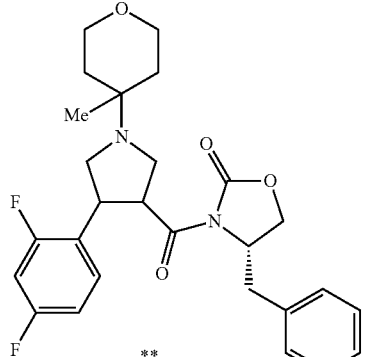 |
| 48 | 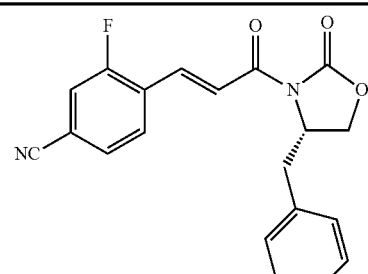 |
| 49 | 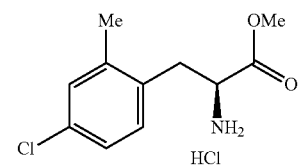 |

TABLE 10-continued
| PEx | Str |
|---|---|
| 50 | 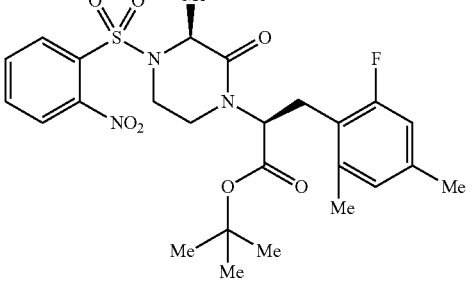 |
TABLE 11
| PEx | Str |
|---|---|
| 51 | |
| 52 | |
| 53 | |
| 54 | |
| 55 | |
| 56 | |
| 57 | |
| 58 | |
| 59 | |

TABLE 11-continued

| PEx | Str |
|---|---|
| 60 | (structure) |

TABLE 12

| PEx | Str |
|---|---|
| 61 | (structure) |
| 62 | (structure) |
| 63 | (structure) |
| 64 | (structure) |

TABLE 12-continued

| PEx | Str |
|---|---|
| 65 | (structure) |
| 66 | (structure) |
| 67 | (structure) |
| 68 | (structure) |
| 69 | (structure) |
| 70 | (structure) |

TABLE 13
| PEx | Str |
|---|---|
| 71 | 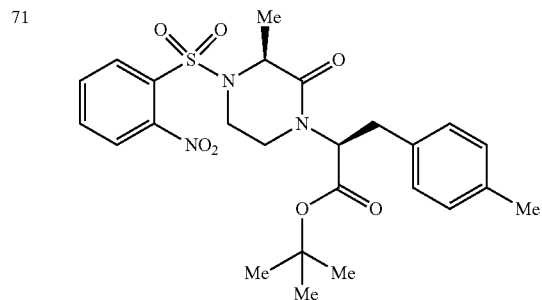 |
| 72 | 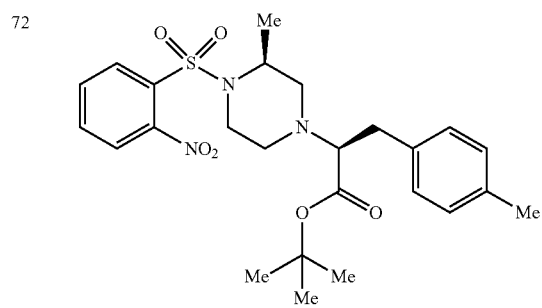 |
| 73 | 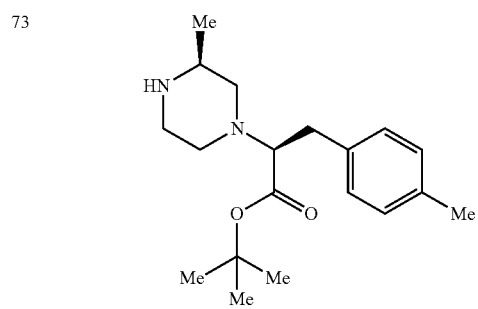 |
| 74 | 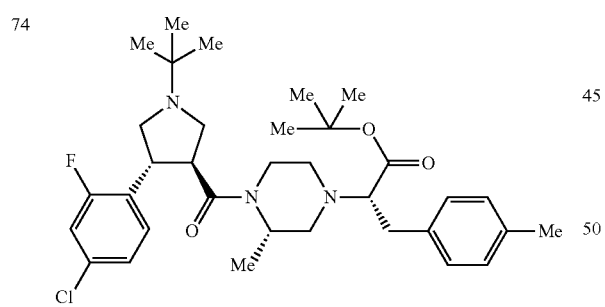 |
| 75 | 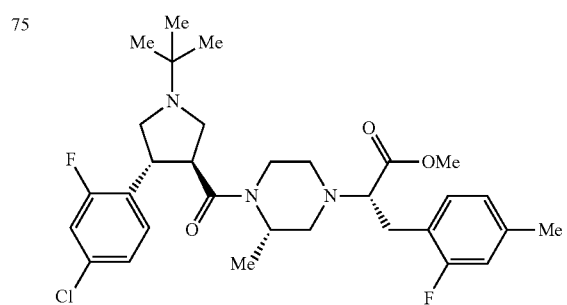 |
TABLE 13-continued
| PEx | Str |
|---|---|
| 76 | 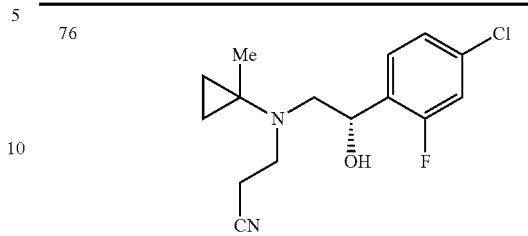 |
| 77 | 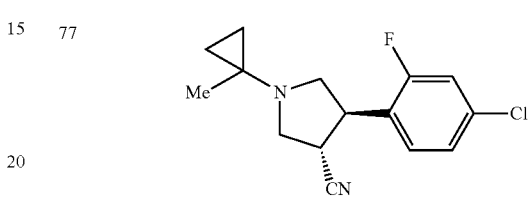 |
| 78 | 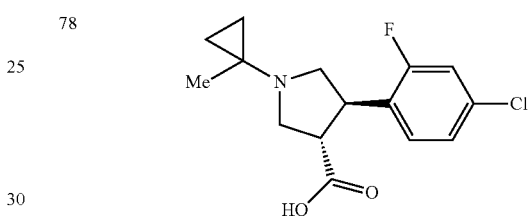 |
| 79 | 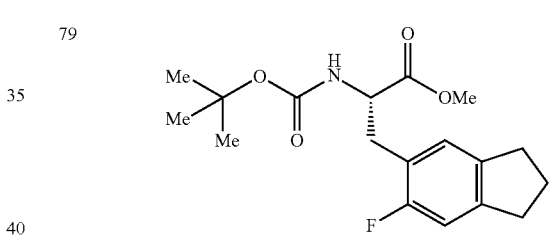 |
| 80 | 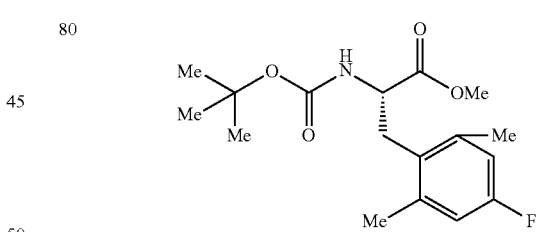 |
TABLE 14
| PEx | Str |
|---|---|
| 81 | 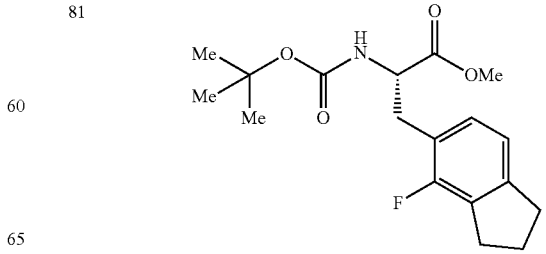 |

TABLE 14-continued
| PEx | Str |
|---|---|
| 82 | 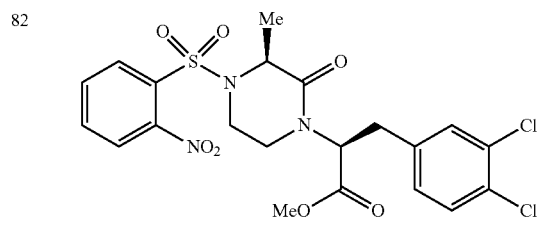 |
| 83 | 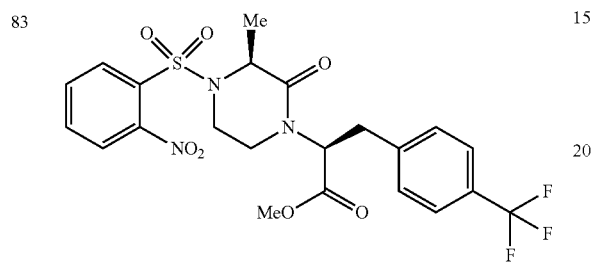 |
| 84 | 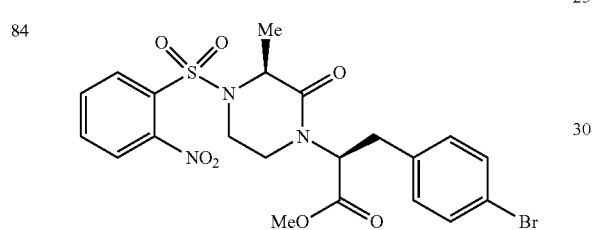 |
| 85 | 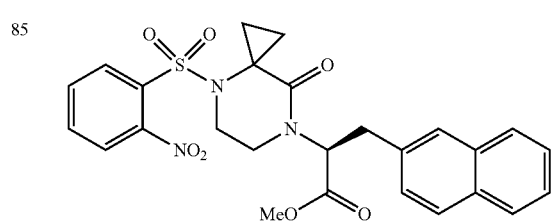 |
| 86 | 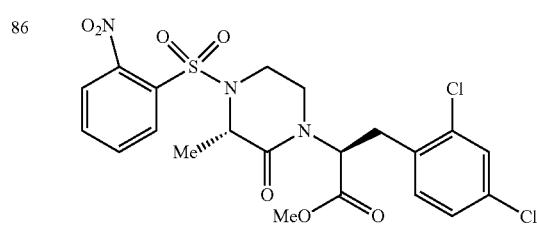 |
| 87 | 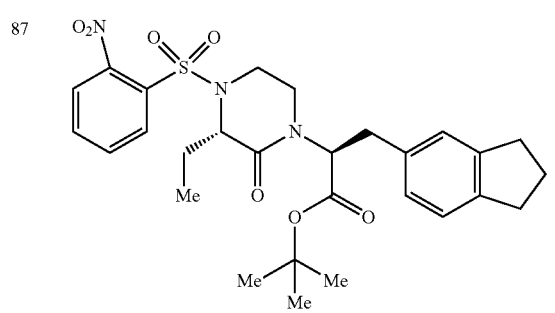 |
| 88 | 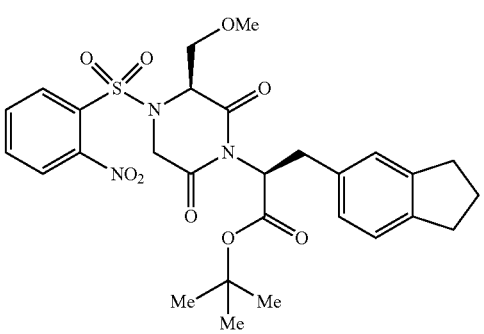 [SMILES: COC[C@H]1C(=O)N([C@@H](Cc2ccc3c(c2)CCC3)C(=O)OC(C)(C)C)C(=O)CN1S(=O)(=O)c1ccccc1[N+](=O)[O-]] |
| 89 | 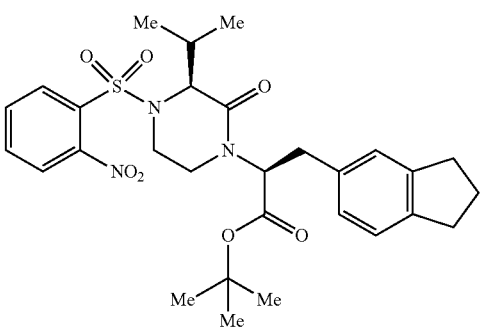 [SMILES: CC(C)[C@H]1C(=O)N([C@@H](Cc2ccc3c(c2)CCC3)C(=O)OC(C)(C)C)CCN1S(=O)(=O)c1ccccc1[N+](=O)[O-]] |
| 90 | 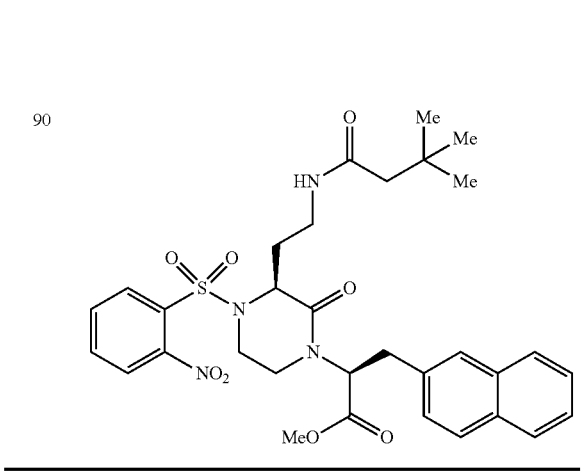 |
TABLE 15
| PEx | Str |
|---|---|
| 91 | 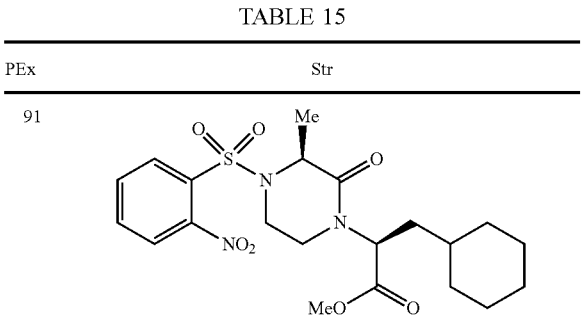 |

TABLE 15-continued

| PEx | Str |
|---|---|
| 92 | (structure) |
| 93 | (structure) |
| 94 | (structure) |
| 95 | (structure) |
| 96 | (structure) |

TABLE 15-continued

| PEx | Str |
|---|---|
| 97 | (structure) |
| 98 | (structure) |
| 99 | (structure) |
| 100 | (structure) |

TABLE 16

| PEx | Str |
|---|---|
| 101 | (structure) |

TABLE 16-continued

| PEx | Str |
|---|---|
| 102 | (structure) |
| 103 | (structure) |
| 104 | (structure) |
| 105 | (structure) |
| 106 | (structure) |
| 107 | (structure) |

TABLE 16-continued

| PEx | Str |
|---|---|
| 108 | (structure) |
| 109 | (structure) |
| 110 | (structure) |

TABLE 17

| PEx | Str |
|---|---|
| 111 | (structure) |
| 112 | (structure) |

TABLE 17-continued
| PEx | Str |
|---|---|
| 113 | 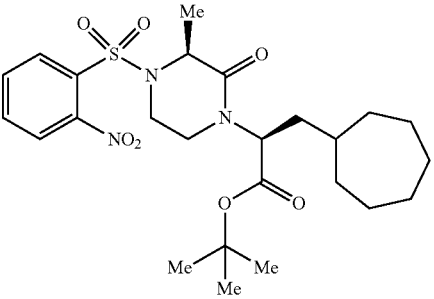 [SMILES: C[C@H]1C(=O)N([C@@H](CC2CCCCCC2)C(=O)OC(C)(C)C)CCN1S(=O)(=O)c1ccccc1[N+](=O)[O-]] |
| 114 | 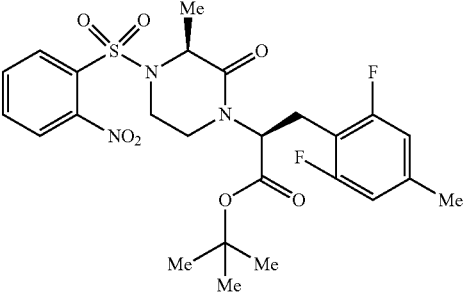 [SMILES: Cc1cc(F)c(C[C@@H](C(=O)OC(C)(C)C)N2CCN(S(=O)(=O)c3ccccc3[N+](=O)[O-])[C@@H](C)C2=O)c(F)c1] |
| 115 | 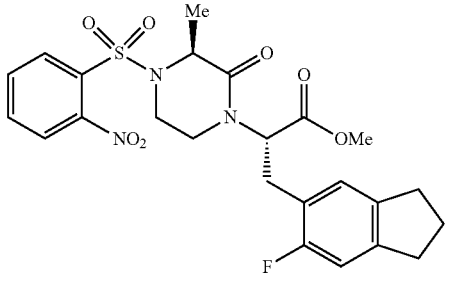 [SMILES: COC(=O)[C@H](Cc1cc2c(cc1F)CCC2)N1CCN(S(=O)(=O)c2ccccc2[N+](=O)[O-])[C@@H](C)C1=O] |
| 116 | 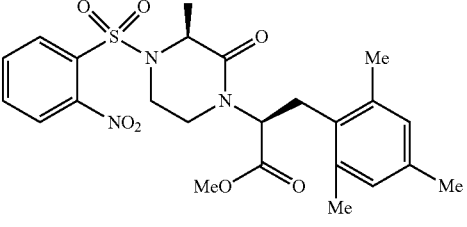 |
| 117 | 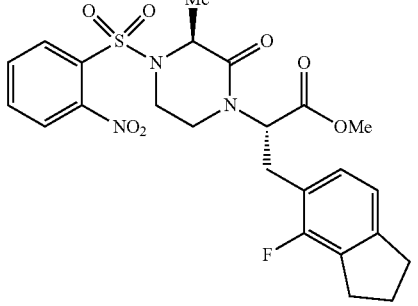 |
TABLE 17-continued
| PEx | Str |
|---|---|
| 118 | 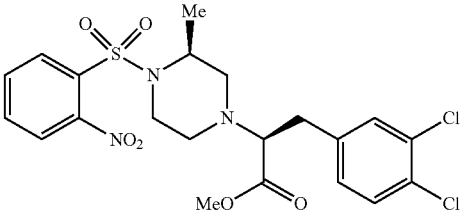 [SMILES: COC(=O)[C@H](Cc1ccc(Cl)c(Cl)c1)N1CCN(S(=O)(=O)c2ccccc2[N+](=O)[O-])[C@@H](C)C1] |
| 119 | 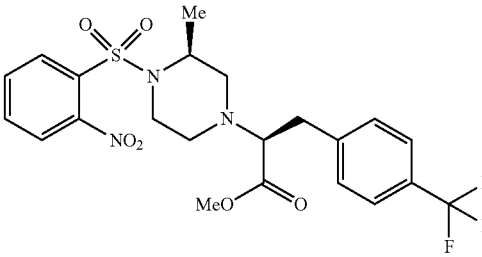 |
| 120 | 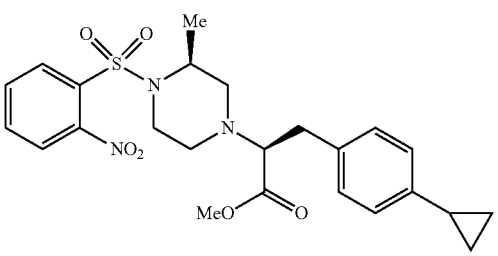 [SMILES: COC(=O)[C@H](Cc1ccc(C2CC2)cc1)N1CCN(S(=O)(=O)c2ccccc2[N+](=O)[O-])[C@@H](C)C1] |
TABLE 18
| PEx | Str |
|---|---|
| 121 | 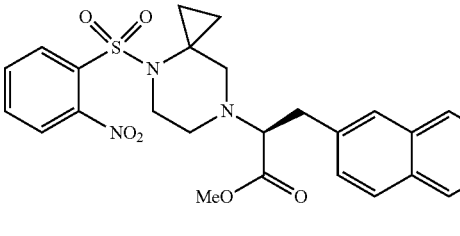 |
| 122 | 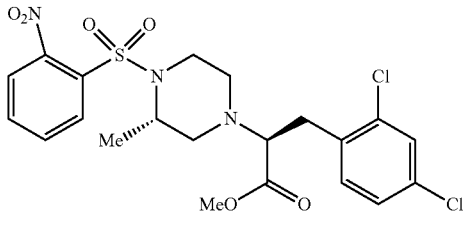 [SMILES: COC(=O)[C@H](Cc1ccc(Cl)cc1Cl)N1CCN(S(=O)(=O)c2ccccc2[N+](=O)[O-])[C@@H](C)C1] |

TABLE 18-continued
| PEx | Str |
|---|---|
| 123 | |
| 124 | |
| 125 | |
| 126 | |
| 127 | |
| 128 | |
| 129 | |
| 130 | |
TABLE 19
| PEx | Str |
|---|---|
| 131 | |
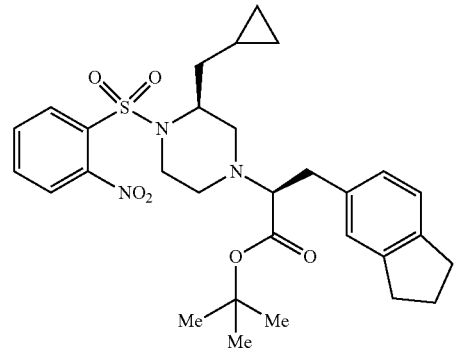 [SMILES: CC(C)(C)OC(=O)[C@H](Cc1ccc2c(c1)CCC2)N1CCN(S(=O)(=O)c2ccccc2[N+](=O)[O-])[C@@H](CC2CC2)C1]

TABLE 19-continued

| PEx | Str |
|---|---|
| 132 | |
| 133 | |
| 134 | |
| 135 | |
| 136 | |

TABLE 19-continued

| PEx | Str |
|---|---|
| 137 | |
| 138 | |
| 139 | |
| 140 | |

TABLE 20

| PEx | Str |
|---|---|
| 141 | |

TABLE 20-continued
| PEx | Str |
|---|---|
| 142 | |
| 143 | |
| 144 | |
| 145 | |
| 146 | |
| 147 | |
| 148 | |
| 149 | |
| 150 | |
TABLE 21
| PEx | Str |
|---|---|
| 151 | |
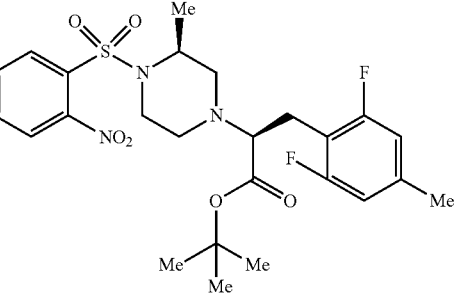

TABLE 21-continued
| PEx | Str |
|---|---|
| 152 | 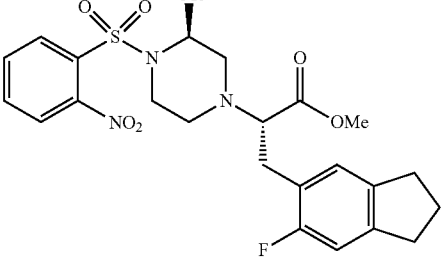 |
| 153 | 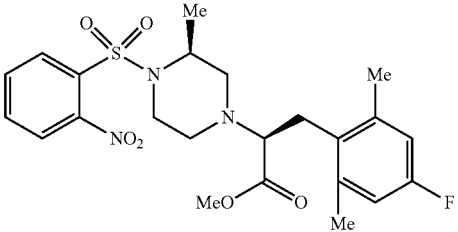 [SMILES: COC(=O)[C@H](Cc1c(C)cc(F)cc1C)N1CCN(S(=O)(=O)c2ccccc2[N+](=O)[O-])[C@@H](C)C1] |
| 154 | 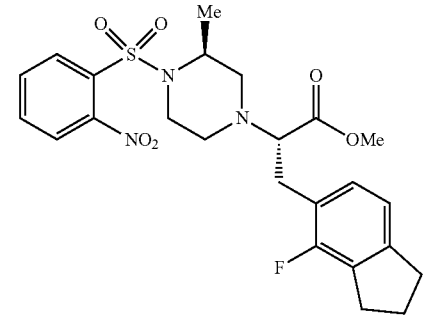 [SMILES: COC(=O)[C@H](Cc1ccc2c(c1F)CCC2)N1CCN(S(=O)(=O)c2ccccc2[N+](=O)[O-])[C@@H](C)C1] |
| 155 | 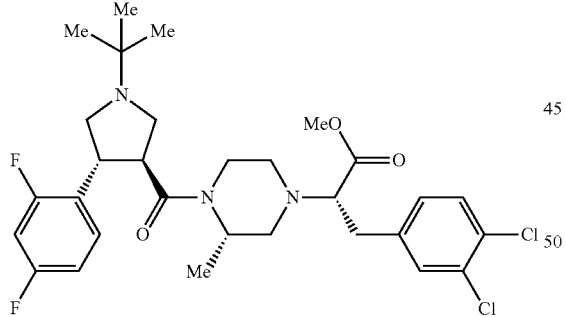 |
| 156 | 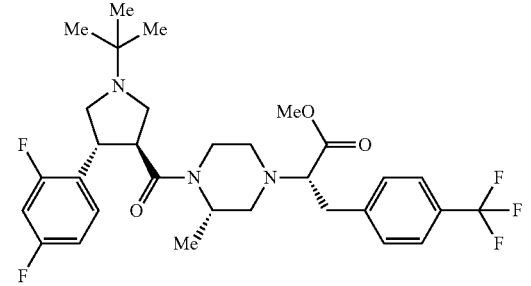 [SMILES: COC(=O)[C@H](Cc1ccc(C(F)(F)F)cc1)N1CCN(C(=O)[C@@H]2CN(C(C)(C)C)C[C@H]2c2ccc(F)cc2F)[C@@H](C)C1] |
| 157 | 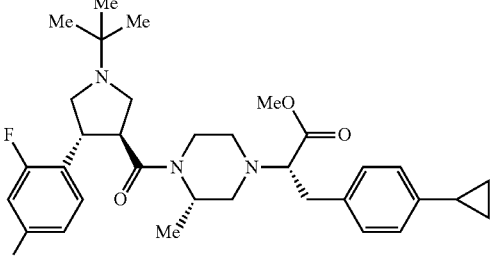 |
| 158 | 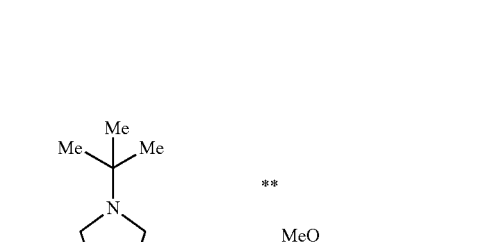 |
| 159 | 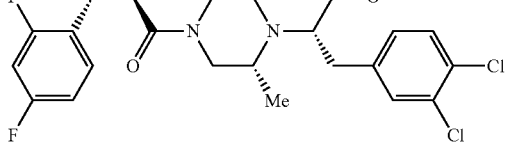 |
| 160 |  |

TABLE 22
| PEx | Str |
|---|---|
| 161 | 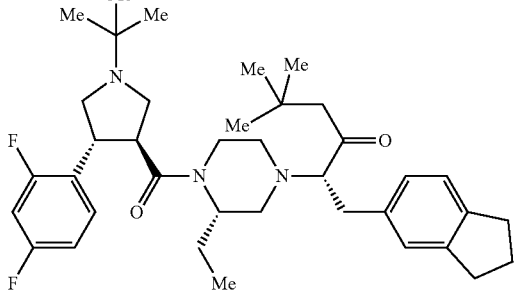 |
| 162 | 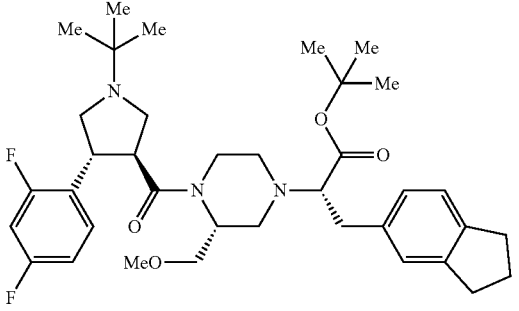 [SMILES: COC[C@H]1CN([C@@H](Cc2ccc3c(c2)CCC3)C(=O)OC(C)(C)C)CCN1C(=O)[C@@H]1CN(C(C)(C)C)C[C@H]1c1ccc(F)cc1F] |
| 163 | 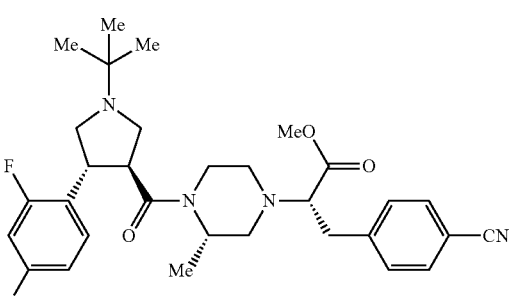 |
| 164 | 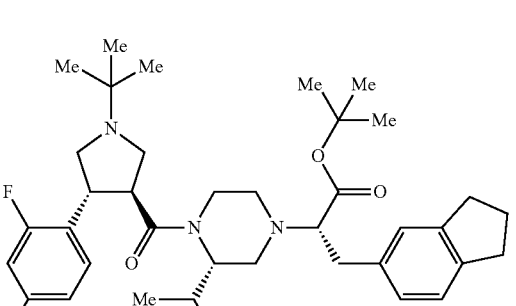 |
TABLE 22-continued
| PEx | Str |
|---|---|
| 165 | 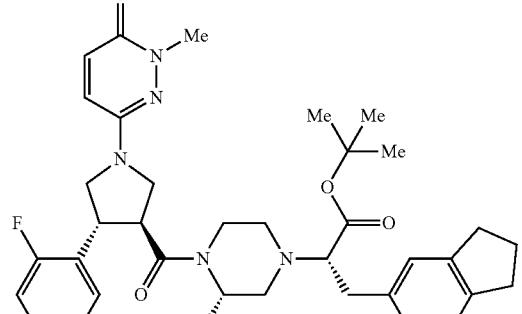 |
| 166 | 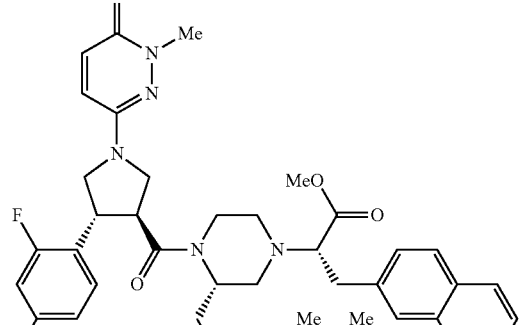 |
| 167 | 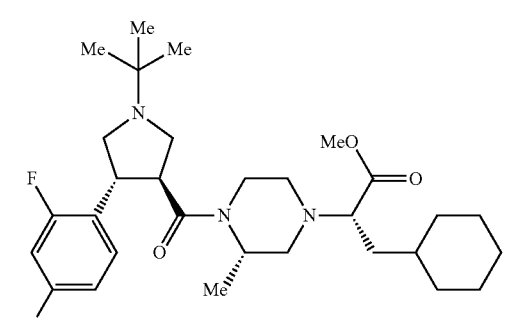 |
| 168 | 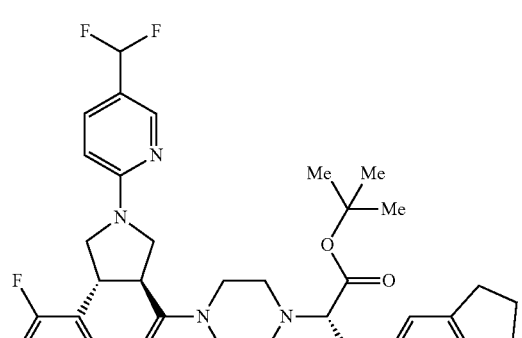 |

TABLE 22-continued
| PEx | Str |
|---|---|
| 169 | 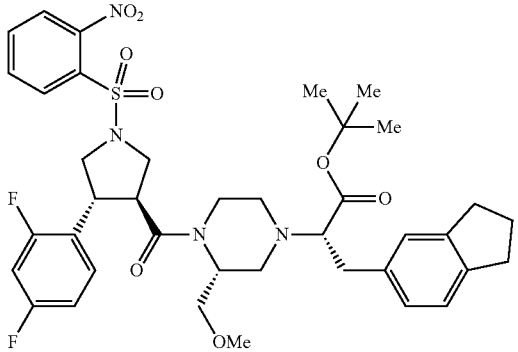 [SMILES: COC[C@H]1CN([C@@H](Cc2ccc3c(c2)CCC3)C(=O)OC(C)(C)C)CCN1C(=O)[C@@H]1CN(S(=O)(=O)c2ccccc2[N+](=O)[O-])C[C@H]1c1ccc(F)cc1F] |
| 170 | 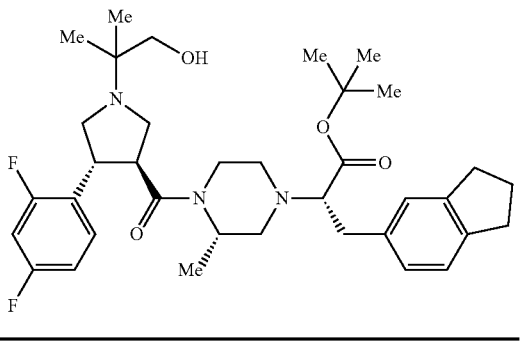 |
TABLE 23
| PEx | Str |
|---|---|
| 171 | 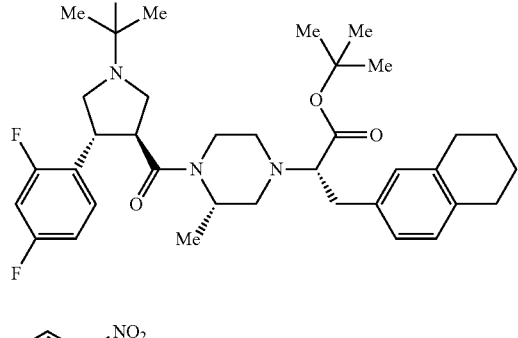 |
| 172 | 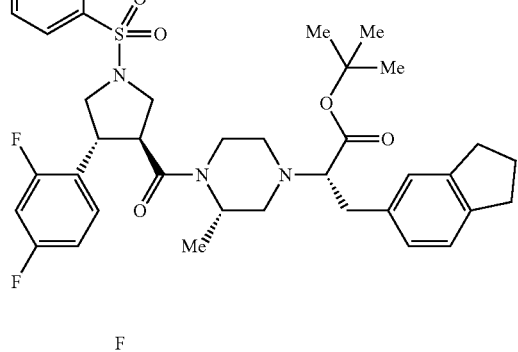 |
TABLE 23-continued
| PEx | Str |
|---|---|
| 173 | 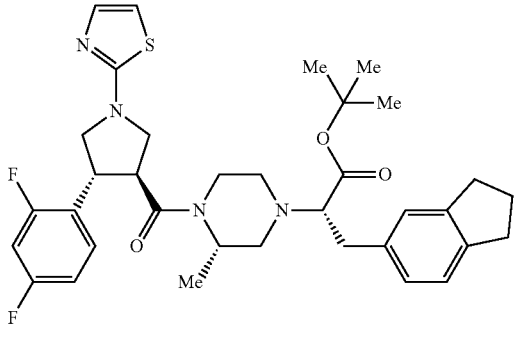 [SMILES: C[C@H]1CN([C@@H](Cc2ccc3c(c2)CCC3)C(=O)OC(C)(C)C)CCN1C(=O)[C@@H]1CN(c2nccs2)C[C@H]1c1ccc(F)cc1F] |
| 174 | 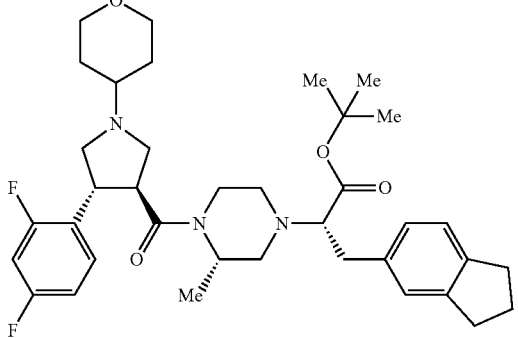 |
| 175 | 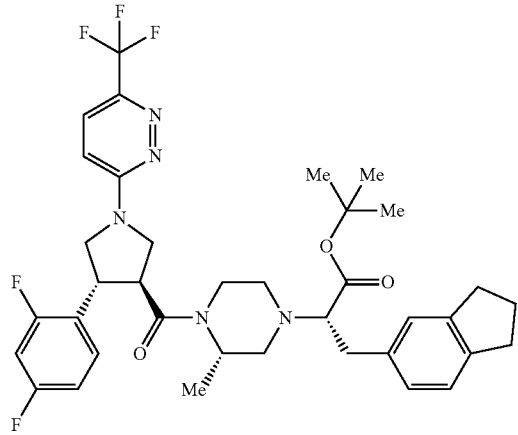 [SMILES: C[C@H]1CN([C@@H](Cc2ccc3c(c2)CCC3)C(=O)OC(C)(C)C)CCN1C(=O)[C@@H]1CN(c2ccc(C(F)(F)F)nn2)C[C@H]1c1ccc(F)cc1F] |
| 176 | 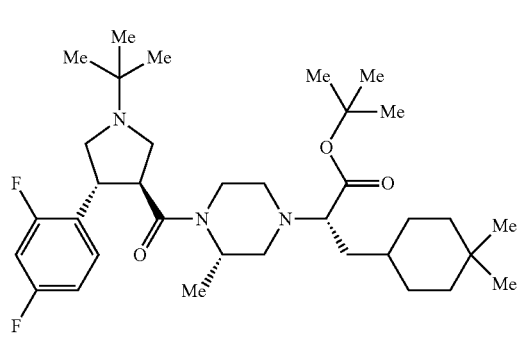 [SMILES: C[C@H]1CN([C@@H](CC2CCC(C)(C)CC2)C(=O)OC(C)(C)C)CCN1C(=O)[C@@H]1CN(C(C)(C)C)C[C@H]1c1ccc(F)cc1F] |

TABLE 23-continued

| PEx | Str |
|---|---|
| 177 | |
| 178 | |
| 179 | |
| 180 | |

TABLE 24

| PEx | Str |
|---|---|
| 181 | |
| 182 | |
| 183 | |
| 184 | |
| 185 | |

TABLE 24-continued
| PEx | Str |
|---|---|
| 186 | 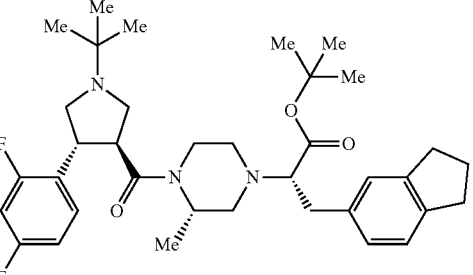 |
| 187 | 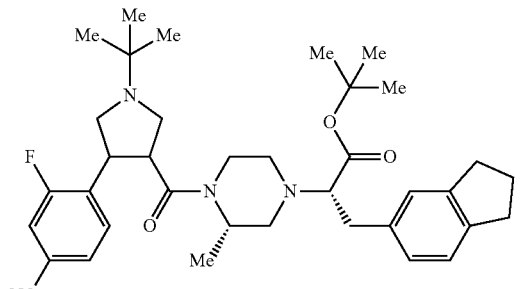 |
| 188 | 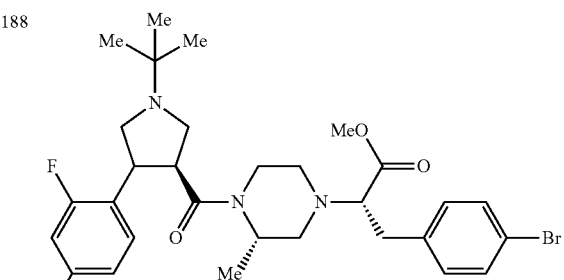 |
| 189 | 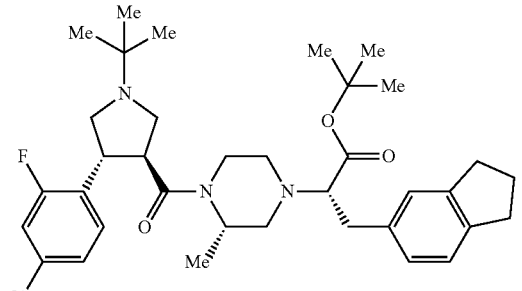 |
TABLE 24-continued
| PEx | Str |
|---|---|
| 190 | 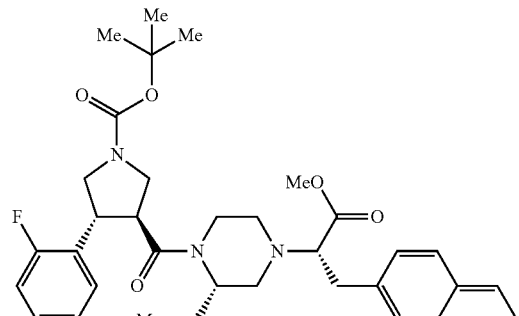 |
TABLE 25
| PEx | Str |
|---|---|
| 191 | 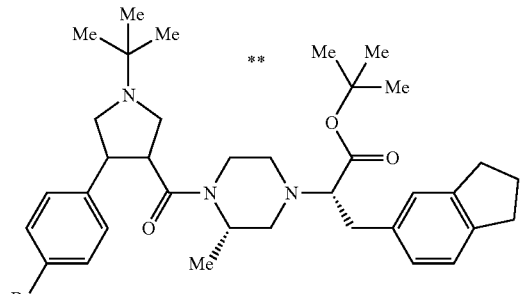 |
| 192 | 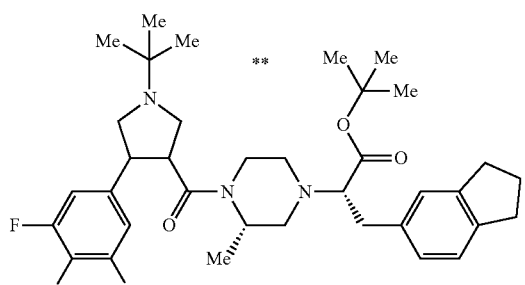 |
| 193 | 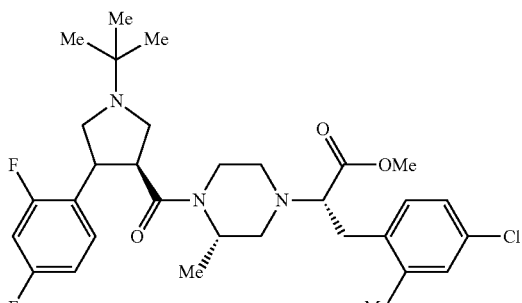 |

TABLE 25-continued
| PEx | Str |
|---|---|
| 194 | 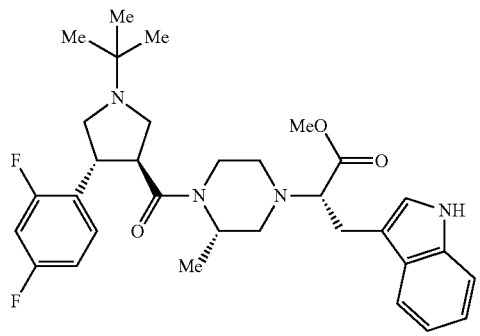 [SMILES: COC(=O)[C@H](Cc1c[nH]c2ccccc12)N1CCN(C(=O)[C@@H]2CN(C(C)(C)C)C[C@H]2c2ccc(F)cc2F)[C@@H](C)C1] |
| 195 | 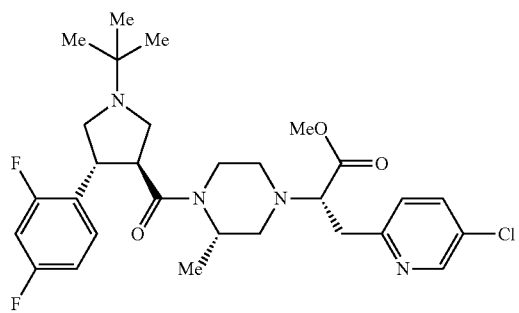 [SMILES: COC(=O)[C@H](Cc1ccc(Cl)cn1)N1CCN(C(=O)[C@@H]2CN(C(C)(C)C)C[C@H]2c2ccc(F)cc2F)[C@@H](C)C1] |
| 196 | 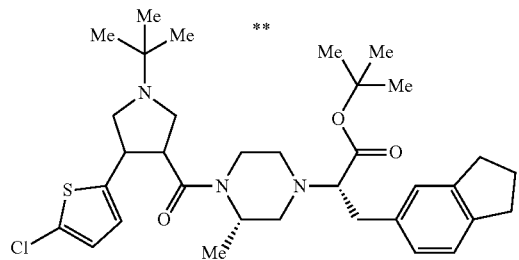 [SMILES: C[C@H]1CN([C@@H](Cc2ccc3c(c2)CCC3)C(=O)OC(C)(C)C)CCN1C(=O)C1CN(C(C)(C)C)CC1c1ccc(Cl)s1] |
| 197 | 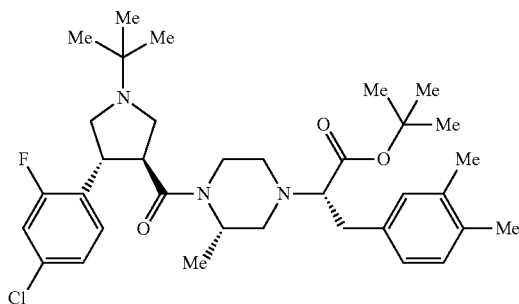 [SMILES: Cc1ccc(C[C@@H](C(=O)OC(C)(C)C)N2CCN(C(=O)[C@@H]3CN(C(C)(C)C)C[C@H]3c3ccc(Cl)cc3F)[C@@H](C)C2)cc1C] |
| 198 | 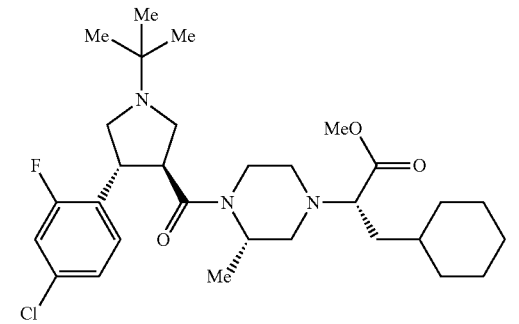 [SMILES: COC(=O)[C@H](CC1CCCCC1)N1CCN(C(=O)[C@@H]2CN(C(C)(C)C)C[C@H]2c2ccc(Cl)cc2F)[C@@H](C)C1] |
| 199 | 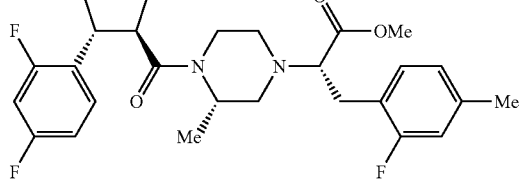 |
| 200 | 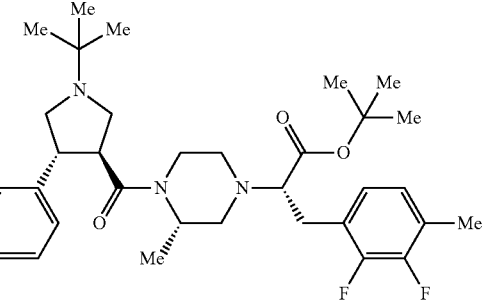 |
TABLE 26
| PEx | Str |
|---|---|
| 201 | 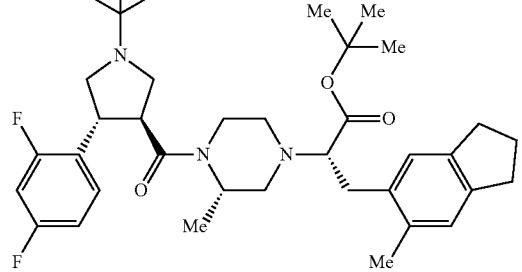 |
| 202 | 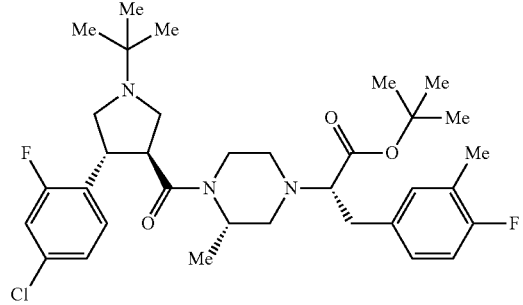 [SMILES: Cc1cc(C[C@@H](C(=O)OC(C)(C)C)N2CCN(C(=O)[C@@H]3CN(C(C)(C)C)C[C@H]3c3ccc(Cl)cc3F)[C@@H](C)C2)ccc1F] |

TABLE 26-continued

| PEx | Str |
|---|---|
| 203 | (structure) |
| 204 | (structure) |
| 205 | (structure) ** |
| 206 | (structure) |
| 207 | (structure) ** |
| 208 | (structure) # |
| 209 | (structure) |
| 210 | (structure) |

TABLE 27

| PEx | Str |
|---|---|
| 211 | (structure) |

TABLE 27-continued

| PEx | Str |
|---|---|
| 212 | (structure) |
| 213 | (structure) # |
| 214 | (structure) |
| 215 | (structure) |
| 216 | (structure) |
| 217 | (structure) |
| 218 | (structure) |
| 219 | (structure) |
| 220 | (structure) # |

TABLE 28

| PEx | Str |
|---|---|
| 221 | |
| 222 | |
| 223 | |
| 224 | |
| 225 | |

TABLE 28-continued

| PEx | Str |
|---|---|
| 226 | |
| 227 | |
| 228 | |
| 229 | |
| 230 | |

TABLE 29

| PEx | Str |
|---|---|
| 231 | |

TABLE 29-continued

| PEx | Str |
|---|---|
| 232 | (structure) |
| 233 | (structure) |
| 234 | (structure) |
| 235 | (structure) |
| 236 | (structure) |
| 237 | (structure) |
| 238 | (structure) # |
| 239 | (structure) |
| 240 | (structure) |

TABLE 30

| PEx | Str |
|---|---|
| 241 | (structure) |
| 242 | (structure) |

TABLE 30-continued

| PEx | Str |
|---|---|
| 243 | |
| 244 | |
| 245 | |
| 246 | |
| 247 | |
| 248 | |

TABLE 30-continued

| PEx | Str |
|---|---|
| 249 | |
| 250 | # |

TABLE 31

| PEx | Str |
|---|---|
| 251 | |
| 252 | |
| 253 | |

TABLE 31-continued

| PEx | Str |
|---|---|
| 254 | (structure) |
| 255 | (structure) |
| 256 | (structure) |
| 257 | (structure) |
| 258 | (structure) |
| 259 | (structure) |
| 260 | (structure) |

TABLE 32

| PEx | Str |
|---|---|
| 261 | (structure) |
| 262 | (structure) |
| 263 | (structure) # |
| 264 | (structure) |

TABLE 32-continued

| PEx | Str |
|---|---|
| 265 | (structure) |
| 266 | (structure) |
| 267 | (structure) |
| 268 | (structure) |
| 269 | (structure) |
| 270 | (structure) |

TABLE 33

| PEx | Str |
|---|---|
| 271 | (structure) |
| 272 | (structure) |
| 273 | (structure) |
| 274 | (structure) |
| 275 | (structure) |
| 276 | (structure) |

TABLE 33-continued
| PEx | Str |
|---|---|
| 277 | 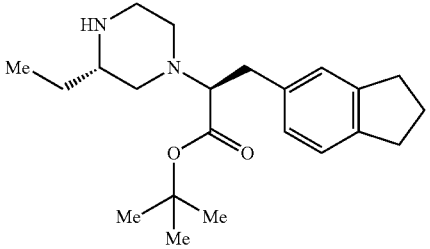 [SMILES: CC[C@H]1CN([C@@H](Cc2ccc3c(c2)CCC3)C(=O)OC(C)(C)C)CCN1] |
| 278 | 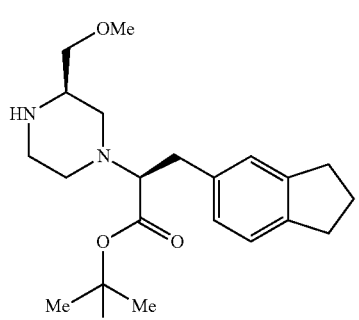 |
| 279 | 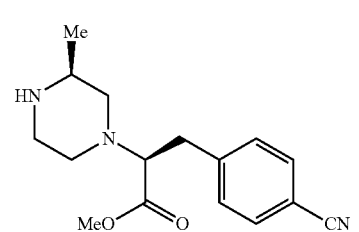 [SMILES: COC(=O)[C@H](Cc1ccc(C#N)cc1)N1CCN[C@@H](C)C1] |
| 280 | 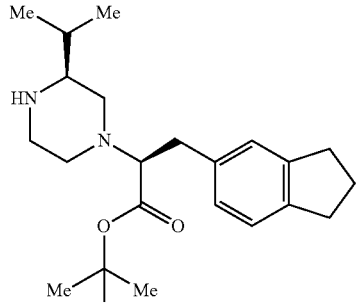 |
TABLE 34
| PEx | Str |
|---|---|
| 281 | 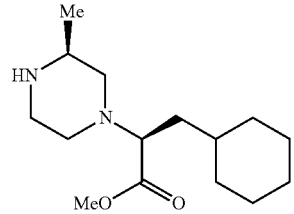 [SMILES: COC(=O)[C@H](CC1CCCCC1)N1CCN[C@@H](C)C1] |
| 282 | 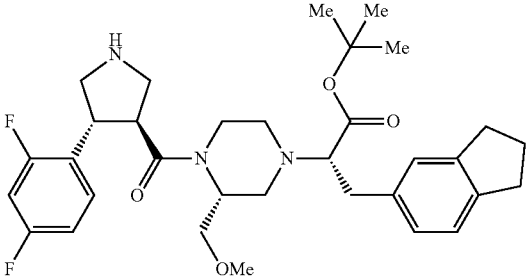 [SMILES: COC[C@H]1CN([C@@H](Cc2ccc3c(c2)CCC3)C(=O)OC(C)(C)C)CCN1C(=O)[C@@H]1CNC[C@H]1c1ccc(F)cc1F] |
| 283 | 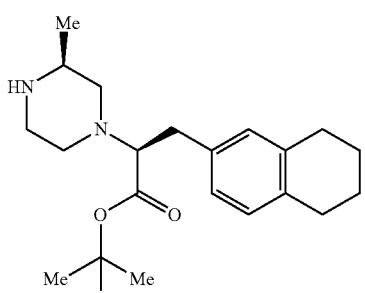 |
| 284 | 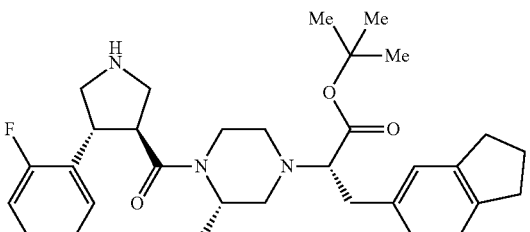 |
| 285 | 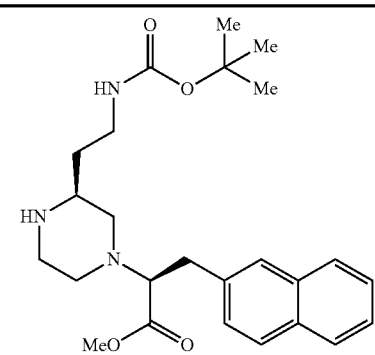 |
| 286 | 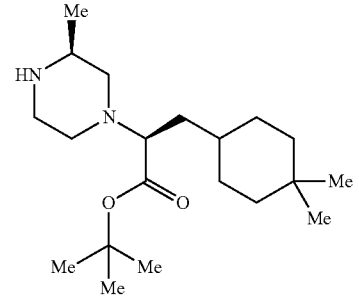 [SMILES: C[C@H]1CN([C@@H](CC2CCC(C)(C)CC2)C(=O)OC(C)(C)C)CCN1] |

TABLE 34-continued

| PEx | Str |
|---|---|
| 287 | (structure) |
| 288 | (structure) |
| 289 | (structure) |
| 290 | (structure) |

TABLE 35

| PEx | Str |
|---|---|
| 291 | (structure) |
| 292 | (structure) |
| 293 | (structure) |
| 294 | (structure) |
| 295 | (structure) |
| 296 | (structure) |
| 297 | (structure) |

| PEx | Str |
|---|---|
| 298 | 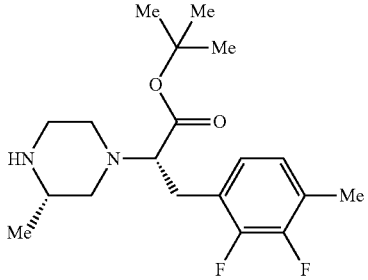 [SMILES: Cc1ccc(C[C@@H](C(=O)OC(C)(C)C)N2CCN[C@@H](C)C2)c(F)c1F] |
| 299 | 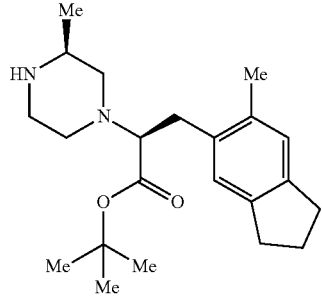 [SMILES: Cc1cc2c(cc1C[C@@H](C(=O)OC(C)(C)C)N1CCN[C@@H](C)C1)CCC2] |
| 300 | 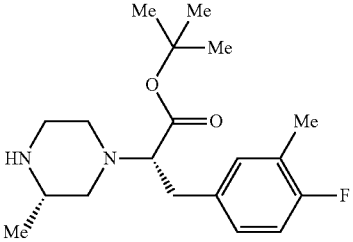 [SMILES: Cc1cc(C[C@@H](C(=O)OC(C)(C)C)N2CCN[C@@H](C)C2)ccc1F] |
TABLE 36
| PEx | Str |
|---|---|
| 301 | 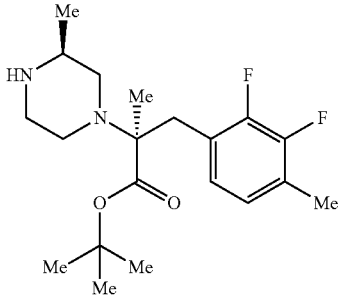 [SMILES: Cc1ccc(C[C@@](C)(C(=O)OC(C)(C)C)N2CCN[C@@H](C)C2)c(F)c1F] |
| 302 | 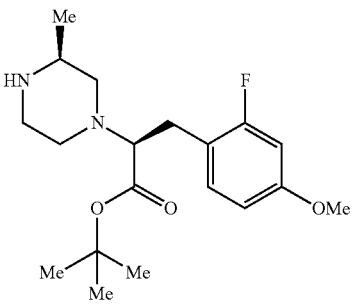 [SMILES: COc1ccc(C[C@@H](C(=O)OC(C)(C)C)N2CCN[C@@H](C)C2)c(F)c1] # |
| 303 | 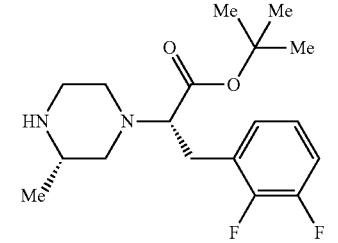 [SMILES: C[C@H]1CN([C@@H](Cc2cccc(F)c2F)C(=O)OC(C)(C)C)CCN1] |
| 304 |  |
| 305 | 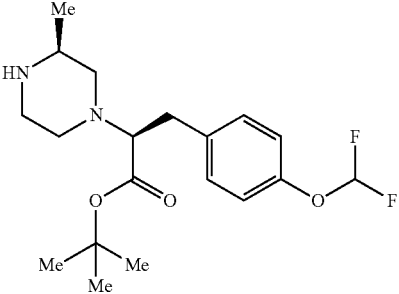 [SMILES: C[C@H]1CN([C@@H](Cc2ccc(OC(F)F)cc2)C(=O)OC(C)(C)C)CCN1] |
| 306 |  |
| 307 | 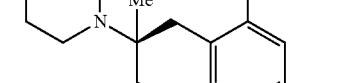 |

TABLE 36-continued

| PEx | Str |
|---|---|
| 308 | (structure) |
| 309 | (structure) |
| 310 | (structure) |

TABLE 37

| PEx | Str |
|---|---|
| 311 | (structure) |
| 312 | (structure) |

TABLE 37-continued

| PEx | Str |
|---|---|
| 313 | (structure) |
| 314 | (structure) |
| 315 | (structure) |
| 316 | (structure) |
| 317 | (structure) |
| 318 | (structure) |

TABLE 37-continued

| PEx | Str |
|---|---|
| 319 | (structure) |
| 320 | (structure) |

TABLE 38

| PEx | Str |
|---|---|
| 321 | (structure) |
| 322 | (structure) |
| 323 | (structure) |
| 324 | (structure) |

TABLE 38-continued

| PEx | Str |
|---|---|
| 325 | (structure) |
| 326 | (structure) |
| 327 | (structure) |
| 328 | (structure) |
| 329 | (structure) |
| 330 | (structure) |

TABLE 39

| PEx | Str |
|---|---|
| 331 | (structure) |
| 332 | (structure) |
| 333 | (structure) |
| 334 | (structure) |
| 335 | (structure) $ |
| 336 | (structure) $ |

TABLE 39-continued

| PEx | Str |
|---|---|
| 337 | (structure) |
| 338 | (structure) |
| 339 | (structure) |
| 340 | (structure) ** |

TABLE 40
| PEx | Str |
|---|---|
| 341 | 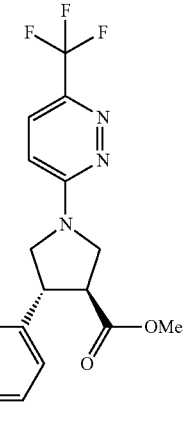 |
| 342 | 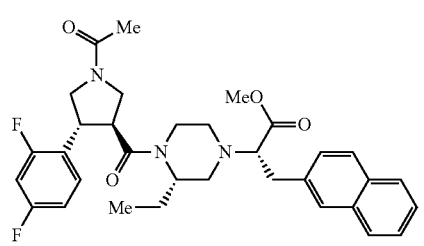 [SMILES: CC[C@H]1CN([C@@H](Cc2ccc3ccccc3c2)C(=O)OC)CCN1C(=O)[C@@H]1CN(C(C)=O)C[C@H]1c1ccc(F)cc1F] |
| 343 | 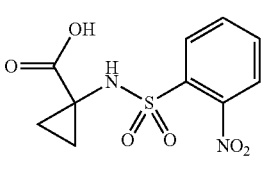 [SMILES: O=C(O)C1(NS(=O)(=O)c2ccccc2[N+](=O)[O-])CC1] |
| 344 | 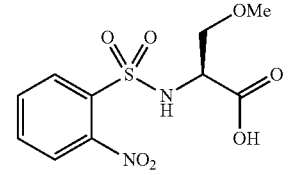 [SMILES: COC[C@H](NS(=O)(=O)c1ccccc1[N+](=O)[O-])C(=O)O] |
| 345 | 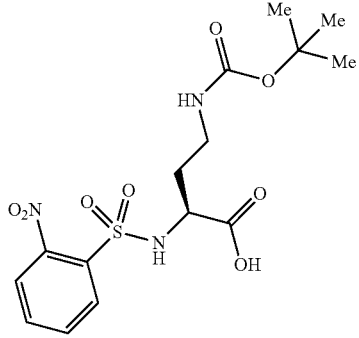 [SMILES: CC(C)(C)OC(=O)NCC[C@H](NS(=O)(=O)c1ccccc1[N+](=O)[O-])C(=O)O] |
TABLE 40-continued
| PEx | Str |
|---|---|
| 346 | 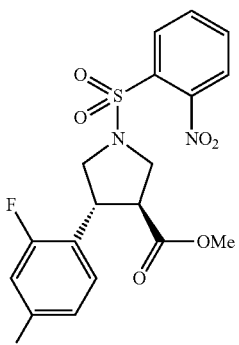 |
| 347 | 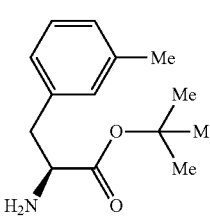 |
| 348 | 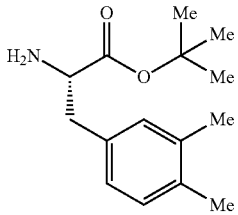 [SMILES: Cc1ccc(C[C@H](N)C(=O)OC(C)(C)C)cc1C] |
| 349 | 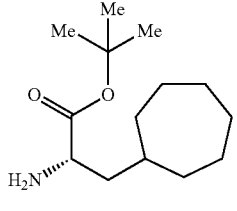 |
| 350 | 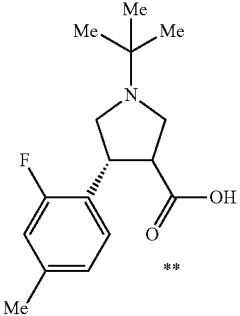 [SMILES: Cc1ccc([C@@H]2CN(C(C)(C)C)CC2C(=O)O)c(F)c1] |

TABLE 41

| PEx | Str |
|---|---|
| 351 | (structure) |
| 352 | (structure) |
| 353 | (structure) |
| 344 | (structure) |
| 345 | (structure) |

TABLE 41-continued

| PEx | Str |
|---|---|
| 356 | (structure) |
| 357 | (structure) |
| 358 | (structure) |
| 359 | (structure) |

TABLE 41-continued
| PEx | Str |
|---|---|
| 360 | 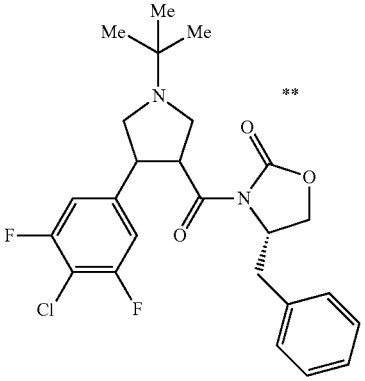 [SMILES: CC(C)(C)N1CC(C(=O)N2C(=O)OC[C@@H]2Cc2ccccc2)C(c2cc(F)c(Cl)c(F)c2)C1] |
TABLE 42
| PEx | Str |
|---|---|
| 361 | |
| 362 | |
| 363 | |
| 364 | |
| 365 | |
| 366 | |

TABLE 42-continued
| PEx | Str |
|---|---|
| 367 | 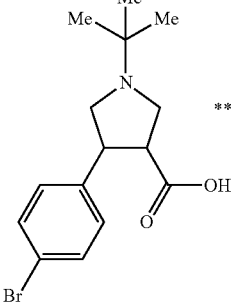 |
| 368 | 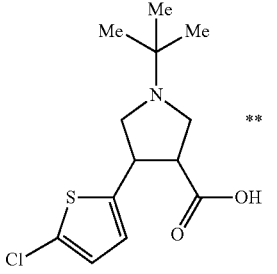 [SMILES: CC(C)(C)N1CC(C(=O)O)C(c2ccc(Cl)s2)C1] |
| 369 | 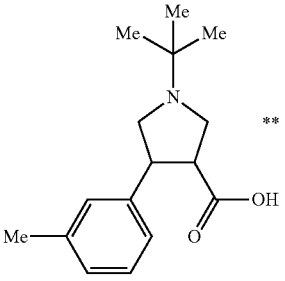 [SMILES: Cc1cccc(C2CN(C(C)(C)C)CC2C(=O)O)c1] |
| 370 | 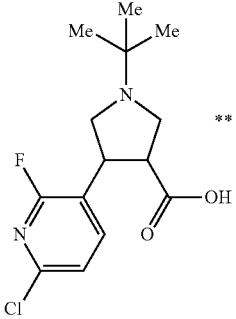 [SMILES: CC(C)(C)N1CC(C(=O)O)C(c2ccc(Cl)nc2F)C1] |
TABLE 43
| PEx | Str |
|---|---|
| 371 | 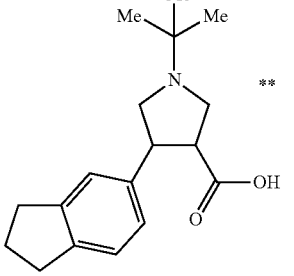 |
| 372 | 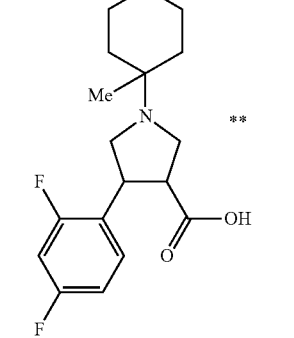 |
| 373 | 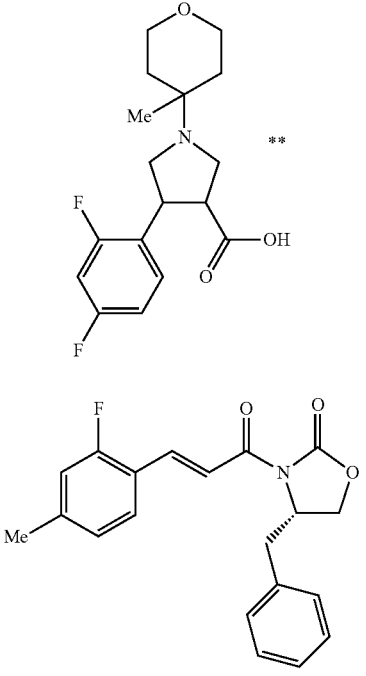 |
| 374 | 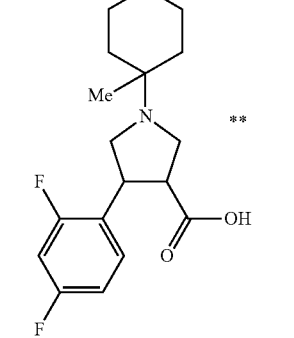 |
| 375 | 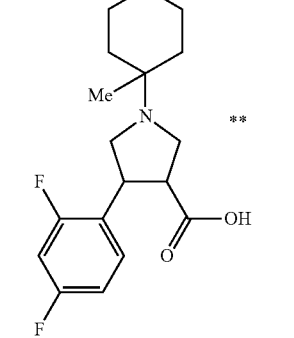 |

US 10,301,286 B2
131
TABLE 43-continued
| PEx | Str |
|---|---|
| 376 | 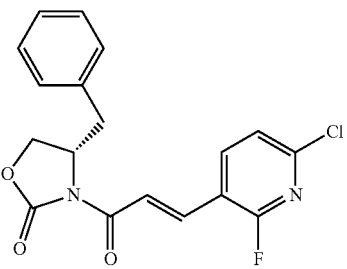 [SMILES: O=C(/C=C/c1ccc(Cl)nc1F)N1C(=O)OC[C@@H]1Cc1ccccc1] |
| 377 | 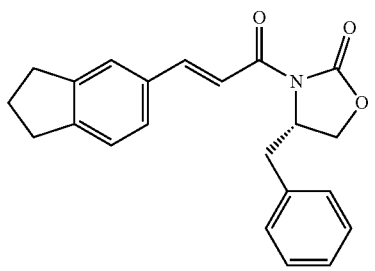 [SMILES: O=C(/C=C/c1ccc2c(c1)CCC2)N1C(=O)OC[C@@H]1Cc1ccccc1] |
| 378 | 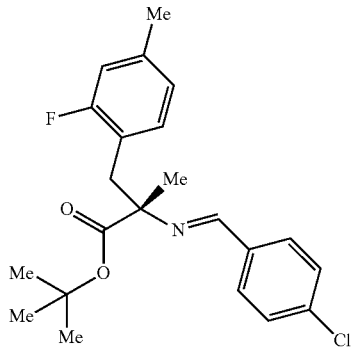 [SMILES: Cc1ccc(C[C@](C)(/N=C/c2ccc(Cl)cc2)C(=O)OC(C)(C)C)c(F)c1] |
| 379 | 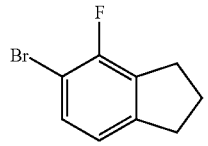 |
| 380 | 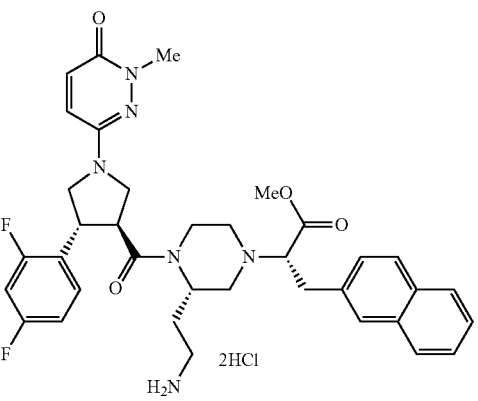 [SMILES: COC(=O)[C@H](Cc1ccc2ccccc2c1)N1CCN(C(=O)[C@@H]2CN(c3ccc(=O)n(C)n3)C[C@H]2c2ccc(F)cc2F)[C@@H](CCN)C1] |
132
TABLE 44
| PEx | Str |
|---|---|
| 381 | 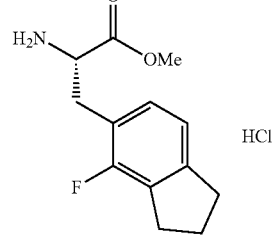 |
| 382 | 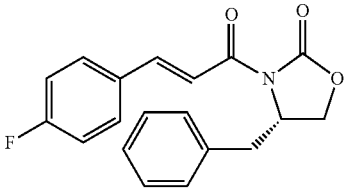 [SMILES: O=C(/C=C/c1ccc(F)cc1)N1C(=O)OC[C@@H]1Cc1ccccc1] |
| 383 | 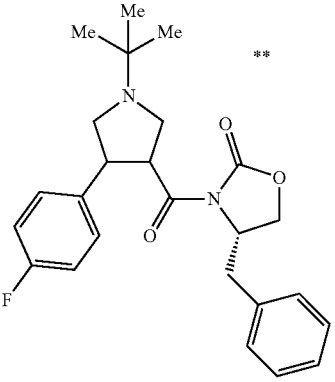 [SMILES: CC(C)(C)N1CC(C(=O)N2C(=O)OC[C@@H]2Cc2ccccc2)C(c2ccc(F)cc2)C1] |
| 384 | 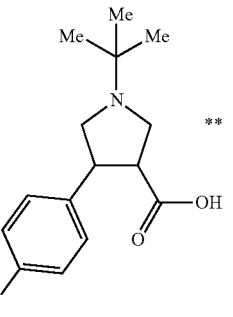 |
| 385 | 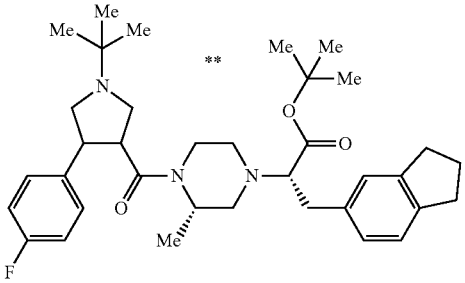 [SMILES: C[C@H]1CN([C@@H](Cc2ccc3c(c2)CCC3)C(=O)OC(C)(C)C)CCN1C(=O)C1CN(C(C)(C)C)CC1c1ccc(F)cc1] |

TABLE 44-continued
| PEx | Str |
|---|---|
| 386 | 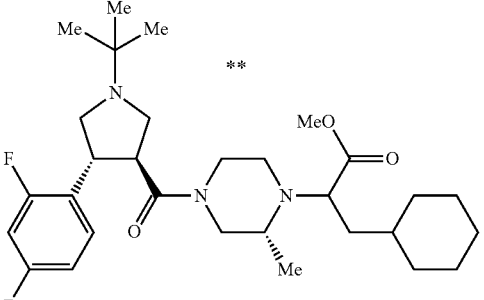 ** |
| 387 | 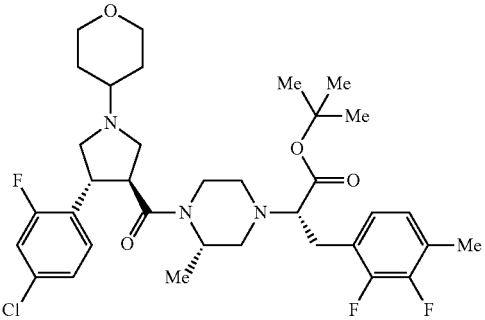 [SMILES: Cc1ccc(C[C@@H](C(=O)OC(C)(C)C)N2CCN(C(=O)[C@@H]3CN(C4CCOCC4)C[C@H]3c3ccc(Cl)cc3F)[C@@H](C)C2)c(F)c1F] |
| 388 | 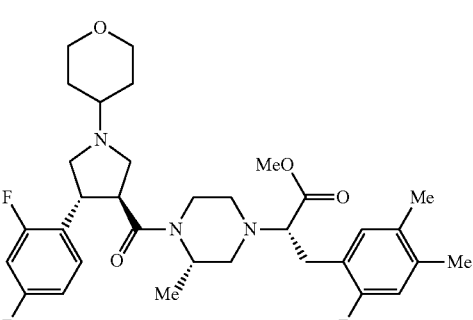 |
| 389 | 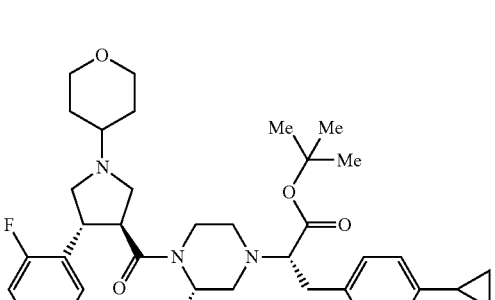 |
TABLE 44-continued
| PEx | Str |
|---|---|
| 390 | 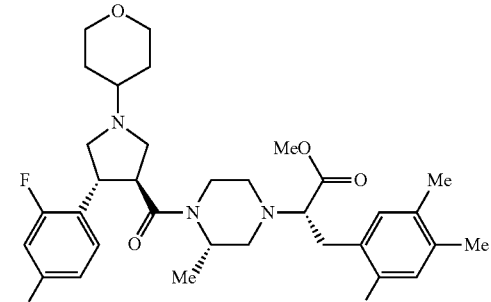 |
TABLE 45
| PEx | Str |
|---|---|
| 391 | 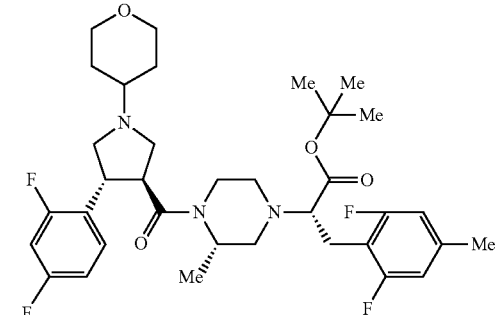 |
| 392 | 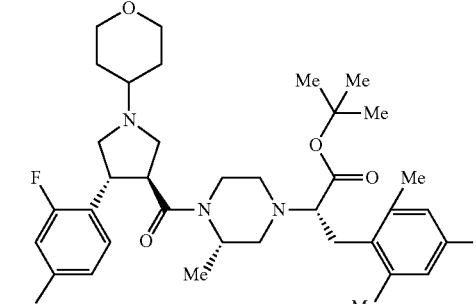 |
| 393 | 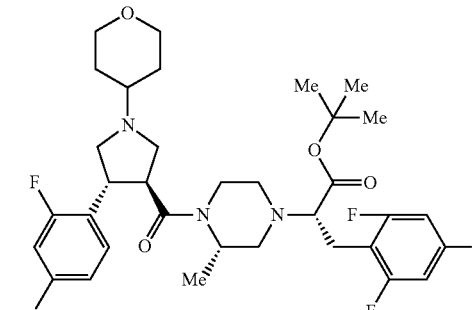 |

TABLE 45-continued

| PEx | Str |
|---|---|
| 394 | (structure) |
| 395 | (structure) |
| 396 | (structure) |
| 397 | (structure) |
| 398 | (structure) |
| 399 | (structure) |
| 400 | (structure) |

TABLE 46

| PEx | Str |
|---|---|
| 401 | (structure) |
| 402 | (structure) |
| 403 | (structure) |
| 404 | (structure) |

TABLE 46-continued

| PEx | Str |
|---|---|
| 405 | (structure) |
| 406 | (structure) |
| 407 | (structure) |
| 408 | (structure) |
| 409 | (structure) |

TABLE 46-continued

| PEx | Str |
|---|---|
| 410 | (structure) |

TABLE 47

| PEx | Str |
|---|---|
| 411 | (structure) |
| 412 | (structure) |
| 413 | (structure) |
| 414 | (structure) 2HCl |

TABLE 47-continued
| PEx | Str |
|---|---|
| 415 | 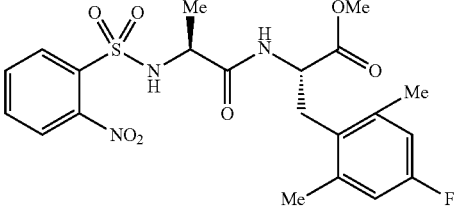 [SMILES: COC(=O)[C@H](Cc1c(C)cc(F)cc1C)NC(=O)[C@H](C)NS(=O)(=O)c1ccccc1[N+](=O)[O-]] |
| 416 | 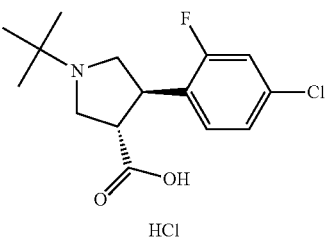 [SMILES: CC(C)(C)N1C[C@@H](C(=O)O)[C@H](c2ccc(Cl)cc2F)C1 ; Cl] |
| 417 | 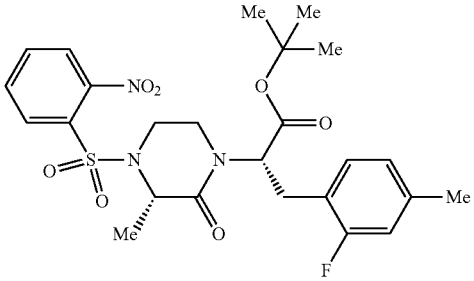 [SMILES: Cc1ccc(C[C@@H](C(=O)OC(C)(C)C)N2CCN(S(=O)(=O)c3ccccc3[N+](=O)[O-])[C@@H](C)C2=O)c(F)c1] |
| 418 | 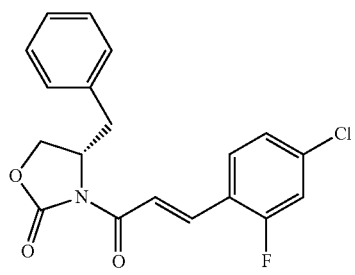 [SMILES: O=C(/C=C/c1ccc(Cl)cc1F)N1C(=O)OC[C@@H]1Cc1ccccc1] |
| 419 | 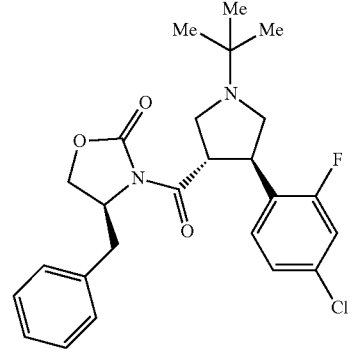 [SMILES: CC(C)(C)N1C[C@@H](C(=O)N2C(=O)OC[C@@H]2Cc2ccccc2)[C@H](c2ccc(Cl)cc2F)C1] |
TABLE 47-continued
| PEx | Str |
|---|---|
| 420 | 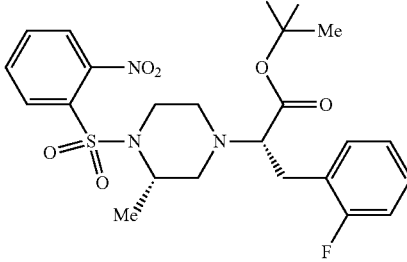 |
TABLE 48
| PEx | Str |
|---|---|
| 421 | 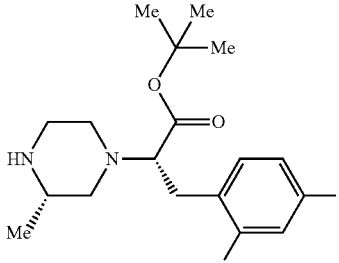 |
TABLE 49
| PEx | PSyn | DAT |
|---|---|---|
| 1 | 1 | EI: 208 |
| 2 | 2 | ESI+: 274 |
| 3 | 3 | ESI+: 327 |
| 4 | 4 | ESI+: 309 |
| 5 | 5 | ESI+: 328 |
| 6 | 6 | ESI+: 334 [M + Na]+ |
| 7 | 7 | APCI/ESI+: 468 |
| 8 | 8 | APCI/ESI+: 494 |
| 9 | 9 | APCI/ESI+: 480 |
| 10 | 10 | APCI/ESI+: 295 |
| 11 | 11 | APCI/ESI+: 604 |
| 12 | 12 | $^1$H-NMR (400 MHz, CDCl$_3$) δ ppm 2.30 (3H, s) 2.38 (3H, s) 4.55 (2H, d, J = 1.2 Hz) 6.73 (1H, d, J = 10.8 Hz) 6.80 (1H, s) |
| 13 | 13 | ESI+: 432 |
| 14 | 14 | ESI+: 268 |
| 15 | 15 | ESI+: 546 [M + Na]+ |
| 16 | 16 | ESI+: 305 |
| 17 | 17 | ESI−: 476 |
| 18 | 18 | ESI+: 262 |
| 19 | 19 | ESI+: 502 |
| 20 | 20 | ESI+: 327 |
| 21 | 21 | ESI+: 431 |
| 22 | 22 | ESI+: 299 [M − OMe]+ |
| 23 | 23 | ESI+: 473 |
| 24 | 24 | ESI+: 688 |
| 25 | 25 | ESI+: 355 |
| 26 | 26 | ESI+: 413 |
| 27 | 27 | ESI+: 678 |
| 28 | 28 | ESI+: 325 |
| 29 | 29 | ESI+: 256 |
| 30 | 30 | ESI+: 622 |
| 31 | 31 | ESI+: 315 |
| 32 | 32 | ESI+: 278 |
| 33 | 33 | APCI/ESI+: 606 |
| 34 | 34 | ESI+: 343 |

TABLE 50

| PEx | PSyn | DAT |
|---|---|---|
| 35 | 35 | ESI+: 297 |
| 36 | 36 | ESI+: 283 |
| 37 | 37 | ESI+: 338 |
| 38 | 38 | ESI+: 437 |
| 39 | 39 | ESI+: 278 |
| 40 | 40 | $^1$H-NMR (400 MHz, DMSO-d6) δ ppm 1.23 (3H, d, J = 6.4 Hz) 1.34 (9H, s) 1.94-2.03 (2H, m) 2.50-2.63 (1H, m) 2.76-3.06 (9H, m) 3.14-3.28 (3H, m) 3.34-3.52 (1H, m) 6.95 (1H, d, J = 7.5 Hz) 7.06 (1H, s) 7.12 (1H, d, J = 7.6 Hz) |
| 41 | 41 | APCI/EST+: 351 |
| 42 | 42 | ESI+: 228 |
| 43 | 43 | ESI+: 408 |
| 44 | 44 | $^1$H-NMR (400 MHz, CDCl$_3$) δ ppm 2.75 (1H, dd, J = 5.5, 2.7 Hz) 3.17 (1H, dd, J = 5.7, 4.1 Hz) 4.09 (1H, dd, J = 3.9, 2.7 Hz) 7.06-7.14 (3H, m) |
| 45 | 45 | ESI+: 244 |
| 46 | 46 | EI: 214, 216 |
| 47 | 47 | ESI+: 238 |
| 48 | 48 | ESI+: 269 |
| 49 | 49 | ESI+: 485 |
| 50 | 8 | ESI+: 572 [M + Na]+ |
| 51 | 9 | ESI+: 536 |
| 52 | 16 | ESI+: 351 |
| 53 | 11 | ESI+: 660 |
| 54 | 8 | ESI+: 504 |
| 55 | 9 | ESI+: 490 |
| 56 | 11 | ESI+: 586 |
| 57 | 9 | ESI+: 526 |
| 58 | 16 | ESI+: 341 |
| 59 | 11 | ESI+: 606 |
| 60 | 17 | APCI/ESI−: 516 |
| 61 | 8 | ESI+: 544 |
| 62 | 9 | APCI/ESI+: 530 |
| 63 | 16 | APCI/ESI+: 345 |
| 64 | 11 | APCI/ESI+: 610 |

TABLE 51

| PEx | PSyn | DAT |
|---|---|---|
| 65 | 17 | ESI+: 464 |
| 66 | 8 | ESI+: 490 |
| 67 | 9 | ESI+: 476 |
| 68 | 16 | ESI+: 291 |
| 69 | 11 | ESI+: 573 |
| 70 | 15 | ESI+: 492 |
| 71 | 8 | ESI+: 518 |
| 72 | 9 | ESI+: 504 |
| 73 | 16 | ESI+: 319 |
| 74 | 11 | ESI+: 600 |
| 75 | 11 | ESI+: 576 |
| 76 | 3 | APCI/ESI+: 297 |
| 77 | 4 | APCI/ESI+: 279 |
| 78 | 5 | APCI/ESI+: 298 |
| 79 | 6 | ESI+: 360 [M + Na]+ |
| 80 | 6 | $^1$H-NMR (400 MHz, CDCl$_3$) δ ppm 1.19-1.42 (9H, m) 2.33 (6H, s) 2.93-3.09 (2H, m) 3.60-3.77 (3H, br) 4.40-4.59 (1H, m) 5.00-5.12 (1H, m) 6.72 (2H, d, J = 9.4 Hz) |
| 81 | 6 | ESI+: 360 [M + Na]+ |
| 82 | 8 | ESI+: 552 [M + Na]+ |
| 83 | 8 | ESI+: 530 |
| 84 | 8 | ESI+: 540 |
| 85 | 8 | ESI+: 524 |
| 86 | 8 | ESI+: 530 |
| 87 | 8 | ESI+: 580 [M + Na]+ |
| 88 | 8 | ESI+: 574 |
| 89 | 8 | ESI+: 594 [M + Na]+ |
| 90 | 8 | ESI+: 663 [M + Na]+ |
| 91 | 8 | ESI+: 468 |
| 92 | 8 | ESI+: 558 |

TABLE 51-continued

| PEx | PSyn | DAT |
|---|---|---|
| 93 | 8 | ESI+: 560 [M + Na]+ |
| 94 | 8 | ESI+: 606 [M + Na]+ |
| 95 | 8 | ESI+: 580 [M + Na]+ |
| 96 | 8 | ESI+: 582 [M + Na]+ |
| 97 | 8 | ESI+: 518 |

TABLE 52

| PEx | PSyn | DAT |
|---|---|---|
| 98 | 8 | ESI+: 610 [M + Na]+ |
| 99 | 8 | ESI+: 510 |
| 100 | 8 | ESI+: 501 |
| 101 | 8 | ESI+: 497 |
| 102 | 8 | ESI+: 554 [M + Na]+ |
| 103 | 8 | ESI+: 554 |
| 104 | 8 | ESI+: 558 |
| 105 | 8 | ESI+: 536 |
| 106 | 8 | ESI+: 536 |
| 107 | 8 | ESI+: 554 [M + Na]+ |
| 108 | 8 | ESI+: 590 [M + Na]+ |
| 109 | 8 | ESI+: 574 [M + Na]+ |
| 110 | 8 | ESI+: 540 |
| 111 | 8 | ESI+: 592 [M + Na]+ |
| 112 | 8 | ESI+: 572 [M + Na]+ |
| 113 | 8 | ESI+: 546 [M + Na]+ |
| 114 | 8 | ESI+: 554 |
| 115 | 8 | ESI+: 542 [M + Na]+ |
| 116 | 8 | APCI/ESI+: 508 |
| 117 | 8 | ESI+: 542 [M + Na]+ |
| 118 | 9 | ESI+: 516 |
| 119 | 9 | ESI+: 516 |
| 120 | 9 | ESI+: 488 |
| 121 | 9 | ESI+: 510 |
| 122 | 9 | ESI+: 516 |
| 123 | 9 | ESI+: 544 |
| 124 | 9 | ESI+: 560 |
| 125 | 9 | ESI+: 526, 528 |
| 126 | 9 | ESI+: 558 |
| 127 | 9 | ES1+: 627 |
| 128 | 9 | ESI+: 454 |
| 129 | 9 | ESI+: 544 |
| 130 | 9 | ESI+: 524 |
| 131 | 9 | ESI+: 570 |
| 132 | 9 | ESI+: 544 |

TABLE 53

| PEx | PSyn | DAT |
|---|---|---|
| 133 | 9 | ESI+: 546 |
| 134 | 9 | ESI+: 504 |
| 135 | 9 | ESI+: 574 |
| 136 | 9 | APCI/ESI+: 496 |
| 137 | 9 | ESI+: 487 |
| 138 | 9 | ESI+: 483 |
| 139 | 9 | ESI+: 518 |
| 140 | 9 | ESI+: 540 |
| 141 | 9 | ESI+: 544 |
| 142 | 9 | ESI+: 522 |
| 143 | 9 | ESI+: 522 |
| 144 | 9 | ESI+: 518 |
| 145 | 9 | ESI+: 554 |
| 146 | 9 | ESI+: 538 |
| 147 | 9 | ESI+: 526 |
| 148 | 9 | ESI+: 556 |
| 149 | 9 | ESI+: 536 |
| 150 | 9 | ESI+: 510 |
| 151 | 9 | ESI+: 540 |
| 152 | 9 | ESI+: 506 |
| 153 | 9 | APCI/ESI+: 494 |
| 154 | 9 | ESI+: 506 |
| 155 | 11 | ESI+: 596 |

TABLE 53-continued

| PEx | PSyn | DAT |
|---|---|---|
| 156 | 11 | ESI+: 596 |
| 157 | 11 | ESI+: 568 |
| 158 | 11 | ESI+: 596 |
| 159 | 11 | ESI+: 590 |
| 160 | 11 | ESI+: 596 |
| 161 | 11 | ESI+: 625 |
| 162 | 11 | ESI+: 640 |
| 163 | 11 | ESI+: 553 |
| 164 | 11 | ESI+: 638 |
| 165 | 11 | ESI+: 663 |
| 166 | 11 | ESI+: 760 |
| 167 | 11 | ESI+: 535 |

TABLE 54

| PEx | PSyn | DAT |
|---|---|---|
| 168 | 11 | ESI+: 682 |
| 169 | 11 | ESI+: 769 |
| 170 | 11 | ESI+: 626 |
| 171 | 11 | ESI+: 637 |
| 172 | 11 | ESI+: 638 |
| 173 | 11 | ESI+: 624 |
| 174 | 11 | ESI+: 740 |
| 175 | 11 | ESI+: 700 |
| 176 | 11 | ESI+: 604 |
| 177 | 11 | ESI+: 651 |
| 178 | 11 | ESI+: 625 |
| 179 | 11 | ESI+: 596 |
| 180 | 11 | ESI+: 627 |
| 181 | 11 | ESI+: 610 |
| 182 | 11 | ESI+: 609 |
| 183 | 11 | ESI+: 584 |
| 184 | 11 | ESI+: 655 |
| 185 | 11 | ESI+: 605 |
| 186 | 11 | ESI+: 628 |
| 187 | 11 | APCI/ESI+: 617 |
| 188 | 11 | ESI+: 606 |
| 189 | 11 | ESI+: 626 |
| 190 | 11 | ESI+: 636 |
| 191 | 11 | ESI+: 652, 654 |
| 192 | 11 | ESI+: 645 |
| 193 | 11 | ESI+: 576 |
| 194 | 11 | ESI+: 567 |
| 195 | 11 | ESI+: 563 |
| 196 | 11 | APCI/ESI+: 614 |
| 197 | 11 | ESI+: 614 |
| 198 | 11 | ESI+: 550 |
| 199 | 11 | ESI+: 560 |
| 200 | 11 | ESI+: 620 |
| 201 | 11 | ESI+: 625 |
| 202 | 11 | ESI+: 618 |

TABLE 55

| PEx | PSyn | DAT |
|---|---|---|
| 203 | 11 | ESI+: 618 |
| 204 | 11 | ESI+: 636 |
| 205 | 11 | ESI+: 588 |
| 206 | 11 | ESI+: 654 |
| 207 | 11 | ESI+: 627 |
| 208 | 11 | ESI+: 598 |
| 209 | 11 | ESI+: 650 |
| 210 | 11 | ESI+: 624 |
| 211 | 11 | ESI+: 634 |
| 212 | 11 | ESI+: 624 |
| 213 | 11 | ESI+: 614 |
| 214 | 11 | ESI+: 652 |
| 215 | 11 | ESI+: 616 |
| 216 | 11 | ESI+: 644 |
| 217 | 11 | ESI+: 606 |
| 218 | 11 | ESI+: 636 |

TABLE 55-continued

| PEx | PSyn | DAT |
|---|---|---|
| 219 | 11 | ESI+: 586 |
| 220 | 11 | ESI+: 642 |
| 221 | 11 | APCI/ESI+: 590 |
| 222 | 11 | ESI+: 678 |
| 223 | 11 | ESI+: 639 |
| 224 | 11 | ESI+: 630 |
| 225 | 11 | ESI+: 615 |
| 226 | 11 | ESI+: 645 |
| 227 | 12 | CI+: 203, 205 |
| 228 | 12 | CI+: 224, 226 (M+) |
| 229 | 13 | ESI+: 426 |
| 230 | 13 | ESI+: 440 |
| 231 | 13 | ESI+: 418 |
| 232 | 13 | ESI+: 440 |
| 233 | 13 | APCI/ESI+: 470 |
| 234 | 13 | ESI+: 436 |
| 235 | 13 | ESI+: 440 |
| 236 | 13 | ESI+: 418 |
| 237 | 13 | ESI+: 418 |

TABLE 56

| PEx | PSyn | DAT |
|---|---|---|
| 238 | 13 | ESI+: 414 |
| 239 | 13 | ESI+: 434 |
| 240 | 13 | ESI+: 422 |
| 241 | 13 | ESI+: 452 |
| 242 | 13 | ESI+: 436 |
| 243 | 14 | ESI+: 262 |
| 244 | 14 | ESI+: 276 |
| 245 | 14 | ESI+: 254 |
| 246 | 14 | ESI+: 306 |
| 247 | 14 | ESI+: 272 |
| 248 | 14 | ESI+: 254 |
| 249 | 14 | ESI+: 254 |
| 250 | 14 | ESI+: 250 |
| 251 | 14 | ESI+: 286 |
| 252 | 14 | ESI+: 270 |
| 253 | 14 | ESI+: 258 |
| 254 | 14 | ESI+: 288 |
| 255 | 14 | ESI+: 268 |
| 256 | 14 | ESI+: 294 [M + Na]+ |
| 257 | 17 | ESI+: 637 [M + Na]+ |
| 258 | 15 | ESI−: 530 |
| 259 | 15 | ESI+: 556 [M + Na]+ |
| 260 | 15 | ESI+: 492 |
| 261 | 15 | ESI+: 471 |
| 262 | 15 | ESI+: 554 [M + Na]+ |
| 263 | 15 | ESI+: 528 [M + Na]+ |
| 264 | 15 | ESI+: 564 [M + Na]+ |
| 265 | 15 | ESI−: 524 |
| 266 | 15 | ESI+: 566 [M + Na]+ |
| 267 | 15 | ESI+: 546 [M + Na]+ |
| 268 | 15 | ESI+: 520 [M + Na]+ |
| 269 | 15 | ESI+: 550 [M + Na]+ |
| 270 | 15 | ESI+: 516 [M + Na]+ |
| 271 | 15 | ESI+: 494 |
| 272 | 16 | ESI+: 331 |

TABLE 57

| PEx | PSyn | DAT |
|---|---|---|
| 273 | 16 | ESI+: 331 |
| 274 | 16 | ESI+: 303 |
| 275 | 16 | ESI+: 325 |
| 276 | 16 | ESI+: 331 |
| 277 | 16 | ESI+: 359 |
| 278 | 16 | ESI+: 375 |
| 279 | 16 | ESI+: 288 |
| 280 | 16 | ESI+: 373 |
| 281 | 16 | ESI+: 442 |

TABLE 57-continued

| PEx | PSyn | DAT |
|---|---|---|
| 282 | 16 | ESI+: 269 |
| 283 | 16 | ESI+: 584 |
| 284 | 16 | ESI+: 359 |
| 285 | 16 | ESI+: 554 |
| 286 | 16 | ESI+: 339 |
| 287 | 16 | ESI+: 385 |
| 288 | 16 | ESI+: 359 |
| 289 | 16 | ESI+: 361 |
| 290 | 16 | ESI+: 319 |
| 291 | 16 | ESI+: 389 |
| 292 | 16 | ESI+: 341 |
| 293 | 16 | ESI+: 311 |
| 294 | 16 | ESI+: 302 |
| 295 | 16 | ESI+: 298 |
| 296 | 16 | ESI+: 333 |
| 297 | 16 | APCI/ESI+: 295 |
| 298 | 16 | ESI+: 355 |
| 299 | 16 | ESI+: 359 |
| 300 | 16 | ESI+: 337 |
| 301 | 16 | ESI+: 337 |
| 302 | 16 | ESI+: 333 |
| 303 | 16 | ESI+: 369 |
| 304 | 16 | ESI+: 353 |
| 305 | 16 | ESI+: 341 |
| 306 | 16 | ESI+: 371 |
| 307 | 16 | ESI+: 351 |

TABLE 58

| PEx | PSyn | DAT |
|---|---|---|
| 308 | 16 | ESI+: 325 |
| 309 | 16 | ESI+: 355 |
| 310 | 16 | ESI+: 321 |
| 311 | 16 | APCI/ESI+: 309 |
| 312 | 16 | ESI+: 321 |
| 313 | 17 | ESI+: 504 |
| 314 | 17 | ESI+: 504 |
| 315 | 17 | ESI−: 514 |
| 316 | 15 | ESI+: 498 |
| 317 | 17 | ESI+: 504 |
| 318 | 17 | ESI+: 532 |
| 319 | 17 | ESI+: 570 [M + Na]+ |
| 320 | 17 | ESI−: 544 |
| 321 | 17 | ESI+: 442 |
| 322 | 17 | ESI+: 554 [M + Na]+ |
| 323 | 17 | ESI−: 510 |
| 324 | 17 | ESI−: 557 |
| 325 | 17 | ESI+: 584 [M + Na]+ |
| 326 | 17 | APCI/ESI+: 484 |
| 327 | 17 | ESI+: 475 |
| 328 | 17 | ESI+: 528 [M + Na]+ |
| 329 | 17 | ESI+: 550 [M + Na]+ |
| 330 | 17 | ESI+: 532 [M + Na]+ |
| 331 | 17 | ESI+: 532 [M + Na]+ |
| 332 | 17 | ESI+: 536 [M + Na]+ |
| 333 | 18 | ESI+: 276 |
| 334 | 18 | ESI+: 276 |
| 335 | 21 | ESI+: 431 |
| 336 | 22 | ESI+: 331 |
| 337 | 22 | ESI+: 536 |
| 338 | 26 | ESI+: 311 |
| 339 | 26 | ESI+: 374 |
| 340 | 26 | ESI+: 318 |
| 341 | 28 | ESI+: 388 |
| 342 | 30 | ESI+: 578 |

TABLE 59

| PEx | PSyn | DAT |
|---|---|---|
| 343 | 31 | ESI+: 287 |
| 344 | 31 | ESI+: 305 |
| 345 | 31 | ESI+: 426 [M + Na]+ |
| 346 | 31 | ESI+: 427 |
| 347 | 32 | $^1$H-NMR (400 MHz, CDCl$_3$) δ ppm 1.43 (9H, s) 2.33 (3H, s) 3.22 (1H, dd, J = 14.4, 6.4 Hz) 3.30 (1H, dd, J = 14.4, 5.6 Hz) 4.28 (1H, t, J = 6.2 Hz) 7.02-7.07 (2H, m) 7.11 (1H, d, J = 7.6 Hz) 7.20-7.27 (1H, m) |
| 348 | 32 | $^1$H-NMR (400 MHz, DMSO-d6) δ ppm 1.34 (9H, s) 2.19 (6H, s) 2.86-3.03 (2H, m) 4.00-4.06 (1H, m) 6.95 (1H, dd, J = 7.4, 1.6 Hz) 6.98-7.02 (1H, m) 7.09 (1H, d, J = 7.4 Hz) |
| 349 | 32 | ESI+: 242 |
| 350 | 35 | ESI+: 294 |
| 351 | 35 | ESI+: 332 |
| 352 | 37 | ESI+: 342 |
| 353 | 37 | ESI+: 386, 388 |
| 354 | 37 | ESI+: 322 |
| 355 | 38 | ESI+: 439 |
| 356 | 38 | ESI+: 442 |
| 357 | 38 | ESI+: 441 |
| 358 | 38 | APCI/ESI+: 450 |
| 359 | 38 | ESI+: 485, 487 |
| 360 | 38 | ESI+: 477 |
| 361 | 38 | APCI/ESI+: 447 |
| 362 | 38 | ESI+: 421 |
| 363 | 38 | APCI/ESI+: 460 |
| 364 | 38 | ESI+: 447 |
| 365 | 39 | ESI+: 282 |
| 366 | 39 | APCI/ESI+: 291 |
| 367 | 39 | ESI+: 326, 328 |
| 368 | 39 | APCI/ESI+: 288 |
| 369 | 39 | ESI+: 262 |
| 370 | 39 | ESI+: 301 |
| 371 | 39 | ESI+: 288 |
| 372 | 39 | ESI+: 326 |

TABLE 60

| PEx | PSyn | DAT |
|---|---|---|
| 373 | 41 | ESI+: 340 |
| 374 | 41 | ESI+: 400 [M + Na]+ |
| 375 | 41 | APCI/ESI+: 348 |
| 376 | 41 | APCI/ESI+: 361 |
| 377 | 41 | ESI+: 348 |
| 378 | 43 | ESI+: 390 |
| 379 | 46 | EI: 214, 216 |
| 380 | 47 | ESI+: 659 |
| 381 | 47 | ESI+: 238 |
| 382 | 37 | ESI+: 326 |
| 383 | 38 | ESI+: 425 |
| 384 | 39 | ESI+: 266 |
| 385 | 11 | ESI+: 593 |
| 386 | 11 | ESI+: 534 |
| 387 | 11 | ESI+: 664 |
| 388 | 11 | ESI+: 603 |
| 389 | 11 | APCI/ESI+: 672 |
| 390 | 11 | ESI+: 618 |
| 391 | 11 | ESI+: 649 |
| 392 | 11 | ESI+: 656 |
| 393 | 11 | ESI+: 664 |
| 394 | 11 | ESI+: 644 |
| 395 | 11 | ESI+: 656 |
| 396 | 6 | ESI+: 348 [M + Na]+ |
| 397 | 47 | ESI+: 226 |
| 398 | 15 | ESI+: 504 [M + Na]+ |
| 399 | 15 | ESI+: 542 [M + Na]+ |
| 400 | 8 | ESI+: 530 [M + Na]+ |
| 401 | 8 | ESI+: 622, 624 [M + Na]+ |
| 402 | 8 | ESI+: 546 |
| 403 | 9 | ESI+: 494 |
| 404 | 9 | ESI+: 548 |
| 405 | 9 | ESI+: 532 |

TABLE 60-continued

| PEx | PSyn | DAT |
| --- | --- | --- |
| 406 | 16 | ESI+: 309 |
| 407 | 16 | ESI+: 363 |

TABLE 61

| PEx | PSyn | DAT |
| --- | --- | --- |
| 408 | 13 | ESI+: 482, 484 |
| 409 | 13 | ESI+: 428 |
| 410 | 14 | ESI+: 318, 320 |
| 411 | 14 | ESI+: 264 |
| 412 | 17 | ESI+: 596, 598 [M + Na]+ |
| 413 | 19 | ESI+: 562 |
| 414 | 10 | ESI+: 347 |
| 415 | 7 | APCI/ESI+: 482 |
| 416 | 416 | ESI+: 300 |
| 417 | 417 | ESI+: 558 [M + Na]+ |
| 418 | 37 | ESI+: 360 |
| 419 | 38 | ESI+: 459 |
| 420 | 9 | ESI+: 522 |
| 421 | 16 | ESI+: 337 |

TABLE 62

TABLE 62-continued

TABLE 62-continued
| Ex | Str |
|---|---|
| 9 | 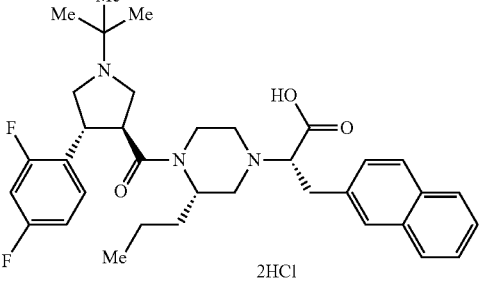 2HCl |
| 10 | 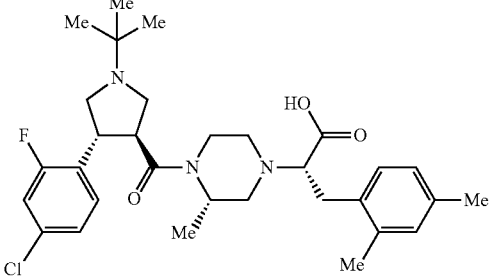 |
TABLE 63
| Ex | Str |
|---|---|
| 11 |  2HCl |
| 12 | 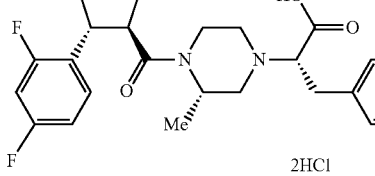 2HCl |
TABLE 63-continued
| Ex | Str |
|---|---|
| 13 | 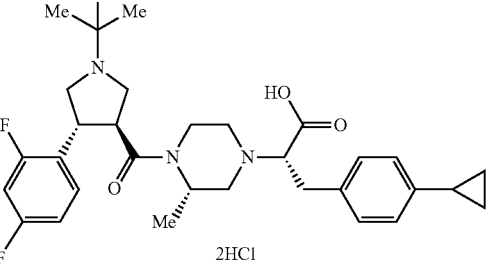 2HCl |
| 14 | 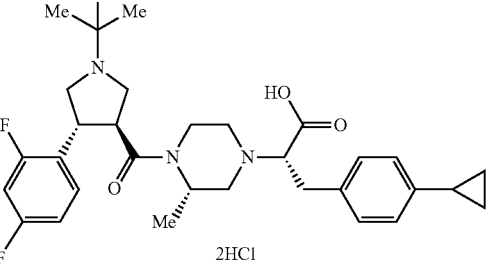 2HCl |
| 15 | 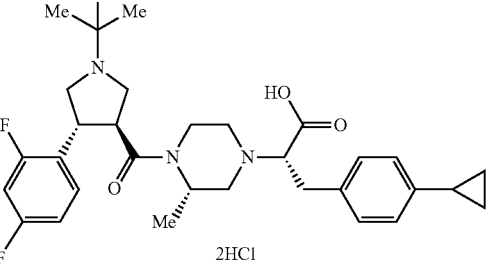 2HCl $ |
| 16 | 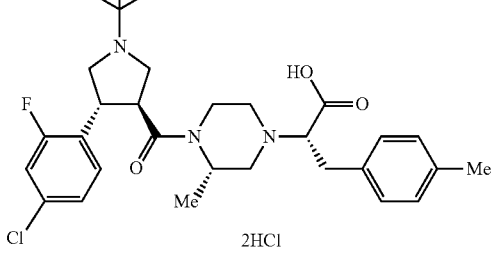 2HCl $ |
| 17 | 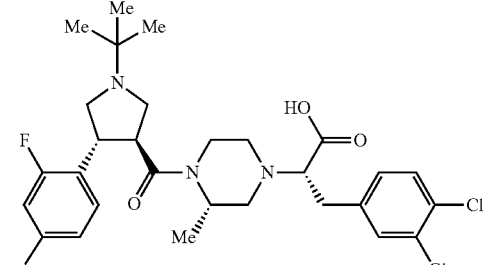 2HCl |

TABLE 63-continued
| Ex | Str |
|---|---|
| 18 | 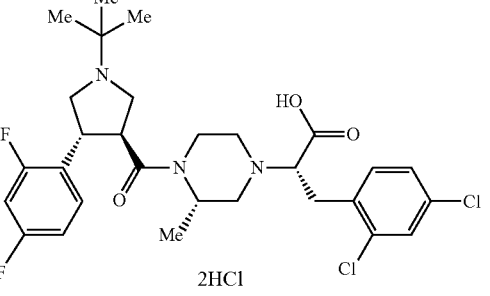 2HCl |
| 19 | 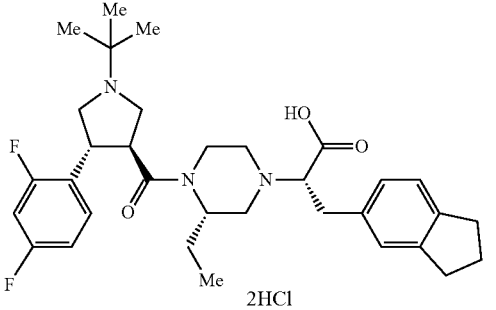 [SMILES: CC[C@H]1CN([C@@H](Cc2ccc3c(c2)CCC3)C(=O)O)CCN1C(=O)[C@@H]1CN(C(C)(C)C)C[C@H]1c1ccc(F)cc1F] 2HCl |
| 20 | 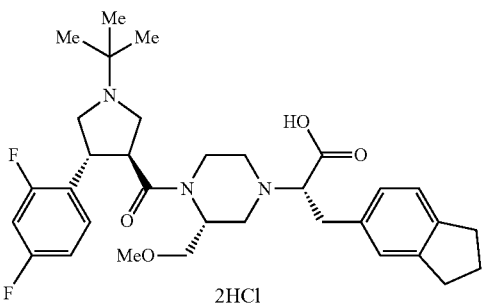 [SMILES: COC[C@H]1CN([C@@H](Cc2ccc3c(c2)CCC3)C(=O)O)CCN1C(=O)[C@@H]1CN(C(C)(C)C)C[C@H]1c1ccc(F)cc1F] 2HCl |
TABLE 64
| Ex | Str |
|---|---|
| 21 | 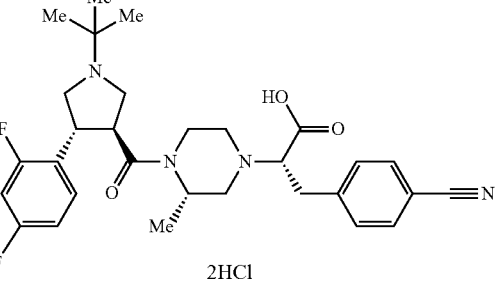 2HCl |
| 22 | 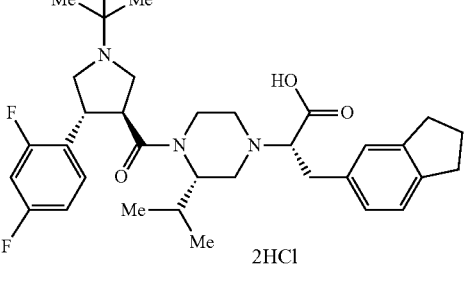 2HCl |
| 23 | 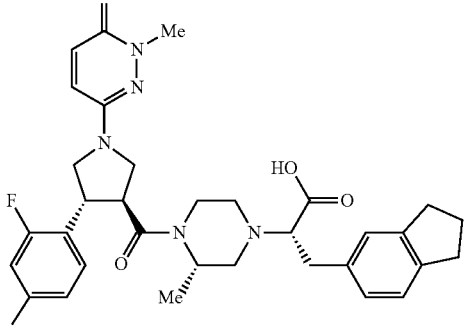 HCl |
| 24 | 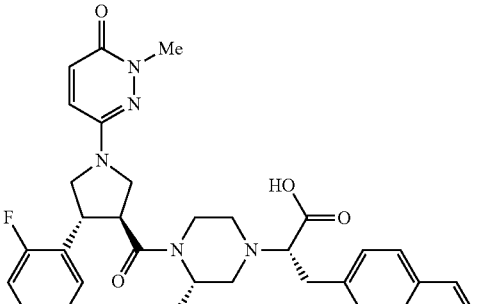 2HCl |
| 25 | 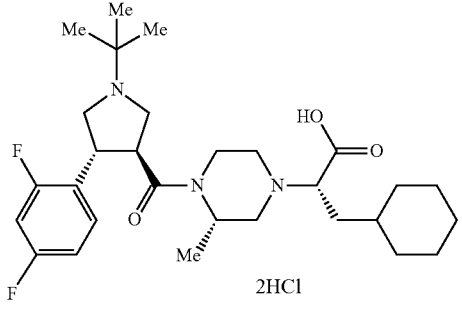 [SMILES: C[C@H]1CN([C@@H](CC2CCCCC2)C(=O)O)CCN1C(=O)[C@@H]1CN(C(C)(C)C)C[C@H]1c1ccc(F)cc1F ; "2HCl"] 2HCl |

TABLE 64-continued
| Ex | Str |
|---|---|
| 26 | 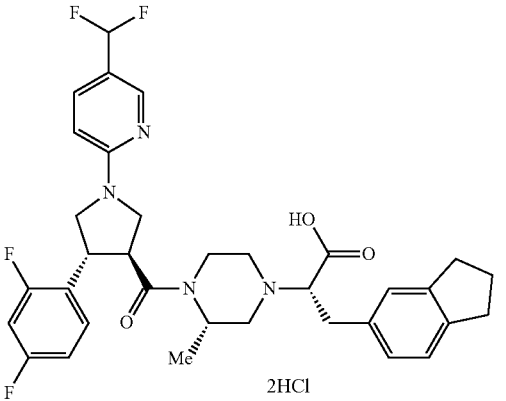 [SMILES: C[C@H]1CN([C@@H](Cc2ccc3c(c2)CCC3)C(=O)O)CCN1C(=O)[C@@H]1CN(c2ccc(C(F)F)cn2)C[C@H]1c1ccc(F)cc1F] 2HCl |
| 27 | 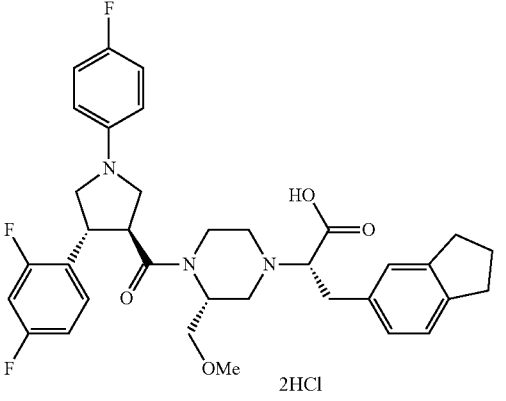 [SMILES: COC[C@H]1CN([C@@H](Cc2ccc3c(c2)CCC3)C(=O)O)CCN1C(=O)[C@@H]1CN(c2ccc(F)cc2)C[C@H]1c1ccc(F)cc1F] 2HCl |
| 28 | 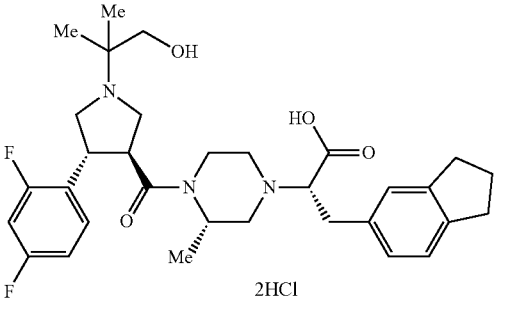 [SMILES: C[C@H]1CN([C@@H](Cc2ccc3c(c2)CCC3)C(=O)O)CCN1C(=O)[C@@H]1CN(C(C)(C)CO)C[C@H]1c1ccc(F)cc1F] 2HCl |
| 29 | 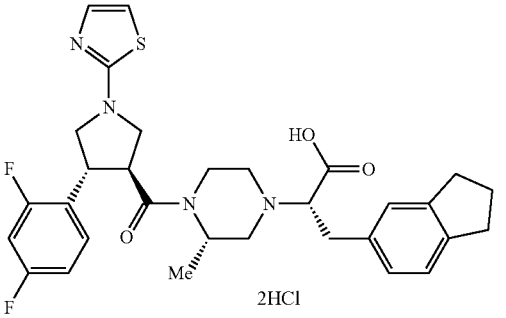 [SMILES: C[C@H]1CN([C@@H](Cc2ccc3c(c2)CCC3)C(=O)O)CCN1C(=O)[C@@H]1CN(c2nccs2)C[C@H]1c1ccc(F)cc1F] 2HCl |
TABLE 64-continued
| Ex | Str |
|---|---|
| 30 | 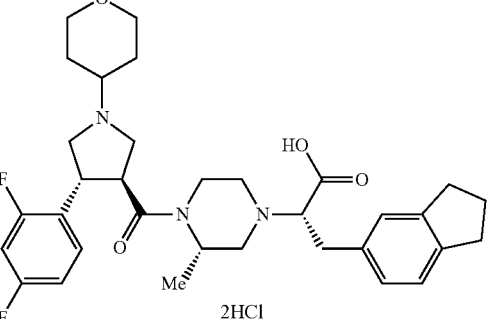 2HCl |
TABLE 65
| Ex | Str |
|---|---|
| 31 | 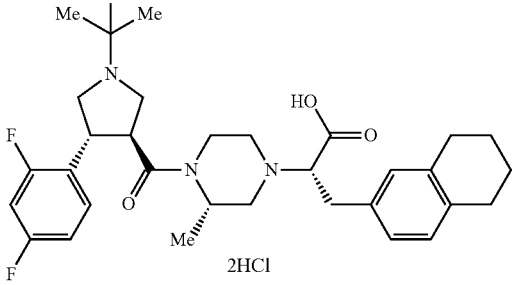 2HCl |
| 32 | 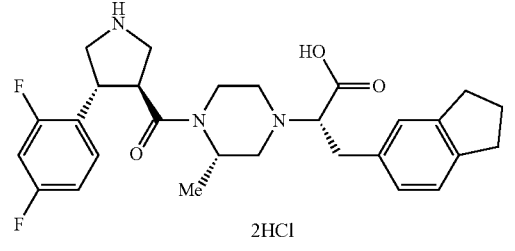 [SMILES: C[C@H]1CN([C@@H](Cc2ccc3c(c2)CCC3)C(=O)O)CCN1C(=O)[C@@H]1CNC[C@H]1c1ccc(F)cc1F] 2HCl |
| 33 | 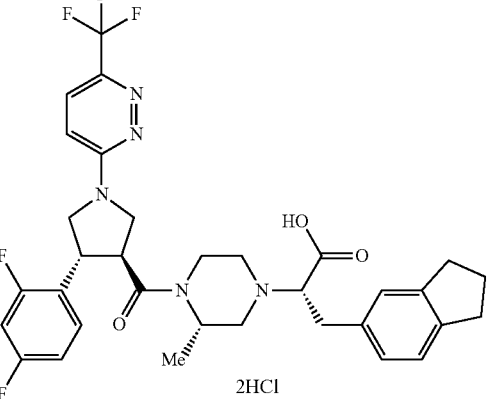 2HCl |

TABLE 65-continued

| Ex | Str |
|---|---|
| 34 | (structure) 2HCl |
| 35 | (structure) HCl |
| 36 | (structure) 2HCl |
| 37 | (structure) 2HCl |
| 38 | (structure) 2HCl |
| 39 | (structure) 2HCl |
| 40 | (structure) ** 2HCl |

TABLE 66

| Ex | Str |
|---|---|
| 41 | (structure) ** 2HCl |
| 42 | (structure) ** 2HCl |

TABLE 66-continued

| Ex | Str |
|---|---|
| 43 | (structure with 2,4-difluorophenyl pyrrolidine, piperazine, 3-methylphenyl propanoic acid) 2HCl |
| 44 | (structure with 2,4-difluorophenyl pyrrolidine, piperazine, 4-trifluoromethoxyphenyl propanoic acid) 2HCl |
| 45 | ** (structure with 4-methoxyphenyl pyrrolidine, piperazine, indanyl propanoic acid) 2HCl |
| 46 | (structure with 2,3,4-trifluorophenyl pyrrolidine, piperazine, indanyl propanoic acid) 2HCl |
| 47 | ** (structure with 2-fluoro-4-cyanophenyl pyrrolidine, piperazine, indanyl propanoic acid) 2HCl |
| 48 | (structure with 2,4-difluorophenyl pyrrolidine, piperazine, phenyl propanoic acid) HBr HCl |
| 49 | (structure with 2-fluoro-4-chlorophenyl pyrrolidine, piperazine, indanyl propanoic acid) 2HCl |
| 50 | (structure with N-acetyl pyrrolidine, 2,4-difluorophenyl, piperazine with ethyl, naphthyl propanoic acid) HCl |

TABLE 67

| Ex | Str |
|---|---|
| 51 | (structure with 4-bromophenyl pyrrolidine, piperazine, indanyl propanoic acid) 2HCl |

TABLE 67-continued
| Ex | Str |
|---|---|
| 52 | 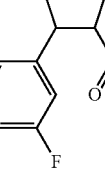 ** 2HCl |
| 53 | 2HCl |
| 54 | 3HCl |
| 55 | ** 2HCl |
| 56 | 2HCl |
| 57 | 2HCl |
| 58 | 2HCl |
| 59 | 2HCl |
| 60 | 2HCl |

TABLE 68
| Ex | Str |
|---|---|
| 61 | |
| 62 | |
| 63 | |
| 64 | |
| 65 | |
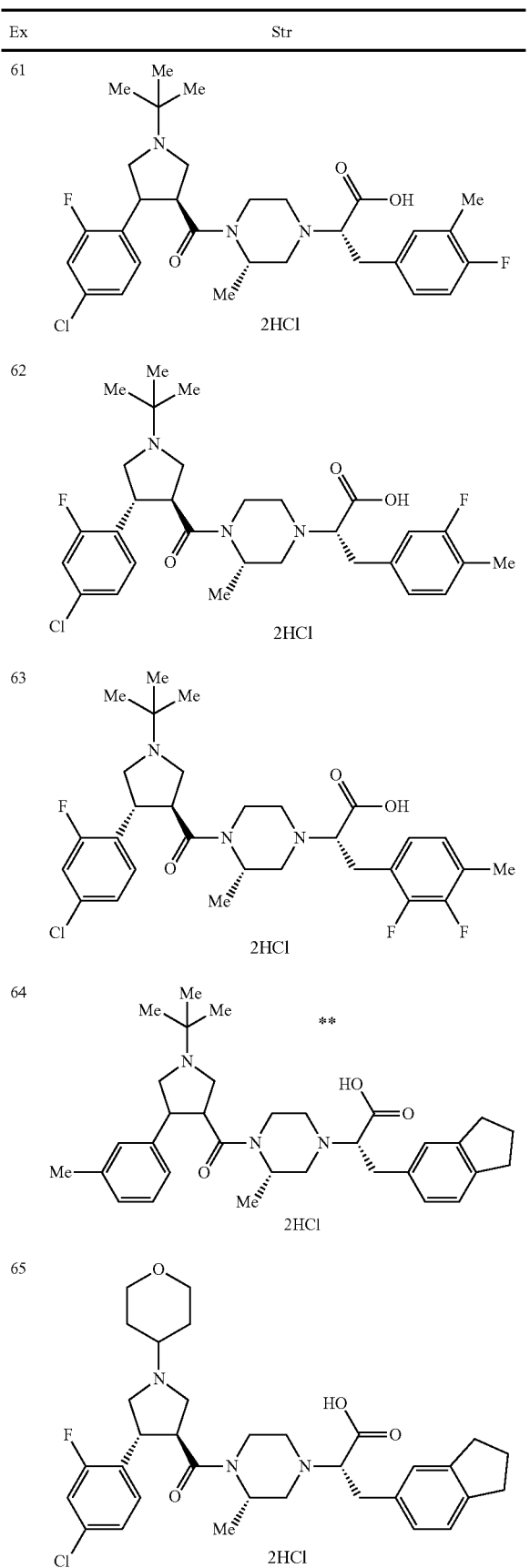
TABLE 68-continued
| Ex | Str |
|---|---|
| 66 | |
| 67 | |
| 68 | |
| 69 | |
| 70 | |
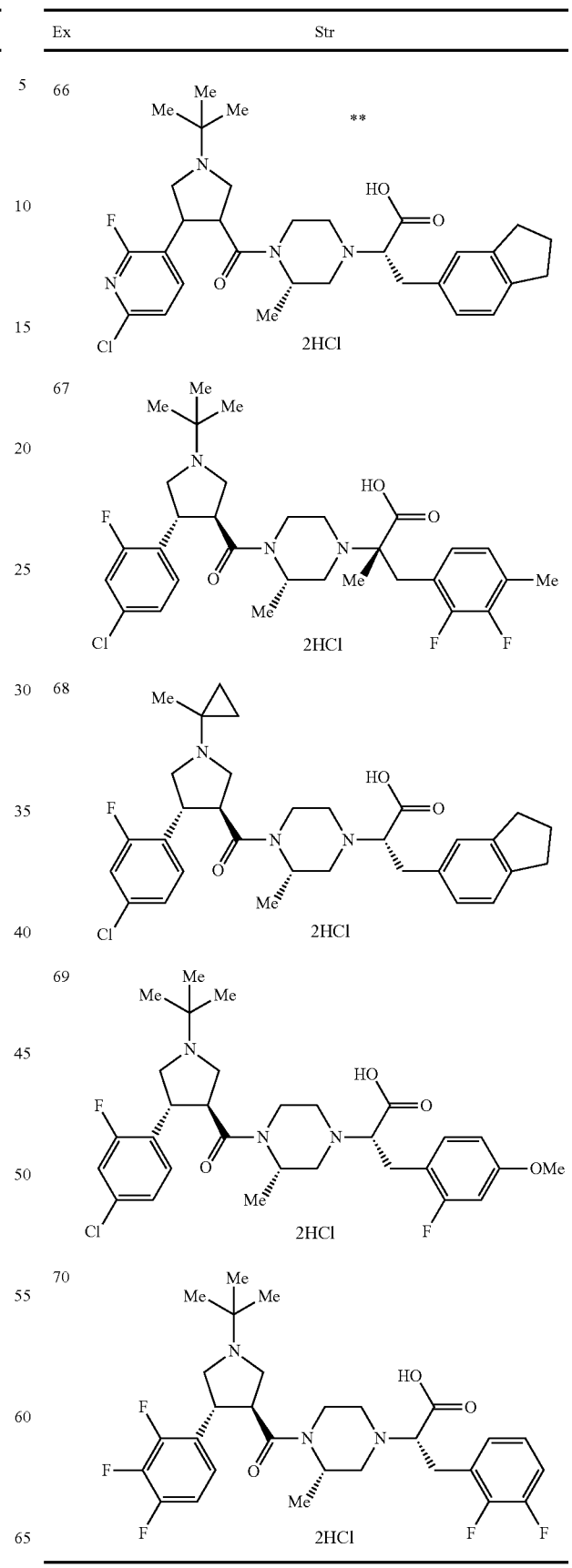

TABLE 69
| Ex | Str |
|---|---|
| 71 | 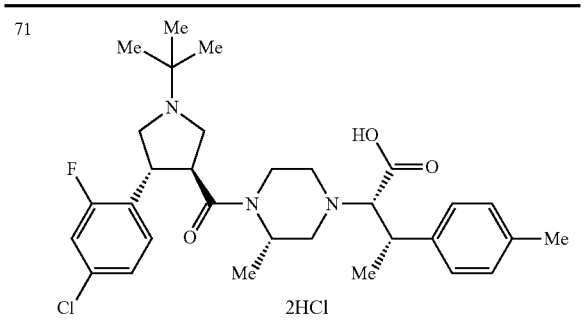 |
| 72 | 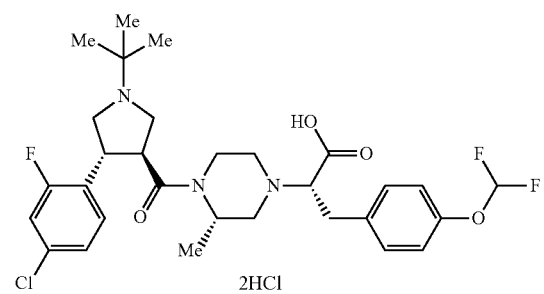 [SMILES: C[C@H]1CN([C@@H](Cc2ccc(OC(F)F)cc2)C(=O)O)CCN1C(=O)[C@@H]1CN(C(C)(C)C)C[C@H]1c1ccc(Cl)cc1F] |
| 73 | 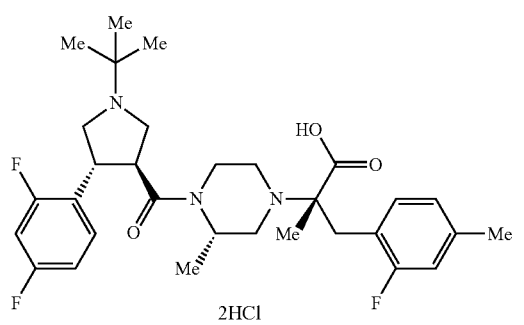 [SMILES: Cc1ccc(C[C@@](C)(C(=O)O)N2CCN(C(=O)[C@@H]3CN(C(C)(C)C)C[C@H]3c3ccc(F)cc3F)[C@@H](C)C2)c(F)c1] |
| 74 | 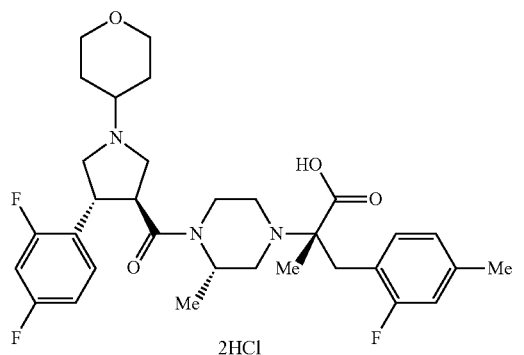 [SMILES: Cc1ccc(C[C@@](C)(C(=O)O)N2CCN(C(=O)[C@@H]3CN(C4CCOCC4)C[C@H]3c3ccc(F)cc3F)[C@@H](C)C2)c(F)c1] |
TABLE 69-continued
| Ex | Str |
|---|---|
| 75 | 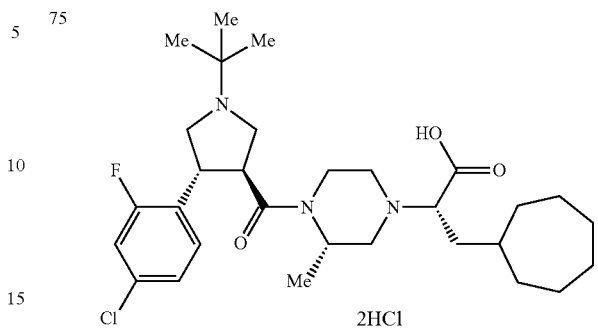 |
| 76 | 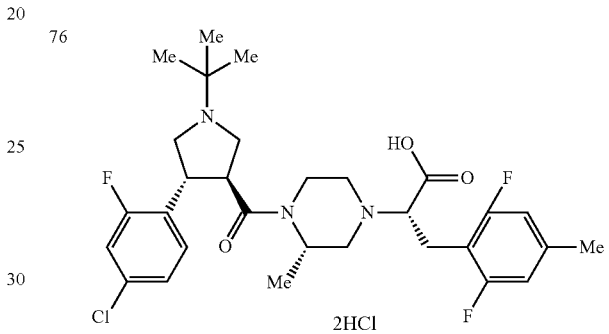 |
| 77 | 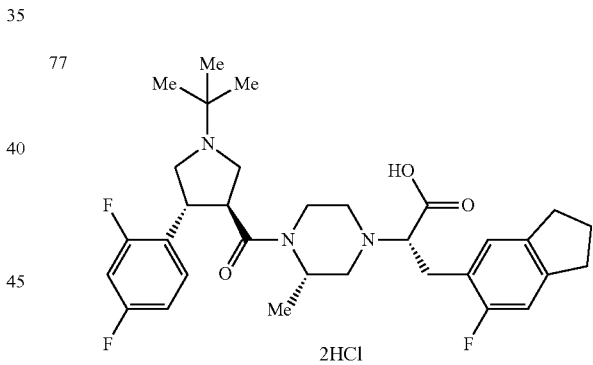 |
| 78 | 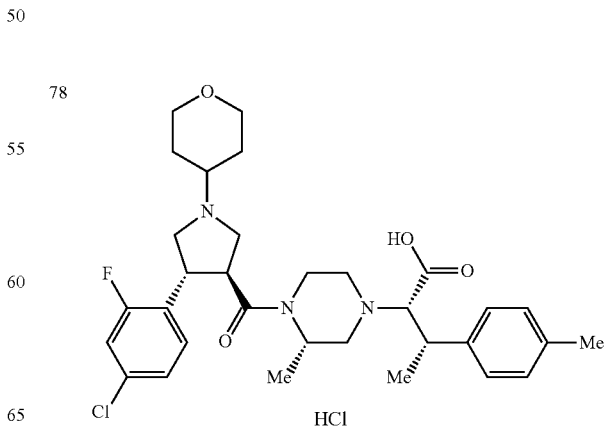 |

TABLE 69-continued
| Ex | Str |
|---|---|
| 79 | 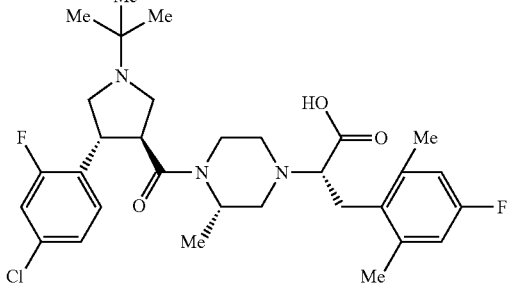 |
| 80 | 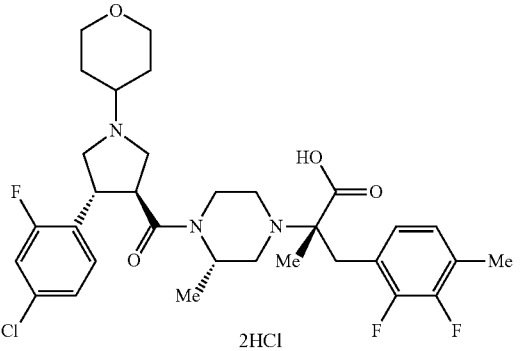 [SMILES: Cc1ccc(C[C@@](C)(C(=O)O)N2CCN(C(=O)[C@@H]3CN(C4CCOCC4)C[C@H]3c3ccc(Cl)cc3F)[C@@H](C)C2)c(F)c1F]<br>2HCl |
TABLE 70
| Ex | Str |
|---|---|
| 81 | 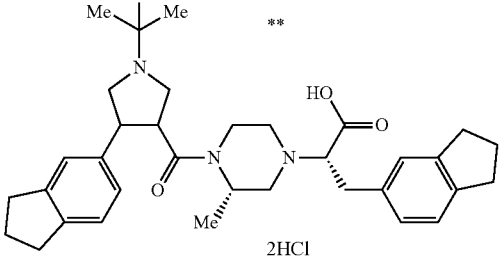<br>2HCl |
| 82 | 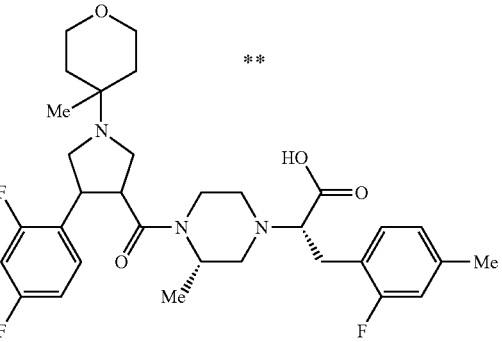<br>2HCl |
TABLE 70-continued
| Ex | Str |
|---|---|
| 83 | 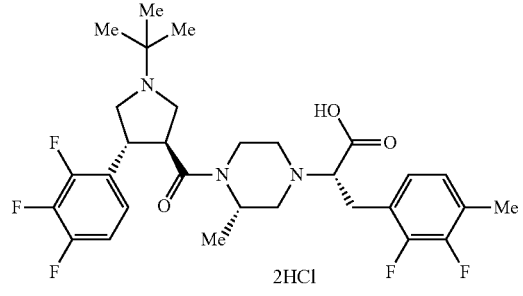 [SMILES: Cc1ccc(C[C@@H](C(=O)O)N2CCN(C(=O)[C@@H]3CN(C(C)(C)C)C[C@H]3c3ccc(F)c(F)c3F)[C@@H](C)C2)c(F)c1F]<br>2HCl |
| 84 | 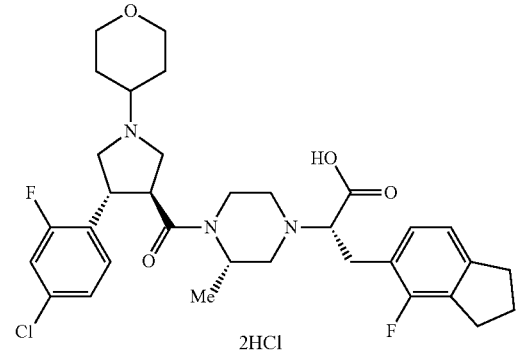 [SMILES: C[C@H]1CN([C@@H](Cc2ccc3c(c2F)CCC3)C(=O)O)CCN1C(=O)[C@@H]1CN(C2CCOCC2)C[C@H]1c1ccc(Cl)cc1F ; "2HCl"] |
| 85 | 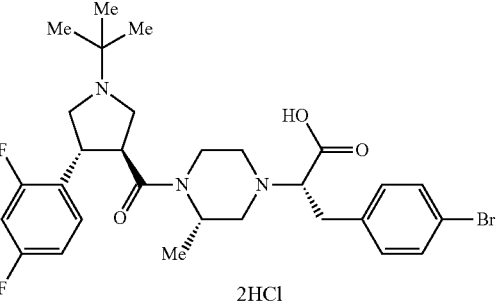 [SMILES: C[C@H]1CN([C@@H](Cc2ccc(Br)cc2)C(=O)O)CCN1C(=O)[C@@H]1CN(C(C)(C)C)C[C@H]1c1ccc(F)cc1F]<br>2HCl |
| 86 | 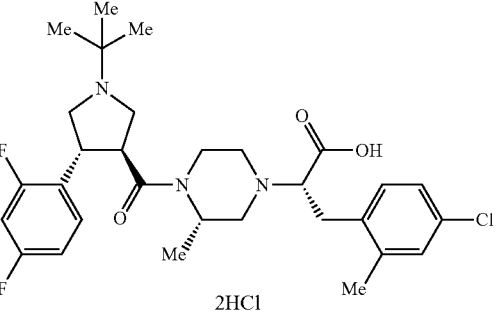 [SMILES: Cc1cc(Cl)ccc1C[C@@H](C(=O)O)N1CCN(C(=O)[C@@H]2CN(C(C)(C)C)C[C@H]2c2ccc(F)cc2F)[C@@H](C)C1]<br>2HCl |

TABLE 70-continued
| Ex | Str |
|---|---|
| 87 | 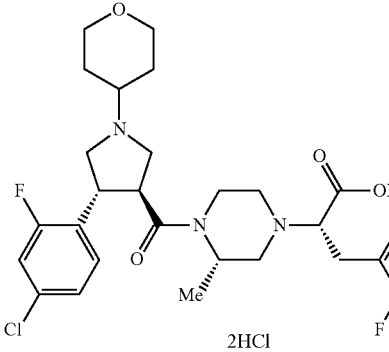 2HCl |
| 88 | 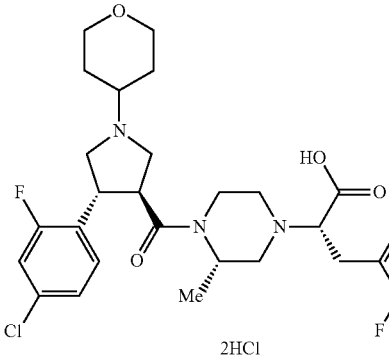 2HCl |
| 89 | 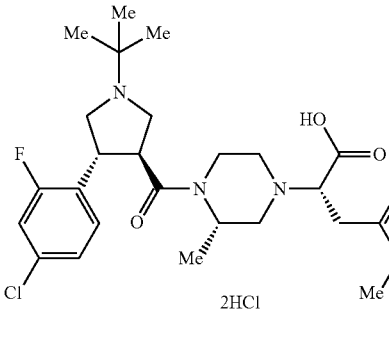 2HCl |
| 90 | 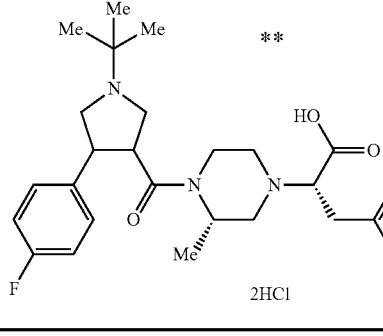 ** 2HCl |
TABLE 71
| Ex | Str |
|---|---|
| 91 | 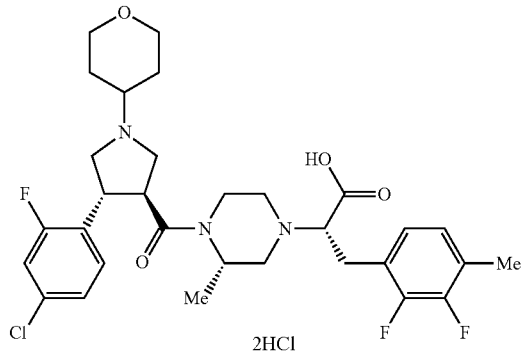 [SMILES: Cc1ccc(C[C@@H](C(=O)O)N2CCN(C(=O)[C@@H]3CN(C4CCOCC4)C[C@H]3c3ccc(Cl)cc3F)[C@@H](C)C2)c(F)c1F ; "2HCl"] 2HCl |
| 92 | 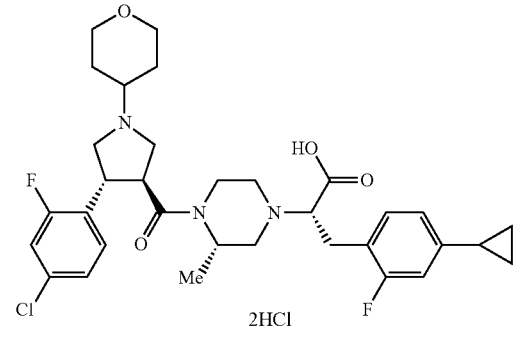 [SMILES: C[C@H]1CN([C@@H](Cc2ccc(C3CC3)cc2F)C(=O)O)CCN1C(=O)[C@@H]1CN(C2CCOCC2)C[C@H]1c1ccc(Cl)cc1F ; "2HCl"] 2HCl |
| 93 | 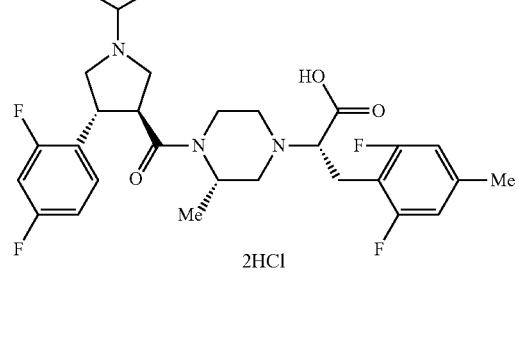 2HCl |
| 94 | 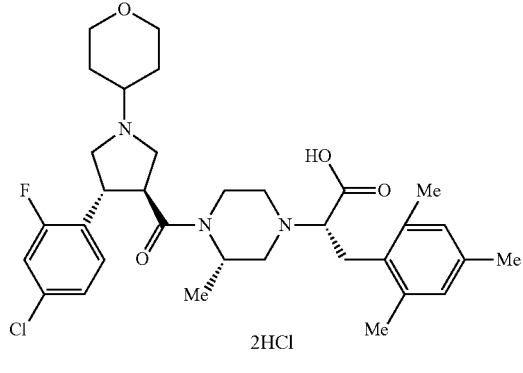 [SMILES: Cc1cc(C)c(C[C@@H](C(=O)O)N2CCN(C(=O)[C@@H]3CN(C4CCOCC4)C[C@H]3c3ccc(Cl)cc3F)[C@@H](C)C2)c(C)c1 ; "2HCl"] 2HCl |

TABLE 71-continued
| Ex | Str |
|---|---|
| 95 | 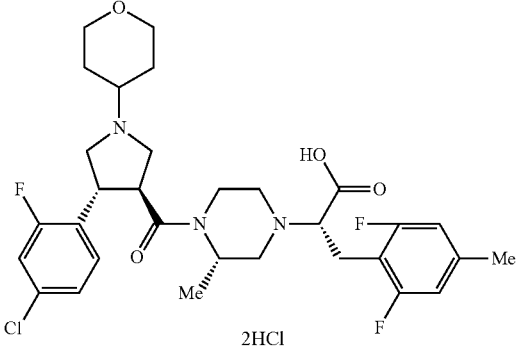 [SMILES: Cc1cc(F)c(C[C@@H](C(=O)O)N2CCN(C(=O)[C@@H]3CN(C4CCOCC4)C[C@H]3c3ccc(Cl)cc3F)[C@@H](C)C2)c(F)c1 ; "2HCl"] 2HCl |
| 96 | 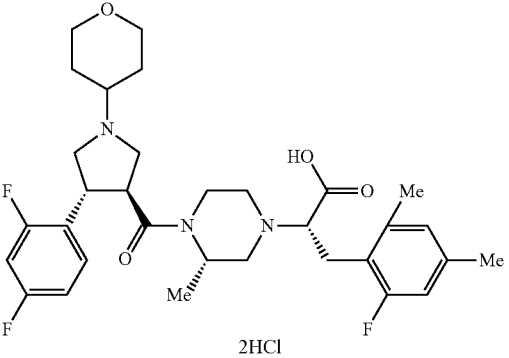 [SMILES: Cc1cc(C)c(C[C@@H](C(=O)O)N2CCN(C(=O)[C@@H]3CN(C4CCOCC4)C[C@H]3c3ccc(F)cc3F)[C@@H](C)C2)c(F)c1 ; "2HCl"] 2HCl |
| 97 | 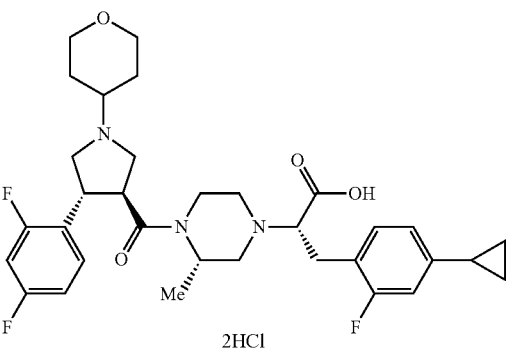 [SMILES: C[C@H]1CN([C@@H](Cc2ccc(C3CC3)cc2F)C(=O)O)CCN1C(=O)[C@@H]1CN(C2CCOCC2)C[C@H]1c1ccc(F)cc1F ; "2HCl"] 2HCl |
TABLE 71-continued
| Ex | Str |
|---|---|
| 98 | 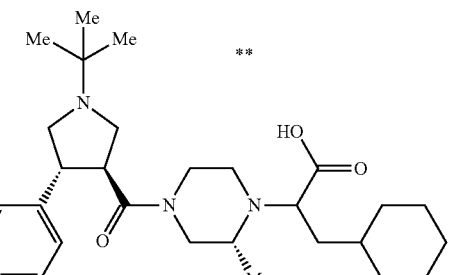 ** |
| 99 | 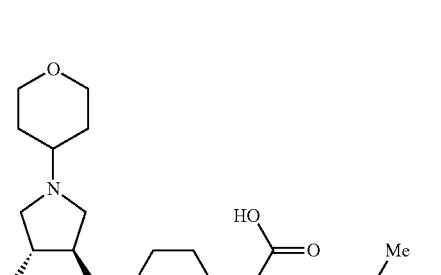 2HCl |
| 100 | 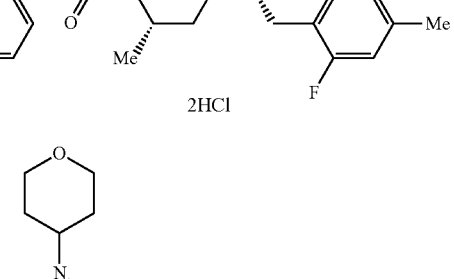 2HCl |
TABLE 72
| Ex | Syn | DAT |
|---|---|---|
| 1 | 1 | ESI+: 590<br>$^1$H-NMR (500 MHz, pyridine-d5, 90° C.) δ ppm 1.10 (3H, d, J = 6.7 Hz) 1.49-1.63 (2H, m) 1.66-1.75 (2H, m) 2.18 (3H, s) 2.31-2.40 (1H, m) 2.54-2.64 (1H, m) 2.66-2.73 (1H, m) 2.87-3.14 (6H, m) 3.17-3.29 (3H, m) 3.31-3.40 (2H, m) 3.42-3.52 (1H, m) 3.73-3.78 (1H, m) 3.87-3.98 (2H, m) 4.21-4.29 (1H, m) 6.84-6.90 (2H, m) 7.08-7.16 (2H, m) 7.24-7.29 (1H, m) 7.49-7.58 (1H, m)<br>2θ (°) = 9.1, 12.7, 13.7, 14.1, 15.5, 15.9, 18.3, 19.5, 21.7, 28.8 |
| 2 | 2 | ESI+: 605<br>$^1$H-NMR (500 MHz, pyridine-d5, 90° C.) δ ppm 1.09 (3H, d, J = 6.7 Hz) 1.50-1.63 (2H, m) 1.66-1.75 (2H, m) 2.15 (3H, s) 2.31-2.39 (1H, m) 2.35 (3H, s) 2.58-2.71 (2 H, m) 2.87-3.05 (4H, m) 3.08-3.19 (2H, m) 3.20-3.29 (3H, m) 3.30-3.39 (2H, m) 3.43-3.52 (1H, m) 3.69-3.75 (1H, m) 3.87-3.98 (2H, m) 4.22-4.30 (1H, m) 6.72-6.78 (2H, m) 7.07-7.17 (2H, m) 7.51-7.57 (1H, m)<br>2θ (°) = 8.2, 9.0, 12.6, 13.9, 15.1, 15.9, 18.9, 21.3, 22.9, 28.3 |
| 3 | 3 | ESI+: 572<br>$^1$H-NMR (500 MHz, pyridine-d5, 90° C.) δ ppm 1.08 (9H, s) 1.20 (3H, d, J = 6.7 Hz) 2.17 (3H, s) 2.40 (6H, s) 2.62-2.70 (1H, m) |

TABLE 72-continued

| Ex | Syn | DAT |
|---|---|---|
|   |   | 2.71-2.76 (1H, m) 2.82-2.88 (1H, m) 2.89 (1H, dd, J = 8.7, 6.3 Hz) 3.04-3.21 (5H, m) 3.28 (1H, t, J = 8.2 Hz) 3.37 (1H, dd, J = 14.3, 7.3 Hz) 3.46-3.54 (1H, m) 3.59 (1H, dd, J = 7.7, 6.5 Hz) 4.18-4.25 (1H, m) 6.82 (2H, s) 7.08-7.16 (2H, m) 7.53-7.58 (1H, m) 2θ (°) = 5.4, 8.5, 10.8, 12.1, 12.6, 13.8, 14.2, 15.6, 17.9, 19.6 |
| 4 | 4 | ESI+: 562 $^1$H-NMR (500 MHz, pyridine-d5, 90° C.) δ ppm 0.84-1.15 (3H, brs), 1.40 (9H, m) 2.18 (3H, s) 2.38-2.51 (1H, m) 2.53-2.68 (1H, m) 2.77-2.90 (1H, m) 2.91-3.03 (1H, m) 3.08-3.16 (1H, m) 3.16-3.24 (1H, m) 3.57-3.71 (3H, m) 3.71-3.79 (1H, m) 3.85 (1H, dd, J = 10.4, 6.4 Hz) 4.25-4.33 (1H, m) 4.34-4.46 (1H, m) 6.82-6.88 (2H, m) 7.10-7.23 (3H, m) 8.08-8.18 (1H, m) |
| 5 | 5 | ESI+: 554 $^1$H-NMR (500 MHz, pyridine-d5, 90° C.) δ ppm 1.08 (3H, brs) 1.40 (9H, s) 1.84-1.95 (2H, m) 2.38-2.56 (1H, m) 2.59-2.80 (5H, m) 2.80-2.92 (1H, m) 2.93-3.06 (2H, m) 3.20-3.26 (1H, m) 3.57-3.78 (4H, m) 3.82-3.91 (1H, m) 4.23-4.33 (1H, m) 4.34-4.45 (1H, m) 6.83-6.97 (2H, m) 7.09-7.14 (2H, m) 7.18 (1H, s) 8.09-8.26 (1H, m) |
| 6 | 6 | ESI+: 578 |

TABLE 73

| Ex | Syn | DAT |
|---|---|---|
| 7 | 7 | ESI+: 528 |
| 8 | 8 | ESI+: 542 |
| 9 | 4 | ESI+: 592 $^1$H-NMR (500 MHz, pyridine-d5, 90° C.) δ ppm 0.45-1.61 (7H, m) 1.40 (9H, s) 2.03-2.69 (2H, m) 2.71-3.12 (3H, m) 3.21 (1H, dd, J = 14.0, 8.6 Hz) 3.32-3.45 (1H, m) 3.47-3.87 (6H, m) 4.18-4.85 (3H, m) 6.86-6.92 (1H, m) 6.93-6.99 (1H, m) 7.31-7.49 (3H, m) 7.76-7.82 (4H, m) 8.01-8.35 (1H, m) |
| 10 | 1 | ESI+: 558 |
| 11 | 5 | ESI+: 544 $^1$H-NMR (500 MHz, pyridine-d5, 90° C.) δ ppm 0.93-1.17 (3H, brs) 1.41 (9H, s) 2.20 (3H, s) 2.39-2.53 (1H, m) 2.58-2.71 (1H, m) 2.80-3.04 (2H, m) 3.00 (1H, dd, J = 14.1, 7.3 Hz) 3.20 (1H, dd, J = 14.1, 7.3 Hz) 3.57-3.71 (3H, m) 3.72-3.79 (1H, m) 3.86 (1H, dd, J = 10.9, 6.4 Hz) 4.25-4.35 (1H, m) 4.35-4.45 (1H, m) 7.03-7.23 (6H, m) 8.08-8.18 (1H, m) |
| 12 | 4 | ESI+: 582 |
| 13 | 4 | ESI+: 582 |
| 14 | 4 | ESI+: 554 |
| 15 | 6 | ESI+: 582 |
| 16 | 4 | ESI+: 582 |
| 17 | 4 | ESI+: 576 |
| 18 | 4 | ESI+: 582 |
| 19 | 5 | ESI+: 568 |
| 20 | 5 | ESI+: 585 |
| 21 | 4 | ESI+: 539 |
| 22 | 5 | ESI+: 582 |
| 23 | 5 | ESI+: 606 |
| 24 | 4 | ESI+: 674 |
| 25 | 4 | ESI+: 521 |
| 26 | 5 | ESI+: 625 |
| 27 | 5 | ESI+: 622 |
| 28 | 5 | ESI+: 570 |
| 29 | 5 | ESI+: 581 |
| 30 | 5 | ESI+: 582 |

TABLE 74

| Ex | Syn | DAT |
|---|---|---|
| 31 | 5 | ESI+: 568 |
| 32 | 5 | ESI+: 498 |
| 33 | 5 | ESI+: 644 |
| 34 | 5 | ESI+: 549 |
| 35 | 5 | ESI+: 566 |
| 36 | 5 | ESI+: 594 |
| 37 | 5 | ESI+: 568 |
| 38 | 5 | ESI+: 540 |
| 39 | 5 | ESI+: 570 |
| 40 | 5 | ESI+: 550 |
| 41 | 5 | ESI+: 553 |
| 42 | 5 | ESI+: 552 |
| 43 | 5 | ESI+: 528 |
| 44 | 5 | ESI+: 598 |
| 45 | 5 | ESI+: 548 |
| 46 | 5 | ESI+: 572 |
| 47 | 5 | ESI+: 561 |
| 48 | 7 | ESI+: 514 |
| 49 | 5 | ESI+: 570 |
| 50 | 4 | ESI+: 564 |
| 51 | 5 | ESI+: 596, 598 |
| 52 | 5 | ESI+: 588 |
| 53 | 4 | ESI+: 553 |
| 54 | 4 | ESI+: 549 |
| 55 | 5 | ESI+: 558 |
| 56 | 5 | ESI+: 558 |
| 57 | 4 | ESI+: 536 |
| 58 | 4 | ESI+: 546 |
| 59 | 5 | ESI+: 564 |
| 60 | 5 | ESI+: 569 |
| 61 | 5 | ESI+: 562 |
| 62 | 5 | ESI+: 562 |
| 63 | 5 | ESI+: 580 |
| 64 | 5 | ESI+: 532 |
| 65 | 5 | ESI+: 598 |

TABLE 75

| Ex | Syn | DAT |
|---|---|---|
| 66 | 5 | ESI+: 571 |
| 67 | 5 | ESI+: 594 |
| 68 | 5 | ESI+: 568 |
| 69 | 5 | ESI+: 578 |
| 70 | 5 | ESI+: 568 |
| 71 | 8 | ESI+: 558 |
| 72 | 5 | ESI+: 596 |
| 73 | 5 | ESI+: 560 |

TABLE 75-continued

| Ex | Syn | DAT |
|---|---|---|
| 74 | 5 | ESI+: 588 |
| 75 | 5 | ESI+: 550 |
| 76 | 5 | ESI+: 580 |
| 77 | 4 | ESI+: 572 |
| 78 | 8 | ESI+: 586 |
| 79 | 1 | ESI+: 576 |
| 80 | 5 | ESI+: 622 |
| 81 | 5 | ESI+: 582 |
| 82 | 4 | ESI+: 616 |
| 83 | 5 | ESI+: 558 |
| 84 | 2 | ESI+: 588 |
| 85 | 4 | ESI+: 592, 594 |
| 86 | 4 | ESI+: 562 |
| 87 | 87 | ESI+: 590<br>$^1$H-NMR (500 MHz, pyridine-d5, 90° C.)<br>δ ppm 1.07 (3H, d, J = 6.8 Hz) 1.76-1.90<br>(4H, m) 2.18 (3H, s) 2.48-2.58 (1H, m) 2.61-2.70<br>(1H, m) 2.70-2.84 (1H, m) 2.93-3.09 (2H, m) 3.14-3.37<br>(7H, m) 3.53-3.60 (1H, m) 3.70-3.76 (1H, m) 3.78-3.87<br>(1H, m) 3.92-3.99 (2H, m) 4.28-4.34 (1H, m) 6.83-6.90<br>(2H, m) 7.08-7.18 (2H, m) 7.22-7.27 (1H, m) 7.77-7.85<br>(1H, m) |

TABLE 76

| Ex | Syn | DAT |
|---|---|---|
| 88 | 5 | ESI+: 604<br>$^1$H-NMR (500 MHz, pyridine-d5, 90° C.) δ ppm 1.03 (3H, d, J = 6.1 Hz)<br>1.82-2.02 (4H, m) 2.15 (3H, s) 2.33 (3H, s) 2.48-2.66 (2H, m)<br>2.93-3.04 (2H, m) 3.05-3.12 (1H, m) 3.17-3.23 (2H, m)<br>3.24-3.34 (2H, m) 3.35-3.42 (1H, m) 3.43-3.51 (2H, m) 3.64-3.75 (2H, m)<br>3.90-3.98 (2H, m) 3.99-4.07 (1H, m) 4.30-4.39 (1H, m)<br>6.67-6.76 (2H, m) 7.09-7.19 (2H, m) 7.95 (1H, t. J = 8.2 Hz) |
| 89 | 87 | ESI+: 572<br>$^1$H NMR (500 MHz, pyridine-d5, 90° C.) δ ppm 1.01-1.21 (3H, m)<br>1.40 (9H, s) 2.16 (3H, s) 2.36 (6H, s) 2.49-2.61 (1H, m)<br>2.61-2.73 (1H, m) 2.90-3.08 (3H, m) 3.32 (1H, dd, J = 14.1, 7.5 Hz) 3.53 (1H, t,<br>J = 6.8 Hz) 3.58-3.70 (2H, m) 3.70-3.78 (1H, m) 3.86 (1H, dd,<br>J = 10.7, 6.7 Hz) 4.25-4.35 (1H, m) 4.35-4.46 (1H, m) 6.80 (2H, s)<br>7.11-7.21 (2H, m) 8.11-8.19 (1H, m) |
| 90 | 5 | ESI+: 536 |
| 91 | 5 | ESI+: 608 |
| 92 | 5 | ESI+: 616 |
| 93 | 5 | ESI+: 592 |
| 94 | 5 | ESI+: 600 |
| 95 | 5 | ESI+: 608 |
| 96 | 5 | ESI+: 588 |
| 97 | 5 | ESI+: 600 |
| 98 | 3 | ESI+: 520 |
| 99 | 4 | ESI+: 588 |
| 100 | 4 | ESI+: 604 |

INDUSTRIAL APPLICABILITY

The compound of the formula (I) or a salt thereof is a compound having an $MC_4$ receptor agonistic activity, and can be used as an active ingredient of a pharmaceutical composition for preventing or treating bladder and/or urinary tract diseases, in particular, underactive bladder, hypotonic bladder, acontractile bladder, detrusor underactivity, neurogenic bladder, urethral relaxation failure, detrusor-external urethral sphincter dyssynergia, and voiding dysfunctions in benign prostatic hyperplasia.

The invention claimed is:

1. A compound of formula (I) or a salt thereof:

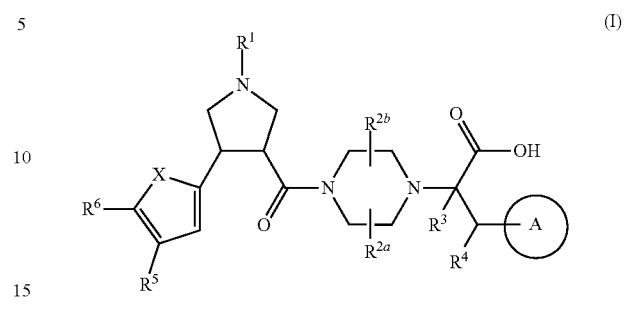

wherein:

$R^1$ is H, $C_{1-6}$ alkyl which may be substituted with OH, $C_{3-8}$ cycloalkyl which may be substituted with $R^{00}$, heterocycloalkyl which may be substituted with $R^{00}$, phenyl which may be substituted with $R^{00}$, heteroaryl which may be substituted with $R^{00}$, —CO—$C_{1-6}$ alkyl, or —CO—$C_{3-8}$ cycloalkyl, in which $R^{00}$ represents substituents selected from the group consisting of $C_{1-6}$ alkyl, halogeno-$C_{1-6}$ alkyl, and halogen, $R^{2a}$ is $C_{1-6}$ alkyl which may be substituted with $R^{01}$, in which $R^{01}$ represents substituents selected from the group consisting of $C_{3-8}$ cycloalkyl, —O—($C_{1-6}$ alkyl), —N($C_{1-6}$ alkyl)$_2$, —NH($C_{1-6}$ alkyl), and —NH$_2$, $R^{2b}$ is H or $C_{1-6}$ alkyl, $R^{2a}$ and $R^{2b}$ may be combined with the same carbon atom in the piperazine ring to form $C_{3-8}$ cycloalkyl, $R^3$ is H or $C_{1-6}$ alkyl, $R^4$ is H or $C_{1-6}$ alkyl, X is *—CR$^7$=CR$^8$—, *—CR$^7$=N—, *—N=CR$^8$—, or S, in which * represents a bond with a carbon atom substituted with R$^6$, R$^5$, R$^6$, and R$^7$ are the same as or different from each other, and are H, C$_{1-6}$ alkyl, —O—(C$_{1-6}$ alkyl), halogen, or CN, R$^5$ and R$^6$ may be combined with each other to form C$_{5-7}$ cycloalkenyl, R$^8$ is H or F, and the ring A is aryl which may be substituted with R$^{02}$, C$_{5-7}$ cycloalkenyl-fused phenyl which may be substituted with R$^{02}$, heteroaryl which may be substituted with R$^{02}$, or C$_{6-8}$ cycloalkyl which may be substituted with R$^{02}$, in which R$^{02}$ represents substituents selected from the group consisting of C$_{1-6}$ alkyl, halogeno-C$_{1-6}$ alkyl, C$_{3-8}$ cycloalkyl, —O—(C$_{1-6}$ alkyl), —O-(halogeno-C$_{1-6}$ alkyl), halogen, and —CN.

2. The compound or salt thereof according to claim 1, wherein

R$^1$ is
  (i) tert-butyl which may be substituted with OH,
  (ii) C$_{3-5}$ cycloalkyl which may be substituted with C$_{1-6}$ alkyl,
  (iii) 4-tetrahydropyranyl which may be substituted with C$_{1-6}$ alkyl,
  (iv) phenyl which may be substituted with halogen,
  (v) heteroaryl which may be substituted with substituents selected from the group consisting of C$_{1-6}$ alkyl and halogeno-C$_{1-6}$ alkyl,
  (vi) —CO—C$_{1-6}$ alkyl, or
  (vii) —CO—C$_{3-5}$ cycloalkyl, R$^{2a}$ is C$_{1-6}$ alkyl which may be substituted with R$^{03}$, in which R$^{03}$ represents substituents selected from the group consisting of C$_{3-5}$ cycloalkyl, —O—(C$_{1-6}$ alkyl), and —N(C$_{1-6}$ alkyl)$_2$, R$^{2b}$ is H or C$_{1-6}$ alkyl, R$^5$, R$^6$, and R$^7$ are the same as or different from each other, and are H, C$_{1-6}$ alkyl, or halogen, and the ring A is
  (i) aryl which may be substituted with substituents selected from the group consisting of C$_{1-6}$ alkyl, halogeno-C$_{1-6}$ alkyl, C$_{3-5}$ cycloalkyl, —O—(C$_{1-6}$ alkyl), —O—(halogeno-C$_{1-6}$ alkyl), halogen, and —CN,
  (ii) C$_{5-7}$ cycloalkenyl-fused phenyl which may be substituted with substituents selected from the group consisting of C$_{1-6}$ alkyl and halogen,
  (iii) heteroaryl which may be substituted with halogen, or
  (iv) C$_{6-8}$ cycloalkyl which may be substituted with C$_{1-6}$ alkyl.

3. ; The compound or salt thereof according to claim 2, wherein

R$^1$ is
  (i) tert-butyl,
  (ii) 4-tetrahydropyranyl,
  (iii) pyridyl which may be substituted with halogeno-C$_{1-6}$ alkyl, or
  (iv) 1,6-dihydro-6-oxopyridazinyl which may be substituted with C$_{1-6}$ alkyl, R$^{2a}$ is C$_{1-6}$ alkyl,
R$^{2b}$ is H,
R$^3$ is H or methyl,
R$^4$ is H or methyl,
X is *—CR$^7$=CR$^8$—, or *—N=CR$^8$—,
R$^5$ is H or halogen,
R$^6$ is halogen,
R$^7$ is H or halogen,
R$^8$ is F, and the ring A is
  (i) phenyl which may be substituted with substituents selected from the group consisting of C$_{1-6}$ alkyl, C$_{3-5}$ cycloalkyl and halogen,
  (ii) naphthyl,
  (iii) 2,3-dihydro-1H-inden-5-yl which may be substituted with substituents selected from the group consisting of C$_{1-6}$ alkyl and halogen,
  (iv) cyclohexyl which may be substituted with C$_{1-6}$ alkyl, or
  (v) cycloheptyl which may be substituted with C$_{1-6}$ alkyl.

4. The compound or salt thereof according to claim 3, which has the following formula (Ia):

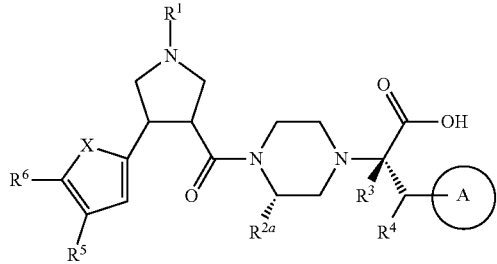

(Ia)

R$^1$ is
  (i) tert-butyl,
  (ii) 4-tetrahydropyranyl,
  (iii) pyridyl which may be substituted with difluoromethyl, or
  (iv) 1,6-dihydro-6-oxopyridazinyl which may be substituted with methyl, R$^{2a}$ is methyl, ethyl, or n-propyl,
X is *—CR$^7$=CR$^8$—,
R$^5$ is H,
R$^6$ is F or Cl,
R$^7$ is H, and the ring A is
  (i) phenyl which may be substituted with substituents selected from the group consisting of C$_{1-6}$ alkyl, C$_{3-5}$ cycloalkyl, and halogen,
  (ii) naphthyl,
  (iii) 2,3-dihydro-1H-inden-5-yl which may be substituted with substituents selected from the group consisting of C$_{1-6}$ alkyl and halogen, or
  (iv) cyclohexyl which may be substituted with C$_{1-6}$ alkyl.

5. The compound or salt thereof according to claim 4, which has the following formula (Ib):

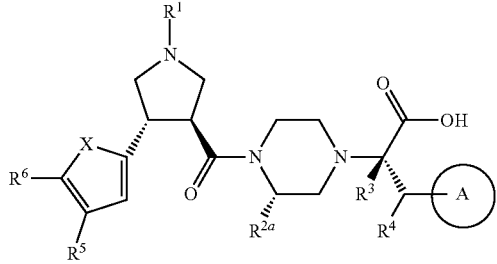

(Ib)

R¹ is
(i) tert-butyl or
(ii) 4-tetrahydropyranyl,
R³ is H,
R⁴ is H, and
the ring A is
(i) phenyl which may be substituted with substituents selected from the group consisting of $C_{1-6}$ alkyl and halogen,
(ii) naphthyl, or
(iii) 2,3-dihydro-1H-inden-5-yl.

6. The compound or salt thereof according to claim 1, wherein the compound is a compound selected from the group consisting of:
(2S)-2-[(3S)-4-{[(3S,4R)-4-(4-chloro-2-fluorophenyl)-1-(tetrahydro-2H-pyran-4-yl)pyrrolidin-3-yl]carbonyl}-3-methylpiperazin-1-yl]-3-(2-fluoro-4-methylphenyl)propanoic acid,
(2S)-2-[(3S)-4-{[(3S,4R)-4-(4-chloro-2-fluorophenyl)-1-(tetrahydro-2H-pyran-4-yl)pyrrolidin-3-yl]carbonyl}-3-methylpiperazin-1-yl]-3-(2-fluoro-4,6-dimethylphenyl)propanoic acid,
(2S)-2-[(3S)-4-{[(3S,4R)-1-tert-butyl-4-(4-chloro-2-fluorophenyl)pyrrolidin-3-yl]carbonyl}-3-methylpiperazin-1-yl]-3-mesitylpropanoic acid,
(2S)-2-[(3S)-4-{[(3S,4R)-1-tert-butyl-4-(4-chloro-2-fluorophenyl)pyrrolidin-3-yl]carbonyl}-3-methylpiperazin-1-yl]-3-(2-fluoro-4-methylphenyl)propanoic acid,
(2S)-2-[(3S)-4-{[(3S,4R)-1-tert-butyl-4-(2,4-difluorophenyl)pyrrolidin-3-yl]carbonyl}-3-methylpiperazin-1-yl]-3-(2,3-dihydro-1H-inden-5-yl)propanoic acid,
(2S)-2-[(3S)-4-{[(3S,4R)-1-tert-butyl-4-(2,4-difluorophenyl)pyrrolidin-3-yl]carbonyl}-3-propylpiperazin-1-yl]-3-(2-naphthyl)propanoic acid, and
(2S)-2-[(3S)-4-{[(3S,4R)-1-tert-butyl-4-(4-chloro-2-fluorophenyl)pyrrolidin-3-yl]carbonyl}-3-methylpiperazin-1-yl]-3-(4-methylphenyl)propanoic acid.

7. A pharmaceutical composition comprising a compound or salt thereof according to claim 6, and a pharmaceutically acceptable excipient.

8. A method for treating a bladder and/or urinary tract disease, comprising administering an effective amount of a compound or salt thereof according to claim 6 to a subject in need thereof.

9. The compound or a salt thereof according to claim 6, wherein the compound is
(2S)-2-[(3S)-4-{[(3S,4R)-4-(4-chloro-2-fluorophenyl)-1-(tetrahydro-2H-pyran-4-yl)pyrrolidin-3-yl]carbonyl}-3-methylpiperazin-1-yl]-3-(2-fluoro-4-methylphenyl)propanoic acid.

10. The compound or a salt thereof according to claim 6, wherein the compound is
(2S)-2-[(3S)-4-{[(3S,4R)-4-(4-chloro-2-fluorophenyl)-1-(tetrahydro-2H-pyran-4-yl)pyrrolidin-3-yl]carbonyl}-3-methylpiperazin-1-yl]-3-(2-fluoro-4,6-dimethylphenyl)propanoic acid.

11. The compound or a salt thereof according to claim 6, wherein the compound is
(2S)-2-[(3S)-4-{[(3S,4R)-1-tert-butyl-4-(4-chloro-2-fluorophenyl)pyrrolidin-3-yl]carbonyl}-3-methylpiperazin-1-yl]-3-mesitylpropanoic acid.

12. The compound or a salt thereof according to claim 6, wherein the compound is
(2S)-2-[(3S)-4-{[(3S,4R)-1-tert-butyl-4-(4-chloro-2-fluorophenyl)pyrrolidin-3-yl]carbonyl}-3-methylpiperazin-1-yl]-3-(2-fluoro-4-methylphenyl)propanoic acid.

13. The compound or a salt thereof according to claim 6, wherein the compound is
(2S)-2-[(3S)-4-{[(3S,4R)-1-tert-butyl-4-(2,4-difluorophenyl)pyrrolidin-3-yl]carbonyl}-3 -methylpiperazin-1-yl]-3-(2,3-dihydro-1H-inden-5-yl)propanoic acid.

14. The compound or a salt thereof according to claim 6, wherein the compound is
(2S)-2-[(3S)-4-{[(3S,4R)-1-tert-butyl-4-(2,4-difluorophenyl)pyrrolidin-3-yl]carbonyl}-3-propylpiperazin-1-yl]-3-(2-naphthyl)propanoic acid.

15. The compound or a salt thereof according to claim 6, wherein the compound is
(2S)-2-[(3S)-4-{[(3S,4R)-1-tert-butyl-4-(4-chloro-2-fluorophenyl)pyrrolidin-3-yl]carbonyl}-3-methylpiperazin-1-yl]-3-(4-methylphenyl)propanoic acid.

* * * * *